United States Patent
Barthe et al.

(10) Patent No.: US 10,537,304 B2
(45) Date of Patent: Jan. 21, 2020

(54) HAND WAND FOR ULTRASONIC COSMETIC TREATMENT AND IMAGING

(75) Inventors: Peter G. Barthe, Phoenix, AZ (US);
Michael H. Slayton, Tempe, AZ (US);
Inder Raj S. Makin, Mesa, AZ (US)

(73) Assignee: Ulthera, Inc., Mesa, AZ (US)

( * ) Notice: Subject to any disclaimer, the term of this patent is extended or adjusted under 35 U.S.C. 154(b) by 0 days.

(21) Appl. No.: 12/996,616

(22) PCT Filed: Jun. 5, 2009

(86) PCT No.: PCT/US2009/046475
§ 371 (c)(1),
(2), (4) Date: Jan. 12, 2011

(87) PCT Pub. No.: WO2009/149390
PCT Pub. Date: Dec. 10, 2009

(65) Prior Publication Data
US 2011/0112405 A1 May 12, 2011

Related U.S. Application Data

(60) Provisional application No. 61/059,477, filed on Jun. 6, 2008.

(51) Int. Cl.
*A61B 8/08* (2006.01)
(52) U.S. Cl.
CPC .................. *A61B 8/0858* (2013.01)
(58) Field of Classification Search
USPC .................. 600/437–463; 601/1, 2
See application file for complete search history.

(56) References Cited

U.S. PATENT DOCUMENTS

| | | | |
|---|---|---|---|
| 2,427,348 A | 9/1947 | Bond et al. | |
| 2,792,829 A | 2/1952 | Calosi | |

(Continued)

FOREIGN PATENT DOCUMENTS

| | | |
|---|---|---|
| CN | 104027893 | 9/2014 |
| DE | 4029175 | 3/1992 |

(Continued)

OTHER PUBLICATIONS

Chen, L. et al., "Effect of Blood Perfusion on the ablation of liver perenchyma with high intensity focused ultrasound," Phys. Med. Biol; 38:1661-1673; 1993b.

(Continued)

*Primary Examiner* — Thomas J Hong
*Assistant Examiner* — Shahdeep Mohammed
(74) *Attorney, Agent, or Firm* — Knobbe Martens Olson & Bear LLP

(57) ABSTRACT

Embodiments of the invention provide a dermatological cosmetic treatment and imaging system and method. In some embodiments, the system (20) includes a hand wand (100) with at least one finger activated controller (150, 160), and a removable transducer module (200) having an ultrasound transducer (280). In some embodiments, the system (20) can include a control module (300) that is coupled to the hand wand (100) and has a graphical user interface (310) for controlling the removable transducer module (200), and an interface (130) coupling the hand wand (100) to the control module (300). The interface (130) may provide power to the hand wand or may transfer a signal from the hand wand to the control module. In some embodiments, the cosmetic treatment system (20) may be used in cosmetic procedures on at least a portion of a face, head, neck, and/or other part of a patient.

10 Claims, 16 Drawing Sheets

(56) References Cited

U.S. PATENT DOCUMENTS

| | | |
|---|---|---|
| 3,913,386 A | 10/1975 | Saglio |
| 3,965,455 A | 6/1976 | Hurwitz |
| 3,992,925 A | 11/1976 | Perilhou |
| 4,039,312 A | 8/1977 | Patru |
| 4,059,098 A | 11/1977 | Murdock |
| 4,101,795 A | 7/1978 | Fukumoto |
| 4,151,834 A * | 5/1979 | Sato ................. A61B 8/08 367/104 |
| 4,166,967 A | 9/1979 | Benes et al. |
| 4,211,948 A | 7/1980 | Smith et al. |
| 4,211,949 A | 7/1980 | Brisken et al. |
| 4,213,344 A | 7/1980 | Rose |
| 4,276,491 A | 6/1981 | Daniel |
| 4,315,514 A | 2/1982 | Drewes et al. |
| 4,325,381 A | 4/1982 | Glenn |
| 4,343,301 A | 8/1982 | Indech |
| 4,372,296 A | 2/1983 | Fahim |
| 4,379,145 A | 4/1983 | Masuho et al. |
| 4,381,007 A | 4/1983 | Doss |
| 4,381,787 A | 5/1983 | Hottinger |
| 4,397,314 A | 8/1983 | Vaguine |
| 4,409,839 A | 10/1983 | Tanezer |
| 4,431,008 A | 2/1984 | Wanner et al. |
| 4,441,486 A | 4/1984 | Pounds |
| 4,452,084 A | 6/1984 | Taenzer |
| 4,484,569 A | 11/1984 | Driller |
| 4,507,582 A | 3/1985 | Glenn |
| 4,513,749 A | 4/1985 | Kino |
| 4,513,750 A | 4/1985 | Heyman et al. |
| 4,527,550 A | 7/1985 | Ruggera et al. |
| 4,528,979 A | 7/1985 | Marchenko |
| 4,534,221 A | 8/1985 | Fife et al. |
| 4,566,459 A | 1/1986 | Umemura et al. |
| 4,567,895 A | 2/1986 | Putzke |
| 4,586,512 A | 5/1986 | Do-Huu |
| 4,601,296 A | 7/1986 | Yerushalmi |
| 4,620,546 A | 11/1986 | Aida et al. |
| 4,637,256 A | 1/1987 | Sugiyama et al. |
| 4,646,756 A | 3/1987 | Watmough |
| 4,663,358 A | 5/1987 | Hyon |
| 4,668,516 A | 5/1987 | Duraffourd et al. |
| 4,672,591 A | 6/1987 | Breimesser et al. |
| 4,680,499 A | 7/1987 | Umemura et al. |
| 4,697,588 A | 10/1987 | Reichenberger |
| 4,754,760 A | 7/1988 | Fukukita et al. |
| 4,757,820 A | 7/1988 | Itoh |
| 4,771,205 A | 9/1988 | Mequio |
| 4,801,459 A | 1/1989 | Liburdy |
| 4,803,625 A | 2/1989 | Fu et al. |
| 4,807,633 A | 2/1989 | Fry |
| 4,817,615 A | 4/1989 | Fukukita et al. |
| 4,858,613 A | 8/1989 | Fry |
| 4,860,732 A | 8/1989 | Hasegawa et al. |
| 4,865,041 A | 9/1989 | Hassler |
| 4,865,042 A | 9/1989 | Umemura |
| 4,867,169 A | 9/1989 | Machida |
| 4,874,562 A | 10/1989 | Hyon |
| 4,875,487 A | 10/1989 | Seppi |
| 4,881,212 A | 11/1989 | Takeuchi |
| 4,891,043 A | 1/1990 | Zeimer et al. |
| 4,893,624 A | 1/1990 | Lele |
| 4,896,673 A | 1/1990 | Rose |
| 4,900,540 A | 2/1990 | Ryan et al. |
| 4,901,729 A | 2/1990 | Saitoh |
| 4,917,096 A | 4/1990 | Englehart |
| 4,973,096 A | 4/1990 | Jaworski |
| 4,932,414 A | 6/1990 | Coleman et al. |
| 4,938,216 A | 7/1990 | Lele |
| 4,938,217 A | 7/1990 | Lele |
| 4,947,046 A | 8/1990 | Kawabata et al. |
| 4,951,653 A | 8/1990 | Fry |
| 4,955,365 A | 9/1990 | Fry |
| 4,958,626 A | 9/1990 | Nambu |
| 4,976,709 A | 12/1990 | Sand |
| 4,979,501 A | 12/1990 | Valchanov |
| 4,992,989 A | 2/1991 | Watanabe et al. |
| 5,012,797 A | 5/1991 | Liang |
| 5,018,508 A | 5/1991 | Fry et al. |
| 5,030,874 A | 7/1991 | Saito et al. |
| 5,036,855 A | 8/1991 | Fry |
| 5,040,537 A | 8/1991 | Katakura |
| 5,054,310 A | 10/1991 | Flynn |
| 5,054,470 A | 10/1991 | Fry |
| 5,054,491 A | 10/1991 | Saito et al. |
| 5,070,879 A | 12/1991 | Herres |
| 5,088,495 A | 2/1992 | Miyagawa |
| 5,115,814 A | 5/1992 | Griffith |
| 5,117,832 A | 6/1992 | Sanghvi |
| 5,123,418 A | 6/1992 | Saurel |
| 5,142,511 A | 8/1992 | Kanai et al. |
| 5,143,063 A | 9/1992 | Fellner |
| 5,143,074 A | 9/1992 | Dory |
| 5,149,319 A | 9/1992 | Unger |
| 5,150,711 A | 9/1992 | Dory |
| 5,150,714 A | 9/1992 | Green |
| 5,152,294 A | 10/1992 | Mochizuki et al. |
| 5,156,144 A | 10/1992 | Iwasaki |
| 5,158,536 A | 10/1992 | Sekins |
| 5,159,931 A | 11/1992 | Pini |
| 5,163,421 A | 11/1992 | Bernstein |
| 5,163,436 A | 11/1992 | Saitoh et al. |
| 5,178,135 A | 1/1993 | Uchiyama et al. |
| 5,190,518 A | 3/1993 | Takasu |
| 5,190,766 A | 3/1993 | Ishihara |
| 5,191,880 A | 3/1993 | McLeod |
| 5,205,287 A | 4/1993 | Erbel et al. |
| 5,209,720 A | 5/1993 | Unger |
| 5,212,671 A | 5/1993 | Fujii et al. |
| 5,215,680 A | 6/1993 | D'Arrigo |
| 5,224,467 A | 7/1993 | Oku |
| 5,230,334 A | 7/1993 | Klopotek |
| 5,230,338 A | 7/1993 | Allen et al. |
| 5,247,924 A | 9/1993 | Suzuki et al. |
| 5,255,681 A | 10/1993 | Ishimura et al. |
| 5,257,970 A | 11/1993 | Dougherty |
| 5,265,614 A | 11/1993 | Hayakawa |
| 5,267,985 A | 12/1993 | Shimada et al. |
| 5,269,297 A | 12/1993 | Weng |
| 5,282,797 A | 2/1994 | Chess |
| 5,295,484 A | 3/1994 | Marcus |
| 5,295,486 A | 3/1994 | Wollschlager et al. |
| 5,304,169 A | 4/1994 | Sand |
| 5,305,756 A | 4/1994 | Entrekin et al. |
| 5,321,520 A | 6/1994 | Inge et al. |
| 5,323,779 A | 6/1994 | Hardy et al. |
| 5,327,895 A | 7/1994 | Hashimoto et al. |
| 5,329,202 A | 7/1994 | Garlick et al. |
| 5,348,016 A | 9/1994 | Unger et al. |
| 5,358,466 A | 10/1994 | Aida et al. |
| 5,360,268 A | 11/1994 | Hayashi |
| 5,370,121 A | 12/1994 | Reichenberger |
| 5,370,122 A | 12/1994 | Kunig et al. |
| 5,371,483 A | 12/1994 | Bhardwaj |
| 5,375,602 A | 12/1994 | Lancee et al. |
| 5,379,773 A | 1/1995 | Hornsby |
| 5,380,280 A | 1/1995 | Peterson |
| 5,380,519 A | 1/1995 | Schneider et al. |
| 5,383,917 A | 1/1995 | Desai et al. |
| 5,391,140 A | 2/1995 | Schaetzle et al. |
| 5,391,197 A | 2/1995 | Burdette et al. |
| 5,392,259 A | 2/1995 | Bolorforosh |
| 5,396,143 A | 3/1995 | Seyed-Bolorforosh et al. |
| 5,398,689 A | 3/1995 | Connor et al. |
| 5,406,503 A | 4/1995 | Williams |
| 5,413,550 A | 5/1995 | Castel |
| 5,417,216 A | 5/1995 | Tanaka |
| 5,419,327 A | 5/1995 | Rohwedder |
| 5,423,220 A | 6/1995 | Finsterwald et al. |
| 5,435,311 A | 7/1995 | Umemura |
| 5,438,998 A | 8/1995 | Hanafy |
| 5,443,068 A | 8/1995 | Cline et al. |
| 5,445,611 A | 8/1995 | Eppstein et al. |
| 5,458,596 A | 10/1995 | Lax |
| 5,460,179 A | 10/1995 | Okunuki et al. |

(56) References Cited

U.S. PATENT DOCUMENTS

| | | |
|---|---|---|
| 5,460,595 A | 10/1995 | Hall et al. |
| 5,469,854 A | 11/1995 | Unger et al. |
| 5,471,488 A | 12/1995 | Fujio |
| 5,472,405 A | 12/1995 | Buchholtz et al. |
| 5,487,388 A | 1/1996 | Rello et al. |
| 5,492,126 A | 2/1996 | Hennige |
| 5,496,256 A | 3/1996 | Bock |
| 5,501,655 A | 3/1996 | Rolt |
| 5,503,152 A | 4/1996 | Oakley et al. |
| 5,503,320 A | 4/1996 | Webster et al. |
| 5,507,790 A | 4/1996 | Weiss |
| 5,511,296 A | 4/1996 | Dias et al. |
| 5,520,188 A | 5/1996 | Hennige |
| 5,522,869 A | 6/1996 | Burdette |
| 5,523,058 A | 6/1996 | Umemura et al. |
| 5,524,620 A | 6/1996 | Rosenchein |
| 5,524,624 A | 6/1996 | Tepper |
| 5,524,625 A | 6/1996 | Okazaki |
| 5,526,624 A * | 6/1996 | Berg ............................. 52/419 |
| 5,526,812 A | 6/1996 | Dumoulin et al. |
| 5,526,814 A | 6/1996 | Cline et al. |
| 5,526,815 A | 6/1996 | Granz |
| 5,529,070 A | 6/1996 | Augustine et al. |
| 5,540,235 A | 7/1996 | Wilson |
| 5,558,092 A | 9/1996 | Unger |
| 5,560,362 A | 10/1996 | Sliwa et al. |
| 5,573,497 A | 11/1996 | Chapelon |
| 5,575,291 A | 11/1996 | Hayakawa |
| 5,575,807 A | 11/1996 | Faller |
| 5,577,502 A | 11/1996 | Darrow et al. |
| 5,577,507 A | 11/1996 | Snyder et al. |
| 5,577,991 A | 11/1996 | Akui et al. |
| 5,580,575 A | 12/1996 | Unger et al. |
| 5,643,179 A | 1/1997 | Fujimoto |
| 5,601,526 A | 2/1997 | Chapelon |
| 5,603,323 A | 2/1997 | Pflugrath et al. |
| 5,605,154 A | 2/1997 | Ries et al. |
| 5,609,562 A | 3/1997 | Kaali |
| 5,615,091 A | 3/1997 | Palatnik |
| 5,617,858 A | 4/1997 | Taverna et al. |
| 5,618,275 A | 4/1997 | Bock |
| 5,620,479 A | 4/1997 | Diederich |
| 5,622,175 A | 4/1997 | Sudol et al. |
| 5,638,819 A | 6/1997 | Manwaring et al. |
| 5,644,085 A | 7/1997 | Lorraine et al. |
| 5,647,373 A | 7/1997 | Paltieli |
| 5,655,535 A | 8/1997 | Frlemel et al. |
| 5,655,538 A | 8/1997 | Lorraine |
| 5,657,760 A | 8/1997 | Ying |
| 5,658,328 A | 8/1997 | Johnson |
| 5,660,836 A | 8/1997 | Knowlton |
| 5,662,116 A | 9/1997 | Kondo |
| 5,665,053 A | 9/1997 | Jacobs |
| 5,665,141 A | 9/1997 | Vago |
| 5,671,746 A | 9/1997 | Dreschel et al. |
| 5,673,699 A | 10/1997 | Trahey et al. |
| 5,676,692 A | 10/1997 | Sanghvi |
| 5,685,820 A | 11/1997 | Riek et al. |
| 5,690,608 A | 11/1997 | Watanabe |
| 5,694,936 A | 12/1997 | Fujimoto |
| 5,697,897 A | 12/1997 | Buchholtz |
| 5,701,900 A | 12/1997 | Shehada et al. |
| 5,704,361 A | 1/1998 | Seward et al. |
| 5,706,252 A | 1/1998 | Le Verrier et al. |
| 5,706,564 A | 1/1998 | Rhyne |
| 5,715,823 A | 2/1998 | Wood et al. |
| 5,720,287 A | 2/1998 | Chapelon et al. |
| 5,722,411 A | 3/1998 | Suzuki |
| 5,727,554 A | 3/1998 | Kalend et al. |
| 5,735,280 A | 4/1998 | Sherman et al. |
| 5,743,863 A | 4/1998 | Chapelon |
| 5,746,005 A | 5/1998 | Steinberg |
| 5,746,762 A | 5/1998 | Bass |
| 5,748,767 A | 5/1998 | Raab |
| 5,749,364 A | 5/1998 | Sliwa et al. |
| 5,755,228 A | 5/1998 | Wilson et al. |
| 5,755,753 A | 5/1998 | Knowlton |
| 5,762,066 A | 6/1998 | Law |
| 5,763,886 A | 6/1998 | Schulte |
| 5,769,790 A | 6/1998 | Watkins |
| 5,779,644 A | 7/1998 | Eberle et al. |
| 5,792,058 A | 8/1998 | Lee |
| 5,795,297 A | 8/1998 | Daigle |
| 5,795,311 A | 8/1998 | Wess |
| 5,714,599 A | 9/1998 | Mitragotri et al. |
| 5,810,009 A | 9/1998 | Mine et al. |
| 5,810,888 A | 9/1998 | Fenn |
| 5,814,599 A | 9/1998 | Mitragotri et al. |
| 5,817,013 A | 10/1998 | Ginn et al. |
| 5,817,021 A | 10/1998 | Reichenberger |
| 5,820,564 A | 10/1998 | Slayton |
| 5,823,962 A | 10/1998 | Schaetzle |
| 5,827,204 A | 10/1998 | Grandia et al. |
| 5,839,751 A | 11/1998 | Bonin |
| 5,840,032 A | 11/1998 | Hatfield et al. |
| 5,844,140 A | 12/1998 | Seale |
| 5,853,367 A | 12/1998 | Chalek et al. |
| 5,857,970 A | 1/1999 | Purdy |
| 5,869,751 A | 2/1999 | Bonin |
| 5,871,524 A | 2/1999 | Knowlton |
| 5,873,902 A | 2/1999 | Sanghvi |
| 5,876,341 A | 3/1999 | Wang et al. |
| 5,879,303 A | 3/1999 | Averkiou et al. |
| 5,882,557 A | 3/1999 | Hayakawa |
| 5,891,034 A | 4/1999 | Bucholz |
| 5,895,356 A | 4/1999 | Andrus et al. |
| 5,899,861 A | 5/1999 | Friemel et al. |
| 5,904,659 A | 5/1999 | Duarte |
| 5,919,219 A | 7/1999 | Knowlton |
| 5,923,099 A | 7/1999 | Bilir |
| 5,924,989 A | 7/1999 | Polz |
| 5,928,169 A | 7/1999 | Schatzle et al. |
| 5,931,805 A | 8/1999 | Brisken |
| 5,938,606 A | 8/1999 | Bonnefous |
| 5,938,612 A | 8/1999 | Kline-Schoder |
| 5,948,011 A | 9/1999 | Knowlton |
| 5,957,844 A | 9/1999 | Dekel |
| 5,957,882 A | 9/1999 | Nita et al. |
| 5,957,941 A | 9/1999 | Ream |
| 5,964,707 A | 10/1999 | Fenster et al. |
| 5,967,980 A | 10/1999 | Ferre et al. |
| 5,968,034 A | 10/1999 | Fulmer |
| 5,971,949 A | 10/1999 | Levin |
| 5,977,538 A | 11/1999 | Unger et al. |
| 5,984,881 A | 11/1999 | Ishibashi et al. |
| 5,984,882 A | 11/1999 | Rosenchein |
| 5,990,598 A | 11/1999 | Sudol et al. |
| 5,997,471 A | 12/1999 | Gumb et al. |
| 5,997,497 A | 12/1999 | Nita et al. |
| 5,999,843 A | 12/1999 | Anbar |
| 6,004,262 A | 12/1999 | Putz et al. |
| 6,007,499 A | 12/1999 | Martin et al. |
| 6,013,032 A | 1/2000 | Savord |
| 6,014,473 A | 1/2000 | Hossack et al. |
| 6,016,255 A | 1/2000 | Bolan et al. |
| 6,019,724 A | 2/2000 | Gronningsaeter et al. |
| 6,022,308 A | 2/2000 | Williams |
| 6,022,317 A | 2/2000 | Cruanas et al. |
| 6,022,327 A | 2/2000 | Chang |
| 6,030,374 A | 2/2000 | McDaniel |
| 6,036,646 A | 3/2000 | Barthe |
| 6,039,048 A | 3/2000 | Silberg |
| 6,039,689 A | 3/2000 | Lizzi |
| 6,042,556 A | 3/2000 | Beach et al. |
| 6,049,159 A | 4/2000 | Barthe |
| 6,050,943 A | 4/2000 | Slayton |
| 6,059,727 A | 5/2000 | Fowlkes |
| 6,071,239 A | 6/2000 | Cribbs |
| 6,080,108 A | 6/2000 | Dunham |
| 6,083,148 A | 7/2000 | Williams |
| 6,086,535 A | 7/2000 | Ishibashi |
| 6,086,580 A | 7/2000 | Mordon et al. |
| 6,090,054 A | 7/2000 | Tagishi |
| 6,093,148 A | 7/2000 | Fujimoto |

(56) References Cited

U.S. PATENT DOCUMENTS

| | | | |
|---|---|---|---|
| 6,093,883 A | 7/2000 | Sanghvi |
| 6,101,407 A | 8/2000 | Groezinger |
| 6,113,558 A | 9/2000 | Rosenchein |
| 6,113,559 A | 9/2000 | Klopotek |
| 6,120,452 A | 9/2000 | Barthe |
| 6,123,081 A | 9/2000 | Durette |
| 6,126,619 A | 10/2000 | Peterson et al. |
| 6,135,971 A | 10/2000 | Hutchinson et al. |
| 6,139,499 A | 10/2000 | Wilk |
| 6,159,150 A | 12/2000 | Yale et al. |
| 6,171,244 B1 | 1/2001 | Finger et al. |
| 6,176,840 B1 | 1/2001 | Nishimura |
| 6,183,426 B1 | 2/2001 | Akisada |
| 6,183,502 B1 | 2/2001 | Takeuchi |
| 6,183,773 B1 | 2/2001 | Anderson |
| 6,190,323 B1 | 2/2001 | Digs |
| 6,190,336 B1 | 2/2001 | Duarte |
| 6,193,658 B1 | 2/2001 | Wendelken et al. |
| 6,198,956 B1 | 3/2001 | Dunne |
| 6,210,327 B1 | 4/2001 | Brackett et al. |
| 6,213,948 B1 | 4/2001 | Barthe |
| 6,216,029 B1 | 4/2001 | Paltieli |
| 6,233,476 B1 | 5/2001 | Strommer et al. |
| 6,234,990 B1 | 5/2001 | Rowe et al. |
| 6,241,753 B1 | 6/2001 | Knowlton |
| 6,246,898 B1 | 6/2001 | Vesely et al. |
| 6,251,074 B1 | 6/2001 | Averkiou et al. |
| 6,251,088 B1 | 6/2001 | Kaufman et al. |
| 6,268,405 B1 | 7/2001 | Yao |
| 6,273,864 B1 | 8/2001 | Duarte |
| 6,280,402 B1 * | 8/2001 | Ishibashi et al. ............... 601/2 |
| 6,287,257 B1 | 9/2001 | Matichuk |
| 6,287,304 B1 * | 9/2001 | Eggers et al. ............... 606/37 |
| 6,296,619 B1 | 10/2001 | Brisken |
| 6,301,989 B1 | 10/2001 | Brown et al. |
| 6,307,302 B1 | 10/2001 | Toda |
| 6,309,355 B1 | 10/2001 | Cain et al. |
| 6,311,090 B1 | 10/2001 | Knowlton |
| 6,315,741 B1 | 11/2001 | Martin |
| 6,322,509 B1 | 11/2001 | Pan et al. |
| 6,322,532 B1 | 11/2001 | D'Sa |
| 6,324,769 B1 | 12/2001 | Klopotek |
| 6,325,540 B1 | 12/2001 | Lounsberry et al. |
| 6,325,758 B1 | 12/2001 | Carol et al. |
| 6,325,769 B1 | 12/2001 | Klopotek |
| 6,325,798 B1 | 12/2001 | Edwards et al. |
| 6,350,276 B1 | 2/2002 | Knowlton |
| 6,356,780 B1 | 3/2002 | Licato et al. |
| 6,361,531 B1 | 3/2002 | Hissong |
| 6,370,411 B1 | 4/2002 | Osadchy et al. |
| 6,375,672 B1 | 4/2002 | Aksan |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,390,982 B1 | 5/2002 | Bova et al. |
| 6,405,090 B1 | 6/2002 | Knowlton |
| 6,409,720 B1 | 6/2002 | Hissong |
| 6,413,216 B1 | 7/2002 | Cain et al. |
| 6,413,253 B1 | 7/2002 | Koop |
| 6,413,254 B1 | 7/2002 | Hissong |
| 6,419,648 B1 | 7/2002 | Vitek |
| 6,423,007 B2 | 7/2002 | Lizzi et al. |
| 6,425,865 B1 | 7/2002 | Salcudean |
| 6,425,867 B1 | 7/2002 | Veazy |
| 6,425,912 B1 | 7/2002 | Knowlton |
| 6,428,477 B1 | 8/2002 | Mason |
| 6,428,532 B1 | 8/2002 | Doukas |
| 6,430,446 B1 | 8/2002 | Knowlton |
| 6,432,057 B1 | 8/2002 | Mazess et al. |
| 6,432,067 B1 | 8/2002 | Martin |
| 6,432,101 B1 | 8/2002 | Weber |
| 6,436,061 B1 | 8/2002 | Costantino |
| 6,438,424 B1 | 8/2002 | Knowlton |
| 6,440,071 B1 | 8/2002 | Slayton |
| 6,440,121 B1 | 8/2002 | Weber |
| 6,443,914 B1 | 9/2002 | Constantino |
| 6,447,443 B1 | 9/2002 | Keogh et al. |
| 6,450,979 B1 | 9/2002 | Miwa et al. |
| 6,451,013 B1 | 9/2002 | Bays et al. |
| 6,453,202 B1 | 9/2002 | Knowlton |
| 6,461,304 B1 | 10/2002 | Tanaka et al. |
| 6,461,378 B1 | 10/2002 | Knowlton |
| 6,470,216 B1 | 10/2002 | Knowlton |
| 6,338,716 B1 | 11/2002 | Hossack et al. |
| 6,488,626 B1 | 12/2002 | Lizzi |
| 6,491,657 B2 | 12/2002 | Rowe |
| 6,500,121 B1 | 12/2002 | Slayton |
| 6,500,141 B1 | 12/2002 | Irion |
| 6,506,171 B1 | 1/2003 | Vitek et al. |
| 6,508,774 B1 | 1/2003 | Rowe |
| 6,511,427 B1 | 1/2003 | Sliwa, Jr. et al. |
| 6,511,428 B1 | 1/2003 | Azuma |
| 6,514,244 B2 | 2/2003 | Pope |
| 6,517,484 B1 | 2/2003 | Wilk et al. |
| 6,524,250 B1 | 2/2003 | Weber |
| 6,666,835 B2 | 3/2003 | Martin |
| 6,540,679 B2 | 4/2003 | Slayton |
| 6,540,700 B1 | 4/2003 | Fujimoto et al. |
| 6,547,788 B1 | 4/2003 | Maguire et al. |
| 6,554,771 B1 | 4/2003 | Buil et al. |
| 6,569,099 B1 | 5/2003 | Babaev |
| 6,569,108 B2 | 5/2003 | Sarvazyan et al. |
| 6,572,552 B2 | 6/2003 | Fukukita |
| 6,575,956 B1 | 6/2003 | Brisken et al. |
| 6,595,934 B1 | 7/2003 | Hissong |
| 6,599,256 B1 | 7/2003 | Acker |
| 6,605,043 B1 | 8/2003 | Dreschel |
| 6,605,080 B1 | 8/2003 | Altshuler et al. |
| 6,607,498 B2 | 8/2003 | Eshel |
| 6,618,620 B1 | 9/2003 | Freundlich et al. |
| 6,623,430 B1 | 9/2003 | Slayton |
| 6,626,854 B2 | 9/2003 | Friedman |
| 6,626,855 B1 | 9/2003 | Weng |
| 6,638,226 B2 | 10/2003 | He et al. |
| 6,645,145 B1 | 11/2003 | Dreschel et al. |
| 6,645,150 B2 | 11/2003 | Angelsen et al. |
| 6,645,162 B2 | 11/2003 | Friedman |
| 6,662,054 B2 | 12/2003 | Kreindel |
| 6,663,627 B2 | 12/2003 | Francischelli |
| 6,665,806 B1 | 12/2003 | Shimizu |
| 6,669,638 B1 | 12/2003 | Miller |
| 6,685,639 B1 | 2/2004 | Wang et al. |
| 6,685,640 B1 | 2/2004 | Fry |
| 6,692,450 B1 | 2/2004 | Coleman |
| 6,699,237 B2 | 3/2004 | Weber |
| 6,716,184 B2 | 4/2004 | Vaezy et al. |
| 6,719,449 B1 | 4/2004 | Laughlin |
| 6,719,694 B2 | 4/2004 | Weng |
| 6,726,627 B1 | 4/2004 | Lizzi et al. |
| 6,733,449 B1 | 5/2004 | Krishnamurthy et al. |
| 6,749,624 B2 | 6/2004 | Knowlton |
| 6,772,490 B2 | 8/2004 | Toda |
| 6,773,409 B2 | 8/2004 | Truckai et al. |
| 6,775,404 B1 | 8/2004 | Pagoulatos et al. |
| 6,790,187 B2 | 9/2004 | Thompson et al. |
| 6,824,516 B2 | 11/2004 | Batten et al. |
| 6,825,176 B2 | 11/2004 | White et al. |
| 6,835,940 B2 | 12/2004 | Morikawa et al. |
| 6,846,290 B2 | 1/2005 | Lizzi et al. |
| 6,875,176 B2 | 4/2005 | Mourad et al. |
| 6,882,884 B1 | 4/2005 | Mosk et al. |
| 6,887,239 B2 | 5/2005 | Elstrom |
| 6,889,089 B2 | 5/2005 | Behl |
| 6,896,657 B2 | 5/2005 | Willis |
| 6,902,536 B2 | 6/2005 | Manna |
| 6,905,466 B2 | 6/2005 | Salgo |
| 6,918,907 B2 | 7/2005 | Kelly |
| 6,920,883 B2 | 7/2005 | Bessette |
| 6,921,371 B2 | 7/2005 | Wilson |
| 6,932,771 B2 | 8/2005 | Whitmore |
| 6,932,814 B2 | 8/2005 | Wood |
| 6,936,044 B2 | 8/2005 | McDaniel |

(56) References Cited

U.S. PATENT DOCUMENTS

| | | |
|---|---|---|
| 6,936,046 B2 | 8/2005 | Hissong |
| 6,945,937 B2 | 9/2005 | Culp et al. |
| 6,948,843 B2 | 9/2005 | Laugharn et al. |
| 6,953,941 B2 | 10/2005 | Nakano et al. |
| 6,958,043 B2 | 10/2005 | Hissong |
| 6,971,994 B1 | 12/2005 | Young et al. |
| 6,974,417 B2 | 12/2005 | Lockwood |
| 6,976,492 B2 | 12/2005 | Ingle |
| 6,992,305 B2 | 1/2006 | Maezawa et al. |
| 6,997,923 B2 | 2/2006 | Anderson |
| 7,006,874 B2 | 2/2006 | Knowlton |
| 7,020,528 B2 | 3/2006 | Neev |
| 7,022,089 B2 | 4/2006 | Ooba |
| 7,058,440 B2 | 6/2006 | Heuscher et al. |
| 7,063,666 B2 | 6/2006 | Weng |
| 7,070,565 B2 | 7/2006 | Vaezy et al. |
| 7,094,252 B2 | 8/2006 | Koop |
| 7,108,663 B2 | 9/2006 | Talish et al. |
| 7,115,123 B2 | 10/2006 | Knowlton |
| 7,122,029 B2 | 10/2006 | Koop et al. |
| 7,142,905 B2 | 11/2006 | Slayton |
| 7,165,451 B1 | 1/2007 | Brooks et al. |
| 7,179,238 B2 | 2/2007 | Hissong |
| 7,189,230 B2 | 3/2007 | Knowlton |
| 7,229,411 B2 | 6/2007 | Slayton |
| 7,235,592 B2 | 6/2007 | Muratoglu |
| 7,258,674 B2 | 8/2007 | Cribbs |
| 7,273,459 B2 | 9/2007 | Desilets |
| 7,294,125 B2 | 11/2007 | Phalen et al. |
| 7,297,117 B2 | 11/2007 | Trucco et al. |
| 7,303,555 B2 | 12/2007 | Makin et al. |
| 7,311,679 B2 | 12/2007 | Desilets et al. |
| 7,327,071 B2 | 2/2008 | Nishiyama et al. |
| 7,331,951 B2 | 2/2008 | Eshel et al. |
| 7,332,985 B2 | 2/2008 | Larson et al. |
| 7,338,434 B1 | 3/2008 | Haarstad et al. |
| 7,347,855 B2 | 3/2008 | Eshel |
| RE40,403 E | 6/2008 | Cho et al. |
| 7,393,325 B2 | 7/2008 | Barthe |
| 7,398,116 B2 | 7/2008 | Edwards |
| 7,399,279 B2 | 7/2008 | Abend et al. |
| 7,491,171 B2 | 2/2009 | Barthe et al. |
| 7,507,235 B2 | 3/2009 | Keogh et al. |
| 7,510,536 B2 | 3/2009 | Foley et al. |
| 7,517,315 B2 | 4/2009 | Willis |
| 7,530,356 B2 | 5/2009 | Slayton |
| 7,530,958 B2 | 5/2009 | Slayton |
| 7,532,201 B2 | 5/2009 | Quistgaard et al. |
| 7,571,336 B2 | 8/2009 | Barthe |
| 7,601,120 B2 | 10/2009 | Moilanen et al. |
| 7,615,015 B2 | 11/2009 | Coleman |
| 7,615,016 B2 | 11/2009 | Barthe |
| 7,631,611 B1 | 12/2009 | Dick et al. |
| 7,652,411 B2 | 1/2010 | Crunkilton et al. |
| 7,662,114 B2 | 2/2010 | Seip et al. |
| 7,674,257 B2 | 3/2010 | Pless et al. |
| 7,686,763 B2 | 3/2010 | Vaezy et al. |
| 7,713,203 B2 | 3/2010 | Lacoste et al. |
| 7,694,406 B2 | 4/2010 | Wildes et al. |
| 7,695,437 B2 | 4/2010 | Quistgaard et al. |
| 7,727,156 B2 | 6/2010 | Angelsen et al. |
| 7,758,524 B2 | 7/2010 | Barthe |
| 7,766,848 B2 | 8/2010 | Desilets et al. |
| 7,789,841 B2 | 9/2010 | Huckle et al. |
| 7,806,839 B2 | 10/2010 | Mast et al. |
| 7,815,570 B2 | 10/2010 | Eshel et al. |
| 7,819,826 B2 | 10/2010 | Diederich et al. |
| 7,828,734 B2 | 10/2010 | Azhari et al. |
| 7,824,348 B2 | 11/2010 | Barthe |
| 7,833,162 B2 | 11/2010 | Hasegawa et al. |
| 7,841,984 B2 | 11/2010 | Cribbs et al. |
| 7,846,096 B2 | 12/2010 | Mast et al. |
| 7,857,773 B2 | 12/2010 | Desilets et al. |
| 7,875,023 B2 | 1/2011 | Eshel et al. |
| 7,901,359 B2 | 3/2011 | Mandrusov et al. |
| 7,905,007 B2 | 3/2011 | Calisti et al. |
| 7,905,844 B2 | 3/2011 | Desilets et al. |
| 7,914,453 B2 | 3/2011 | Slayton et al. |
| 7,914,469 B2 | 3/2011 | Torbati |
| 7,967,764 B2 | 6/2011 | Lidgren et al. |
| 7,967,839 B2 | 6/2011 | Flock et al. |
| 7,955,262 B2 | 7/2011 | Rosenberg |
| 7,993,289 B2 | 8/2011 | Quistgaard et al. |
| 8,057,465 B2 | 9/2011 | Sliwa, Jr. et al. |
| 8,057,389 B2 | 11/2011 | Barthe et al. |
| 8,066,641 B2 | 11/2011 | Barthe et al. |
| 8,123,707 B2 | 2/2012 | Huckle et al. |
| 8,128,618 B2 | 3/2012 | Gliklich et al. |
| 8,133,180 B2 | 3/2012 | Slayton et al. |
| 8,133,191 B2 | 3/2012 | Rosenberg et al. |
| 8,142,200 B2 | 3/2012 | Crunkilton et al. |
| 8,152,904 B2 | 4/2012 | Slobodzian et al. |
| 8,162,858 B2 | 4/2012 | Manna et al. |
| 8,166,332 B2 | 4/2012 | Barthe et al. |
| 8,182,428 B2 | 5/2012 | Angelsen et al. |
| 8,197,409 B2 | 6/2012 | Foley et al. |
| 8,206,299 B2 | 6/2012 | Foley et al. |
| 8,208,346 B2 | 6/2012 | Crunkilton |
| 8,211,017 B2 | 7/2012 | Foley et al. |
| 8,262,591 B2 | 9/2012 | Pedersen et al. |
| 8,262,650 B2 | 9/2012 | Zanelli et al. |
| 8,264,126 B2 | 9/2012 | Toda et al. |
| 8,273,037 B2 | 9/2012 | Kreindel et al. |
| 8,282,554 B2 | 10/2012 | Makin et al. |
| 8,292,835 B1 | 10/2012 | Cimino |
| 8,298,163 B1 | 10/2012 | Cimino |
| 8,333,700 B1 | 12/2012 | Barthe et al. |
| 8,334,637 B2 | 12/2012 | Crunkilton et al. |
| 8,337,407 B2 | 12/2012 | Quistgaard et al. |
| 8,343,051 B2 | 1/2013 | Desilets et al. |
| 8,454,540 B2 | 1/2013 | Eshel et al. |
| 8,366,622 B2 | 2/2013 | Slayton et al. |
| 8,398,549 B2 | 3/2013 | Palmeri et al. |
| 8,409,097 B2 | 4/2013 | Slayton et al. |
| 8,425,435 B2 | 4/2013 | Wing et al. |
| 8,388,535 B2 | 5/2013 | Weng et al. |
| 8,444,562 B2 | 5/2013 | Barthe et al. |
| 8,460,193 B2 | 6/2013 | Barthe et al. |
| 8,480,585 B2 | 7/2013 | Slayton et al. |
| 8,486,001 B2 | 7/2013 | Weyant |
| 8,506,486 B2 | 8/2013 | Slayton et al. |
| 8,512,250 B2 | 8/2013 | Quistgaard et al. |
| 8,523,775 B2 | 9/2013 | Barthe et al. |
| 8,523,849 B2 | 9/2013 | Liu et al. |
| 8,535,228 B2 | 9/2013 | Slayton et al. |
| 8,570,837 B2 | 10/2013 | Toda et al. |
| 8,573,392 B2 | 11/2013 | Bennett et al. |
| 8,583,211 B2 | 11/2013 | Salomir et al. |
| 8,585,618 B2 | 11/2013 | Hunziker et al. |
| 8,604,672 B2 | 12/2013 | Toda et al. |
| 8,622,937 B2 | 1/2014 | Weng et al. |
| 8,636,665 B2 | 1/2014 | Slayton et al. |
| 8,640,193 B2 | 1/2014 | Shigeeda |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,708,935 B2 | 4/2014 | Barthe et al. |
| 8,715,186 B2 | 5/2014 | Slayton et al. |
| 8,726,781 B2 | 5/2014 | Eckhoff et al. |
| 8,728,071 B2 | 5/2014 | Lischinsky et al. |
| 8,753,295 B2 | 6/2014 | Thierman |
| 8,758,253 B2 | 6/2014 | Sano et al. |
| 8,836,203 B2 | 9/2014 | Nobles et al. |
| 8,857,438 B2 | 10/2014 | Barthe et al. |
| 8,858,471 B2 | 10/2014 | Barthe et al. |
| 8,915,853 B2 | 12/2014 | Barthe et al. |
| 8,915,854 B2 | 12/2014 | Slayton et al. |
| 8,915,870 B2 | 12/2014 | Barthe et al. |
| 8,920,320 B2 | 12/2014 | Stecco et al. |
| 8,920,324 B2 | 12/2014 | Slayton et al. |
| 8,926,533 B2 | 1/2015 | Bockenstedt et al. |

(56) References Cited

U.S. PATENT DOCUMENTS

| | | | |
|---|---|---|---|
| 8,932,224 B2 | 1/2015 | Barthe et al. |
| 8,932,238 B2 | 1/2015 | Wing et al. |
| 8,968,205 B2 | 3/2015 | Zeng et al. |
| 9,011,336 B2 | 4/2015 | Slayton et al. |
| 9,039,617 B2 | 5/2015 | Slayton et al. |
| 9,039,619 B2 | 5/2015 | Barthe et al. |
| 9,050,116 B2 | 6/2015 | Homer |
| 9,095,697 B2 | 8/2015 | Barthe et al. |
| 9,107,798 B2 | 8/2015 | Azhari et al. |
| 9,114,247 B2 | 8/2015 | Barthe et al. |
| 9,180,314 B2 | 11/2015 | Desilets et al. |
| 9,216,276 B2 | 12/2015 | Slayton et al. |
| 9,220,915 B2 | 12/2015 | Liu et al. |
| 9,272,162 B2 | 3/2016 | Slayton et al. |
| 9,283,409 B2 | 3/2016 | Slayton et al. |
| 9,283,410 B2 | 3/2016 | Slayton et al. |
| 9,295,607 B2 | 3/2016 | Rosenberg |
| 9,308,390 B2 | 4/2016 | Youngquist |
| 9,308,391 B2 | 4/2016 | Liu et al. |
| 9,314,650 B2 | 4/2016 | Rosenberg et al. |
| 9,320,537 B2 | 4/2016 | Slayton et al. |
| 9,345,910 B2 | 5/2016 | Slayton et al. |
| 9,421,029 B2 | 8/2016 | Barthe et al. |
| 9,427,600 B2 | 8/2016 | Barthe et al. |
| 9,427,601 B2 | 8/2016 | Barthe et al. |
| 9,433,803 B2 | 9/2016 | Lin et al. |
| 9,440,093 B2 | 9/2016 | Homer |
| 9,440,096 B2 | 9/2016 | Barthe et al. |
| 9,492,645 B2 | 11/2016 | Zhou et al. |
| 9,492,686 B2 | 11/2016 | Da Silva |
| 9,498,651 B2 | 11/2016 | Sapozhnikov et al. |
| 9,510,802 B2 | 12/2016 | Barthe et al. |
| 9,522,290 B2 | 12/2016 | Slayton et al. |
| 9,532,832 B2 | 1/2017 | Ron Edoute et al. |
| 9,533,174 B2 | 1/2017 | Barthe et al. |
| 9,533,175 B2 | 1/2017 | Slayton et al. |
| 9,545,529 B2 | 1/2017 | Britva et al. |
| 9,566,454 B2 | 2/2017 | Barthe et al. |
| 9,623,267 B2 | 4/2017 | Ulric et al. |
| 9,694,211 B2 | 7/2017 | Barthe et al. |
| 9,694,212 B2 | 7/2017 | Barthe et al. |
| 9,700,340 B2 | 7/2017 | Barthe et al. |
| 9,707,412 B2 | 7/2017 | Slayton et al. |
| 9,710,607 B2 | 7/2017 | Ramdas et al. |
| 9,713,731 B2 | 7/2017 | Slayton et al. |
| 9,802,063 B2 | 10/2017 | Barthe et al. |
| 9,827,449 B2 | 11/2017 | Barthe et al. |
| 9,827,450 B2 | 11/2017 | Slayton et al. |
| 9,833,639 B2 | 12/2017 | Slayton et al. |
| 9,833,640 B2 | 12/2017 | Barthe et al. |
| 9,895,560 B2 | 2/2018 | Barthe et al. |
| 9,907,535 B2 | 3/2018 | Barthe et al. |
| 9,919,167 B2 | 3/2018 | Domankevitz |
| 9,974,982 B2 | 5/2018 | Slayton et al. |
| 1,001,072 A1 | 7/2018 | Slayton et al. |
| 1,004,618 A1 | 8/2018 | Barthe et al. |
| 2001/0009997 A1 | 7/2001 | Pope |
| 2001/0009999 A1 | 7/2001 | Kaufman et al. |
| 2001/0014780 A1 | 8/2001 | Martin et al. |
| 2001/0014819 A1 | 8/2001 | Ingle |
| 2001/0031922 A1 | 10/2001 | Weng |
| 2001/0039380 A1 | 11/2001 | Larson et al. |
| 2001/0041880 A1 | 11/2001 | Brisken |
| 2002/0000763 A1 | 1/2002 | Jones |
| 2002/0002345 A1 | 1/2002 | Marlinghaus |
| 2002/0040199 A1 | 4/2002 | Klopotek |
| 2002/0040442 A1 | 4/2002 | Ishidera |
| 2002/0055702 A1 | 5/2002 | Atala |
| 2002/0062077 A1 | 5/2002 | Emmenegger et al. |
| 2002/0062142 A1 | 5/2002 | Knowlton |
| 2002/0072691 A1 | 6/2002 | Thompson et al. |
| 2002/0082528 A1 | 6/2002 | Friedman et al. |
| 2002/0082529 A1 | 6/2002 | Suorsa et al. |
| 2002/0082589 A1 | 6/2002 | Friedman et al. |
| 2002/0087080 A1 | 7/2002 | Slayton |
| 2002/0095143 A1 | 7/2002 | Key |
| 2002/0099094 A1 | 7/2002 | Anderson |
| 2002/0115917 A1 | 8/2002 | Honda et al. |
| 2002/0128639 A1 | 8/2002 | Pless et al. |
| 2002/0128648 A1 | 9/2002 | Weber |
| 2002/0143252 A1* | 10/2002 | Dunne et al. ................. 600/437 |
| 2002/0156400 A1 | 10/2002 | Babaev |
| 2002/0161357 A1 | 10/2002 | Anderson |
| 2002/0165529 A1 | 11/2002 | Danek |
| 2002/0168049 A1 | 11/2002 | Schriever |
| 2002/0169394 A1 | 11/2002 | Eppstein et al. |
| 2002/0169442 A1 | 11/2002 | Neev |
| 2002/0173721 A1 | 11/2002 | Grunwald et al. |
| 2002/0193784 A1 | 12/2002 | McHale et al. |
| 2002/0193831 A1 | 12/2002 | Smith |
| 2003/0009153 A1 | 1/2003 | Brisken et al. |
| 2003/0014039 A1 | 1/2003 | Barzell et al. |
| 2003/0018255 A1 | 1/2003 | Martin |
| 2003/0018270 A1 | 1/2003 | Makin et al. |
| 2003/0023283 A1 | 1/2003 | McDaniel |
| 2003/0028111 A1 | 2/2003 | Vaezy et al. |
| 2003/0028113 A1 | 2/2003 | Gilbert et al. |
| 2003/0032900 A1 | 2/2003 | Ella |
| 2003/0036706 A1 | 2/2003 | Slayton et al. |
| 2003/0040739 A1 | 2/2003 | Koop |
| 2003/0050678 A1 | 3/2003 | Sierra |
| 2003/0055308 A1 | 3/2003 | Friemel et al. |
| 2003/0055417 A1 | 3/2003 | Truckai et al. |
| 2003/0060736 A1 | 3/2003 | Martin et al. |
| 2003/0040442 A1 | 4/2003 | Ishidera |
| 2003/0065313 A1 | 4/2003 | Koop |
| 2003/0066708 A1 | 4/2003 | Allison et al. |
| 2003/0073907 A1 | 4/2003 | Taylor |
| 2003/0074023 A1 | 4/2003 | Kaplan |
| 2003/0083536 A1 | 5/2003 | Eshel |
| 2003/0092988 A1 | 5/2003 | Makin |
| 2003/0097071 A1 | 5/2003 | Heimann et al. |
| 2003/0099383 A1 | 5/2003 | Lefebvre |
| 2003/0125629 A1 | 7/2003 | Ustuner |
| 2003/0135135 A1 | 7/2003 | Miwa et al. |
| 2003/0139790 A1 | 7/2003 | Ingle et al. |
| 2003/0149366 A1 | 8/2003 | Stringer et al. |
| 2003/0153961 A1 | 8/2003 | Babaev |
| 2003/0171678 A1 | 9/2003 | Batten et al. |
| 2003/0171701 A1* | 9/2003 | Babaev ............................ 601/3 |
| 2003/0176790 A1 | 9/2003 | Slayton |
| 2003/0191396 A1 | 10/2003 | Sanghvi |
| 2003/0199794 A1 | 10/2003 | Sakurai et al. |
| 2003/0200481 A1 | 10/2003 | Stanley |
| 2003/0212129 A1 | 11/2003 | Liu et al. |
| 2003/0212351 A1 | 11/2003 | Hissong |
| 2003/0212393 A1 | 11/2003 | Knowlton |
| 2003/0216648 A1 | 11/2003 | Lizzi et al. |
| 2003/0216795 A1 | 11/2003 | Harth |
| 2003/0220536 A1 | 11/2003 | Hissong |
| 2003/0220585 A1 | 11/2003 | Hissong |
| 2003/0229331 A1 | 12/2003 | Brisken et al. |
| 2003/0233085 A1 | 12/2003 | Giammarusti |
| 2003/0236487 A1 | 12/2003 | Knowlton |
| 2004/0000316 A1 | 1/2004 | Knowlton |
| 2004/0001809 A1 | 1/2004 | Brisken |
| 2004/0002658 A1 | 1/2004 | Marian, Jr. |
| 2004/0002705 A1 | 1/2004 | Knowlton |
| 2004/0010222 A1 | 1/2004 | Nunomura et al. |
| 2004/0015079 A1 | 1/2004 | Berger et al. |
| 2004/0015106 A1 | 1/2004 | Coleman |
| 2004/0030227 A1 | 2/2004 | Littrup |
| 2004/0030268 A1 | 2/2004 | Weng et al. |
| 2004/0039312 A1 | 2/2004 | Hillstead |
| 2004/0039418 A1 | 2/2004 | Elstrom |
| 2004/0041563 A1 | 3/2004 | Lewin et al. |
| 2004/0041880 A1 | 3/2004 | Ikeda et al. |
| 2004/0042168 A1 | 3/2004 | Yang et al. |
| 2004/0044375 A1 | 3/2004 | Diederich et al. |
| 2004/0049134 A1 | 3/2004 | Tosaya et al. |
| 2004/0049734 A1 | 3/2004 | Tosaya et al. |
| 2004/0059266 A1 | 3/2004 | Fry |
| 2004/0068186 A1 | 4/2004 | Ishida et al. |
| 2004/0073079 A1 | 4/2004 | Altshuler et al. |

(56) References Cited

U.S. PATENT DOCUMENTS

| | | |
|---|---|---|
| 2004/0073113 A1 | 4/2004 | Salgo |
| 2004/0073115 A1 | 4/2004 | Horzewski et al. |
| 2004/0073116 A1 | 4/2004 | Smith |
| 2004/0073204 A1 | 4/2004 | Ryan et al. |
| 2004/0077977 A1 | 4/2004 | Ella et al. |
| 2004/0082857 A1 | 4/2004 | Schonenberger et al. |
| 2004/0082859 A1 | 4/2004 | Schaer |
| 2004/0102697 A1 | 5/2004 | Evron |
| 2004/0105559 A1 | 6/2004 | Aylward et al. |
| 2004/0106867 A1 | 6/2004 | Eshel et al. |
| 2004/0122323 A1 | 6/2004 | Vortman et al. |
| 2004/0122493 A1 | 6/2004 | Ishibashi et al. |
| 2004/0143297 A1 | 7/2004 | Ramsey |
| 2004/0152982 A1 | 8/2004 | Hwang et al. |
| 2004/0158150 A1 | 8/2004 | Rabiner et al. |
| 2004/0186535 A1 | 9/2004 | Knowlton |
| 2004/0189155 A1 | 9/2004 | Funakubo |
| 2004/0206365 A1 | 10/2004 | Knowlton |
| 2004/0210214 A1 | 10/2004 | Knowlton |
| 2004/0217675 A1 | 11/2004 | Desilets |
| 2004/0249318 A1 | 12/2004 | Tanaka |
| 2004/0254620 A1 | 12/2004 | Lacoste |
| 2004/0267252 A1 | 12/2004 | Washington et al. |
| 2005/0033201 A1 | 2/2005 | Takahashi |
| 2005/0033316 A1 | 2/2005 | Kertz |
| 2005/0038340 A1 | 2/2005 | Vaezy et al. |
| 2005/0055018 A1 | 3/2005 | Kreindel |
| 2005/0055073 A1 | 3/2005 | Weber |
| 2005/0061834 A1 | 3/2005 | Garcia et al. |
| 2005/0070961 A1 | 3/2005 | Maki et al. |
| 2005/0074407 A1 | 4/2005 | Smith |
| 2005/0080469 A1 | 4/2005 | Larson |
| 2005/0085731 A1 | 4/2005 | Miller et al. |
| 2005/0091770 A1 | 5/2005 | Mourad et al. |
| 2005/0096542 A1 | 5/2005 | Weng et al. |
| 2005/0104690 A1 | 5/2005 | Larson et al. |
| 2005/0113689 A1 | 5/2005 | Gritzky |
| 2005/0131302 A1 | 6/2005 | Poland |
| 2005/0137656 A1 | 6/2005 | Malak |
| 2005/0143677 A1 | 6/2005 | Young et al. |
| 2005/0154313 A1 | 7/2005 | Desilets |
| 2005/0154314 A1 | 7/2005 | Quistgaard |
| 2005/0154332 A1 | 7/2005 | Zanelli |
| 2005/0154431 A1 | 7/2005 | Quistgaard et al. |
| 2005/0187495 A1 | 8/2005 | Quistgaard |
| 2005/0191252 A1 | 9/2005 | Mitsui |
| 2005/0193451 A1 | 9/2005 | Quistgaard |
| 2005/0193820 A1* | 9/2005 | Sheljaskow .......... A61B 8/4461 73/649 |
| 2005/0197681 A1 | 9/2005 | Barolet et al. |
| 2005/0228281 A1 | 10/2005 | Nefos |
| 2005/0240127 A1 | 10/2005 | Seip et al. |
| 2005/0240170 A1 | 10/2005 | Zhang et al. |
| 2005/0251120 A1 | 11/2005 | Anderson et al. |
| 2005/0251125 A1 | 11/2005 | Pless et al. |
| 2005/0256406 A1 | 11/2005 | Barthe |
| 2005/0261584 A1 | 11/2005 | Eshel |
| 2005/0261585 A1 | 11/2005 | Makin et al. |
| 2005/0267454 A1 | 12/2005 | Hissong |
| 2005/0288748 A1 | 12/2005 | Li et al. |
| 2006/0004306 A1 | 1/2006 | Altshuler |
| 2006/0020260 A1 | 1/2006 | Dover et al. |
| 2006/0025756 A1 | 2/2006 | Francischelli |
| 2006/0042201 A1 | 3/2006 | Curry |
| 2006/0058664 A1 | 3/2006 | Barthe |
| 2006/0058671 A1 | 3/2006 | Vitek et al. |
| 2006/0058707 A1 | 3/2006 | Barthe et al. |
| 2006/0058712 A1 | 3/2006 | Altshuler et al. |
| 2006/0074309 A1 | 4/2006 | Bonnefous |
| 2006/0074313 A1 | 4/2006 | Slayton et al. |
| 2006/0074314 A1 | 4/2006 | Slayton |
| 2006/0074355 A1 | 4/2006 | Slayton |
| 2006/0074613 A1* | 4/2006 | Oyama .............. 703/2 |
| 2006/0079816 A1 | 4/2006 | Barthe |
| 2006/0079868 A1 | 4/2006 | Makin |
| 2006/0084891 A1 | 4/2006 | Barthe |
| 2006/0089632 A1 | 4/2006 | Barthe |
| 2006/0089688 A1 | 4/2006 | Panescu |
| 2006/0094988 A1 | 5/2006 | Tosaya |
| 2006/0111744 A1 | 5/2006 | Makin |
| 2006/0116583 A1 | 6/2006 | Ogasawara et al. |
| 2006/0116671 A1 | 6/2006 | Slayton |
| 2006/0122508 A1 | 6/2006 | Slayton |
| 2006/0122509 A1 | 6/2006 | Desilets |
| 2006/0161062 A1 | 7/2006 | Arditi et al. |
| 2006/0184069 A1 | 8/2006 | Vaitekunas |
| 2006/0184071 A1 | 8/2006 | Klopotek |
| 2006/0189972 A1 | 8/2006 | Grossman |
| 2006/0206105 A1 | 9/2006 | Chopra |
| 2006/0224090 A1 | 10/2006 | Ostrovsky et al. |
| 2006/0229514 A1 | 10/2006 | Wiener |
| 2006/0241440 A1 | 10/2006 | Eshel |
| 2006/0241442 A1 | 10/2006 | Barthe |
| 2006/0241470 A1 | 10/2006 | Novak et al. |
| 2006/0241576 A1 | 10/2006 | Diederich et al. |
| 2006/0250046 A1 | 11/2006 | Koizumi et al. |
| 2006/0261584 A1 | 11/2006 | Eshel |
| 2006/0282691 A1 | 12/2006 | Barthe |
| 2006/0291710 A1 | 12/2006 | Wang et al. |
| 2007/0016039 A1 | 1/2007 | Vortman et al. |
| 2007/0032784 A1* | 2/2007 | Gliklich et al. .............. 606/27 |
| 2007/0035201 A1 | 2/2007 | Desilets |
| 2007/0055154 A1 | 3/2007 | Torbati |
| 2007/0055155 A1 | 3/2007 | Owen et al. |
| 2007/0055156 A1 | 3/2007 | Desilets et al. |
| 2007/0065420 A1 | 3/2007 | Johnson |
| 2007/0083120 A1 | 4/2007 | Cain et al. |
| 2007/0087060 A1 | 4/2007 | Dietrich |
| 2007/0088245 A1 | 4/2007 | Babaev et al. |
| 2007/0088346 A1 | 4/2007 | Mirizzi et al. |
| 2007/0161902 A1 | 7/2007 | Dan |
| 2007/0166357 A1 | 7/2007 | Shaffer et al. |
| 2007/0167709 A1 | 7/2007 | Slayton |
| 2007/0208253 A1 | 9/2007 | Slayton |
| 2007/0219604 A1 | 9/2007 | Yaroslaysky et al. |
| 2007/0219605 A1 | 9/2007 | Yaroslaysky et al. |
| 2007/0238994 A1 | 10/2007 | Stecco et al. |
| 2007/0239075 A1 | 10/2007 | Rosenberg |
| 2007/0239077 A1 | 10/2007 | Azhari et al. |
| 2007/0239079 A1 | 10/2007 | Manstein et al. |
| 2007/0239142 A1 | 10/2007 | Altshuler |
| 2008/0015435 A1 | 1/2008 | Cribbs et al. |
| 2008/0027328 A1 | 1/2008 | Klopotek |
| 2008/0033458 A1* | 2/2008 | McLean .............. A61F 2/0063 606/144 |
| 2008/0039724 A1 | 2/2008 | Seip et al. |
| 2008/0071255 A1 | 3/2008 | Barthe |
| 2008/0366220 | 3/2008 | Makin et al. |
| 2008/0086054 A1 | 4/2008 | Slayton |
| 2008/0086056 A1 | 4/2008 | Chang et al. |
| 2008/0097214 A1* | 4/2008 | Meyers .............. A61B 8/10 600/459 |
| 2008/0097253 A1 | 4/2008 | Pedersen et al. |
| 2008/0114251 A1 | 5/2008 | Weymer |
| 2008/0139943 A1 | 6/2008 | Deng et al. |
| 2008/0139974 A1 | 6/2008 | Da Silva |
| 2008/0146970 A1 | 6/2008 | Litman et al. |
| 2008/0167556 A1 | 7/2008 | Thompson |
| 2008/0183077 A1 | 7/2008 | Moreau-Gobard et al. |
| 2008/0183110 A1 | 7/2008 | Davenport et al. |
| 2008/0188745 A1 | 8/2008 | Chen et al. |
| 2008/0194964 A1* | 8/2008 | Randall et al. .............. 600/459 |
| 2008/0195000 A1 | 8/2008 | Spooner et al. |
| 2008/0200810 A1 | 8/2008 | Buchalter |
| 2008/0214966 A1 | 9/2008 | Slayton |
| 2008/0214988 A1 | 9/2008 | Altshuler et al. |
| 2008/0221491 A1 | 9/2008 | Slayton |
| 2008/0223379 A1 | 9/2008 | Stuker et al. |
| 2008/0242991 A1 | 10/2008 | Moon et al. |
| 2008/0243035 A1 | 10/2008 | Crunkilton |
| 2008/0269608 A1 | 10/2008 | Anderson et al. |
| 2008/0275342 A1 | 11/2008 | Barthe |
| 2008/0281206 A1 | 11/2008 | Bartlett et al. |
| 2008/0281236 A1 | 11/2008 | Eshel et al. |

(56) References Cited

U.S. PATENT DOCUMENTS

| | | |
|---|---|---|
| 2008/0281237 A1 | 11/2008 | Slayton |
| 2008/0281255 A1 | 11/2008 | Slayton |
| 2008/0294073 A1 | 11/2008 | Barthe |
| 2008/0319356 A1 | 12/2008 | Cain |
| 2009/0005680 A1 | 1/2009 | Jones et al. |
| 2009/0012394 A1 | 1/2009 | Hobelsberger et al. |
| 2009/0043198 A1 | 2/2009 | Milner et al. |
| 2009/0043293 A1 | 2/2009 | Pankratov et al. |
| 2009/0048514 A1 | 2/2009 | Azhari et al. |
| 2009/0069677 A1 | 3/2009 | Chen et al. |
| 2009/0093737 A1 | 4/2009 | Chomas et al. |
| 2009/0156969 A1 | 6/2009 | Santangelo |
| 2009/0163807 A1 | 6/2009 | Sliwa |
| 2009/0171252 A1 | 7/2009 | Bockenstedt et al. |
| 2009/0177122 A1 | 7/2009 | Peterson |
| 2009/0177123 A1 | 7/2009 | Peterson |
| 2009/0182231 A1 | 7/2009 | Barthe et al. |
| 2009/0198157 A1 | 8/2009 | Babaev et al. |
| 2009/0216159 A1 | 8/2009 | Slayton et al. |
| 2009/0226424 A1 | 9/2009 | Hsu |
| 2009/0227910 A1 | 9/2009 | Pedersen et al. |
| 2009/0230823 A1 | 9/2009 | Kushculey et al. |
| 2009/0253988 A1 | 10/2009 | Slayton et al. |
| 2009/0281463 A1 | 11/2009 | Chapelon et al. |
| 2009/0312693 A1 | 12/2009 | Thapliyal et al. |
| 2009/0318909 A1 | 12/2009 | Debenedictis et al. |
| 2009/0326420 A1 | 12/2009 | Moonen et al. |
| 2010/0011236 A1 | 1/2010 | Barthe et al. |
| 2010/0022919 A1 | 1/2010 | Peterson |
| 2010/0022921 A1 | 1/2010 | Seip et al. |
| 2010/0022922 A1 | 1/2010 | Barthe et al. |
| 2010/0030076 A1 | 2/2010 | Vortman et al. |
| 2010/0042020 A1 | 2/2010 | Ben-Ezra |
| 2010/0049178 A1 | 2/2010 | Deem et al. |
| 2010/0056925 A1 | 3/2010 | Zhang et al. |
| 2010/0100014 A1 | 4/2010 | Eshel et al. |
| 2010/0113983 A1 | 5/2010 | Heckerman et al. |
| 2010/0130891 A1 | 5/2010 | Taggart et al. |
| 2010/0160782 A1 | 6/2010 | Slayton et al. |
| 2010/0160837 A1 | 6/2010 | Hunziker et al. |
| 2010/0168576 A1 | 7/2010 | Poland et al. |
| 2010/0191120 A1 | 7/2010 | Kraus et al. |
| 2010/0241035 A1 | 9/2010 | Barthe et al. |
| 2010/0249602 A1 | 9/2010 | Buckley et al. |
| 2010/0249669 A1 | 9/2010 | Ulric et al. |
| 2010/0256489 A1 | 10/2010 | Pedersen et al. |
| 2010/0274161 A1 | 10/2010 | Azhari et al. |
| 2010/0280420 A1 | 11/2010 | Barthe et al. |
| 2010/0286518 A1 | 11/2010 | Lee et al. |
| 2010/0312150 A1 | 12/2010 | Douglas et al. |
| 2011/0040171 A1 | 2/2011 | Foley et al. |
| 2011/0040190 A1 | 2/2011 | Jahnke et al. |
| 2011/0040213 A1 | 2/2011 | Dietz et al. |
| 2011/0040214 A1 | 2/2011 | Foley et al. |
| 2011/0066084 A1 | 3/2011 | Desilets et al. |
| 2011/0077514 A1 | 3/2011 | Ulric et al. |
| 2011/0087099 A1 | 4/2011 | Eshel et al. |
| 2011/0087255 A1 | 4/2011 | McCormack et al. |
| 2011/0144490 A1 | 6/2011 | Davis et al. |
| 2011/0178444 A1 | 7/2011 | Slayton et al. |
| 2011/0178541 A1 | 7/2011 | Azhari |
| 2011/0190745 A1 | 8/2011 | Uebelhoer et al. |
| 2011/0201976 A1 | 8/2011 | Sanghvi et al. |
| 2011/0251524 A1 | 10/2011 | Azhari et al. |
| 2011/0251527 A1 | 10/2011 | Kushculey et al. |
| 2011/0270137 A1 | 11/2011 | Goren et al. |
| 2011/0319793 A1 | 12/2011 | Henrik et al. |
| 2011/0319794 A1 | 12/2011 | Gertner |
| 2012/0004549 A1 | 1/2012 | Barthe et al. |
| 2012/0016239 A1 | 1/2012 | Barthe et al. |
| 2012/0029353 A1 | 2/2012 | Slayton et al. |
| 2012/0035473 A1 | 2/2012 | Sanghvi et al. |
| 2012/0035475 A1 | 2/2012 | Barthe et al. |
| 2012/0035476 A1 | 2/2012 | Barthe et al. |
| 2012/0046547 A1 | 2/2012 | Barthe et al. |
| 2012/0053458 A1 | 3/2012 | Barthe et al. |
| 2012/0059288 A1 | 3/2012 | Barthe et al. |
| 2012/0111339 A1 | 5/2012 | Barthe et al. |
| 2012/0123304 A1 | 5/2012 | Rybyanets et al. |
| 2012/0136280 A1 | 5/2012 | Rosenberg et al. |
| 2012/0136282 A1 | 5/2012 | Rosenberg et al. |
| 2012/0143056 A1 | 6/2012 | Slayton et al. |
| 2012/0143100 A1 | 6/2012 | Jeong et al. |
| 2012/0165668 A1 | 6/2012 | Slayton et al. |
| 2012/0165848 A1 | 6/2012 | Slayton et al. |
| 2012/0191019 A1 | 7/2012 | Desilets et al. |
| 2012/0191020 A1 | 7/2012 | Vitek et al. |
| 2012/0197120 A1 | 8/2012 | Makin et al. |
| 2012/0197121 A1 | 8/2012 | Slayton et al. |
| 2012/0209150 A1 | 8/2012 | Zeng et al. |
| 2012/0215105 A1 | 8/2012 | Slayton et al. |
| 2012/0271202 A1 | 10/2012 | Wisdom |
| 2012/0271294 A1 | 10/2012 | Barthe et al. |
| 2012/0296240 A1 | 11/2012 | Azhari et al. |
| 2012/0302883 A1 | 11/2012 | Kong et al. |
| 2012/0316426 A1 | 12/2012 | Foley et al. |
| 2012/0330197 A1 | 12/2012 | Makin et al. |
| 2012/0330222 A1 | 12/2012 | Makin et al. |
| 2012/0330223 A1 | 12/2012 | Makin et al. |
| 2012/0330283 A1 | 12/2012 | Hyde et al. |
| 2012/0330284 A1 | 12/2012 | Hyde et al. |
| 2013/0012755 A1 | 1/2013 | Slayton |
| 2013/0012816 A1 | 1/2013 | Slayton et al. |
| 2013/0012838 A1 | 1/2013 | Jaeger et al. |
| 2013/0012842 A1 | 1/2013 | Barthe |
| 2013/0018285 A1 | 1/2013 | Park et al. |
| 2013/0018286 A1 | 1/2013 | Slayton et al. |
| 2013/0046209 A1 | 2/2013 | Slayton et al. |
| 2013/0051178 A1 | 2/2013 | Rybyanets |
| 2013/0060170 A1 | 3/2013 | Lee et al. |
| 2013/0066208 A1 | 3/2013 | Barthe et al. |
| 2013/0066237 A1 | 3/2013 | Smotrich et al. |
| 2013/0072826 A1 | 3/2013 | Slayton et al. |
| 2013/0073001 A1 | 3/2013 | Campbell |
| 2013/0096471 A1 | 4/2013 | Slayton et al. |
| 2013/0190659 A1 | 7/2013 | Slayton et al. |
| 2013/0211293 A1 | 8/2013 | Auboiroux et al. |
| 2013/0225994 A1 | 8/2013 | Hsu et al. |
| 2013/0268032 A1 | 10/2013 | Neev |
| 2013/0274603 A1 | 10/2013 | Barthe et al. |
| 2013/0281853 A1 | 10/2013 | Slayton et al. |
| 2013/0281891 A1 | 10/2013 | Slayton et al. |
| 2013/0296697 A1 | 11/2013 | Slayton et al. |
| 2013/0296700 A1 | 11/2013 | Slayton et al. |
| 2013/0296743 A1 | 11/2013 | Lee et al. |
| 2013/0303904 A1 | 11/2013 | Barthe et al. |
| 2013/0303905 A1 | 11/2013 | Barthe et al. |
| 2013/0310714 A1 | 11/2013 | Eshel et al. |
| 2013/0310863 A1 | 11/2013 | Makin et al. |
| 2013/0345562 A1 | 12/2013 | Barthe et al. |
| 2014/0024974 A1 | 1/2014 | Slayton et al. |
| 2014/0050054 A1 | 2/2014 | Toda et al. |
| 2014/0081300 A1 | 3/2014 | Melodelima et al. |
| 2014/0082907 A1 | 3/2014 | Barthe et al. |
| 2014/0117814 A1 | 5/2014 | Toda et al. |
| 2014/0142430 A1 | 5/2014 | Slayton et al. |
| 2014/0148834 A1 | 5/2014 | Barthe et al. |
| 2014/0180174 A1 | 6/2014 | Slayton et al. |
| 2014/0187944 A1 | 7/2014 | Slayton et al. |
| 2014/0188015 A1 | 7/2014 | Slayton et al. |
| 2014/0188145 A1 | 7/2014 | Slayton et al. |
| 2014/0194723 A1 | 7/2014 | Herzog et al. |
| 2014/0208856 A1 | 7/2014 | Schmid |
| 2014/0221823 A1 | 8/2014 | Keogh et al. |
| 2014/0236049 A1 | 8/2014 | Barthe et al. |
| 2014/0236061 A1 | 8/2014 | Lee et al. |
| 2014/0243713 A1 | 8/2014 | Slayton et al. |
| 2014/0257145 A1 | 9/2014 | Emery |
| 2014/0276055 A1 | 9/2014 | Barthe et al. |
| 2015/0000674 A1 | 1/2015 | Barthe et al. |
| 2015/0025420 A1 | 1/2015 | Slayton et al. |
| 2015/0080723 A1 | 3/2015 | Barthe et al. |
| 2015/0080771 A1 | 3/2015 | Barthe et al. |
| 2015/0080874 A1 | 3/2015 | Slayton et al. |

(56) References Cited

U.S. PATENT DOCUMENTS

| | | |
|---|---|---|
| 2015/0088182 A1 | 3/2015 | Slayton et al. |
| 2015/0141734 A1 | 5/2015 | Chapelon et al. |
| 2015/0164734 A1 | 6/2015 | Slayton et al. |
| 2015/0165238 A1 | 6/2015 | Slayton et al. |
| 2015/0165243 A1 | 6/2015 | Slayton et al. |
| 2015/0174388 A1 | 6/2015 | Slayton |
| 2015/0202468 A1 | 7/2015 | Slayton et al. |
| 2015/0217141 A1 | 8/2015 | Barthe et al. |
| 2015/0238258 A1 | 8/2015 | Palero et al. |
| 2015/0321026 A1 | 11/2015 | Branson et al. |
| 2015/0360058 A1 | 12/2015 | Barthe et al. |
| 2015/0374333 A1 | 12/2015 | Barthe et al. |
| 2015/0375014 A1 | 12/2015 | Slayton et al. |
| 2016/0001097 A1 | 1/2016 | Cho et al. |
| 2016/0016015 A1 | 1/2016 | Slayton et al. |
| 2016/0027994 A1 | 1/2016 | Toda et al. |
| 2016/0151618 A1 | 6/2016 | Powers et al. |
| 2016/0175619 A1 | 6/2016 | Lee et al. |
| 2016/0206335 A1 | 7/2016 | Slayton |
| 2016/0206341 A1 | 7/2016 | Slayton |
| 2016/0256675 A1 | 9/2016 | Slayton |
| 2016/0296769 A1 | 10/2016 | Barthe et al. |
| 2016/0361571 A1 | 12/2016 | Bernabei |
| 2016/0361572 A1 | 12/2016 | Slayton |
| 2017/0028227 A1 | 2/2017 | Emery et al. |
| 2017/0043190 A1 | 2/2017 | Barthe et al. |
| 2017/0050019 A1 | 2/2017 | Ron Edoute et al. |
| 2017/0080257 A1 | 3/2017 | Paunescu et al. |
| 2017/0100585 A1 | 4/2017 | Hall et al. |
| 2017/0136263 A1 | 5/2017 | Reil |
| 2017/0209201 A1 | 7/2017 | Slayton et al. |
| 2017/0304654 A1 | 10/2017 | Blanche et al. |
| 2018/0001113 A1 | 1/2018 | Streeter |
| 2018/0015308 A1 | 1/2018 | Reed et al. |
| 2018/0043147 A1 | 2/2018 | Slayton |
| 2018/0099162 A1 | 4/2018 | Bernabei |
| 2018/0099163 A1 | 4/2018 | Bernabei |
| 2018/0272156 A1 | 9/2018 | Slayton et al. |
| 2018/0272157 A1 | 9/2018 | Barthe et al. |
| 2018/0272158 A1 | 9/2018 | Barthe et al. |
| 2018/0272159 A1 | 9/2018 | Slayton et al. |

FOREIGN PATENT DOCUMENTS

| | | |
|---|---|---|
| DE | 10140064 A1 | 3/2003 |
| DE | 10219217 | 11/2003 |
| DE | 10219297 | 11/2003 |
| DE | 20314479 | 3/2004 |
| EP | 0142215 | 5/1984 |
| EP | 0344773 A2 | 12/1989 |
| EP | 1479412 A1 | 11/1991 |
| EP | 0473553 | 4/1992 |
| EP | 670147 | 2/1995 |
| EP | 0661029 A1 | 7/1995 |
| EP | 724894 | 2/1996 |
| EP | 763371 | 11/1996 |
| EP | 1044038 | 10/2000 |
| EP | 1050322 A1 | 11/2000 |
| EP | 1234566 | 8/2002 |
| EP | 1262160 | 12/2002 |
| EP | 0659387 | 4/2003 |
| EP | 1374944 | 1/2004 |
| EP | 1028660 | 1/2008 |
| EP | 1874241 | 1/2008 |
| EP | 1362223 | 5/2008 |
| EP | 1750804 | 7/2008 |
| EP | 1283690 | 11/2008 |
| EP | 1811901 | 4/2009 |
| EP | 1785164 | 8/2009 |
| EP | 2230904 | 9/2010 |
| EP | 1501331 | 6/2011 |
| EP | 2066405 | 11/2011 |
| EP | 2474050 | 7/2012 |
| EP | 2709726 | 11/2015 |
| EP | 1538980 | 1/2017 |
| EP | 2897547 | 11/2017 |
| FR | 2532851 | 9/1983 |
| FR | 2685872 | 1/1992 |
| FR | 2672486 | 8/1992 |
| FR | 2703254 | 3/1994 |
| GB | 2113099 | 8/1983 |
| IL | 102516 | 1/1996 |
| IL | 112369 | 8/1999 |
| IL | 120079 | 3/2001 |
| JP | 63036171 | 2/1988 |
| JP | 03048299 | 3/1991 |
| JP | 3123559 | 5/1991 |
| JP | 3136642 | 6/1991 |
| JP | 4089058 | 3/1992 |
| JP | 4-150847 | 5/1992 |
| JP | 04150847 | 5/1992 |
| JP | 7080087 | 3/1995 |
| JP | 07505793 | 6/1995 |
| JP | 2007505793 | 6/1995 |
| JP | 7184907 | 7/1995 |
| JP | 7222782 | 8/1995 |
| JP | 09047458 | 2/1997 |
| JP | 9108288 | 4/1997 |
| JP | 9503926 | 4/1997 |
| JP | 11-505440 | 5/1999 |
| JP | 11123226 | 5/1999 |
| JP | 11-506636 | 6/1999 |
| JP | 10248850 | 9/1999 |
| JP | 2000126310 | 5/2000 |
| JP | 2000166940 | 6/2000 |
| JP | 2000233009 | 8/2000 |
| JP | 2001170068 | 6/2001 |
| JP | 2002505596 | 2/2002 |
| JP | 2002078764 | 3/2002 |
| JP | 2002515786 | 5/2002 |
| JP | 2002521118 | 7/2002 |
| JP | 2002-537939 | 11/2002 |
| JP | 2003050298 | 2/2003 |
| JP | 2003204982 | 7/2003 |
| JP | 2004-504898 | 2/2004 |
| JP | 2004-507280 | 3/2004 |
| JP | 2004-509671 | 4/2004 |
| JP | 2004-512856 | 4/2004 |
| JP | 2004-147719 | 5/2004 |
| JP | 2005503388 | 2/2005 |
| JP | 2005527336 | 9/2005 |
| JP | 2005323213 | 11/2005 |
| JP | 2006520247 | 9/2006 |
| JP | 2008515559 | 5/2008 |
| JP | 2009518126 | 5/2009 |
| JP | 2010517695 | 5/2010 |
| KR | 1020010024871 | 3/2001 |
| KR | 100400870 | 10/2003 |
| KR | 20060121267 | 11/2006 |
| KR | 1020060113930 | 11/2006 |
| KR | 1020070065332 | 6/2007 |
| KR | 1020070070161 | 7/2007 |
| KR | 1020070098856 | 10/2007 |
| KR | 1020070104878 | 10/2007 |
| KR | 1020070114105 | 11/2007 |
| KR | 1020000059516 | 4/2012 |
| KR | 10-2013-0124598 | 11/2013 |
| KR | 10-1365946 | 2/2014 |
| TW | 386883 | 9/2000 |
| TW | 201208734 A | 3/2012 |
| WO | WO93/12742 | 7/1993 |
| WO | WO95/24159 | 9/1995 |
| WO | WO 96/25888 | 8/1996 |
| WO | WO 96/34568 | 11/1996 |
| WO | WO 96/39079 | 12/1996 |
| WO | WO 9735518 | 10/1997 |
| WO | WO 9832379 | 7/1998 |
| WO | WO9852465 | 11/1998 |
| WO | WO 9933520 | 7/1999 |
| WO | WO9939677 | 8/1999 |
| WO | WO 9949788 | 10/1999 |
| WO | WO 200006032 | 2/2000 |
| WO | WO 0015300 | 3/2000 |
| WO | WO 0021612 | 4/2000 |

(56) References Cited

FOREIGN PATENT DOCUMENTS

| | | |
|---|---|---|
| WO | WO 0053113 | 9/2000 |
| WO | WO 0126823 | 4/2001 |
| WO | WO 01/045550 | 6/2001 |
| WO | WO 01/080709 | 11/2001 |
| WO | WO 0182777 | 11/2001 |
| WO | WO 0182778 | 11/2001 |
| WO | WO 0187161 | 11/2001 |
| WO | WO2001087161 | 11/2001 |
| WO | WO 02/09812 | 2/2002 |
| WO | WO 02/015768 | 2/2002 |
| WO | WO 0209813 | 2/2002 |
| WO | WO 0224050 | 3/2002 |
| WO | WO 02024050 | 3/2002 |
| WO | WO2002054018 | 7/2002 |
| WO | WO 02092168 | 11/2002 |
| WO | WO 03/053266 | 7/2003 |
| WO | WO 03/06547 | 8/2003 |
| WO | WO 03065347 | 8/2003 |
| WO | WO 03070105 | 8/2003 |
| WO | WO 03077833 | 9/2003 |
| WO | WO 03086215 | 10/2003 |
| WO | WO 03/096883 A2 | 11/2003 |
| WO | WO 03/099382 | 12/2003 |
| WO | WO 03099177 | 12/2003 |
| WO | WO 03101530 | 12/2003 |
| WO | WO 2004000116 | 12/2003 |
| WO | WO 2004080147 | 9/2004 |
| WO | WO 2004110558 | 12/2004 |
| WO | WO 2005011804 | 2/2005 |
| WO | WO 2005065408 | 7/2005 |
| WO | WO2005065409 | 7/2005 |
| WO | WO 2005090978 | 9/2005 |
| WO | WO2005113068 | 12/2005 |
| WO | WO 2006036870 | 4/2006 |
| WO | WO 2006042163 | 4/2006 |
| WO | WO 2006042168 | 4/2006 |
| WO | WO 2006042201 | 4/2006 |
| WO | WO 2006065671 | 6/2006 |
| WO | WO 2006082573 | 8/2006 |
| WO | WO2006104568 | 10/2006 |
| WO | WO 2007067563 | 6/2007 |
| WO | WO2008036479 | 3/2008 |
| WO | WO 2008036622 | 3/2008 |
| WO | WO2008144274 | 11/2008 |
| WO | WO2009013729 | 1/2009 |
| WO | WO 2009013729 | 1/2009 |
| WO | WO2009/149390 | 10/2009 |
| WO | WO2012134645 | 10/2012 |
| WO | WO2013048912 | 4/2013 |
| WO | WO2013178830 | 12/2013 |
| WO | WO2014045216 | 3/2014 |
| WO | WO2014/055708 | 4/2014 |
| WO | WO2014057388 | 4/2014 |
| WO | WO2014127091 | 8/2014 |
| WO | WO2015160708 | 10/2015 |
| WO | WO2016054155 | 4/2016 |
| WO | WO2017127328 | 7/2017 |
| WO | WO2017149506 | 9/2017 |
| WO | WO2017165595 | 9/2017 |
| WO | WO2017212489 | 12/2017 |
| WO | WO2018035012 | 2/2018 |

OTHER PUBLICATIONS

Damianou et al., "Application of the Thermal Dose Concept for Predicting the Necrosed Tissue Volume During Ultrasound Surgery," 1993 IEEE Ultrasound Symposium, pp. 1199-1202.

Fry, W.J. et al., "Production of Focal Destructive Lesions in the Central Nervous System with Ultrasound," J. Neurosurg., 11:471-478; 1954.

Harr, G.R. et al., "Tissue Destruction with Focused Ultrasound in Vivo," Eur. Urol. 23 (suppl. 1):8-11; 1993.

Jeffers et al., "Evaluation of the Effect of Cavitation Activity on Drug-Ultrasound Synergisms," 1993 IEEE Ultrasonics Symposium, pp. 925-928.

Madersbacher, S. et al., "Tissue Ablation in Bening Prostatic Hyperplasia with High Intensity Focused Ultrasound," Dur. Urol., 23 (suppl. 1):39-43; 1993.

Saad et al., "Ultrasound-Enhanced Effects of Adriamycin Against Murine Tumors," Ultrasound in Med. & Biol. vol. 18, No. 8, pp. 715-723 (1992).

Simon et al., "Applications of Lipid-Coated Microbubble Ultrasonic Contrast to Tumor Therapy," Ultrasound in Med. & Biol. vol. 19, No. 2, pp. 123-125 (1993).

Tata et al., "Interaction of Ultrasound and Model Membrane Systems: Analyses and Predictions," American Chemical Society, Phys. Chem. 1992, 96, pp. 3548-3555.

International Search Report and Written Opinion in PCT Application No. PCT/US2009/46475 dated Jul. 29, 2009 in 11 pages.

Alster, Tinas S., Tanzi, Elizabeth L., "Cellulite Treatment using a Novel Combination Radiofrequency, Infrared Light, and Mechanical Tissue Manipulation Device," Journal of Cosmetic & Laser Therapy, Jun. 2005, vol. 7, Issue 2, pp. 81-85.

Barthe et al., "Ultrasound therapy system and abiation results utilizing miniature imaging/therapy arrays," Ultrasonics Symposium, 2004 IEEE, Aug. 23, 2004, pp. 1792-1795, vol. 3.

Coon, Joshua et al., "Protein identification using sequential ion/ion reactions and tandem mass spectometry" Proceedings of the National Academy of Sciences of the USA, vol. 102, No. 27, Jul. 27, 2005, pp. 9463-9468.

Corry, Peter M., et al., "Human Cancer Treatment with Ultrasound", IEEE Transactions on Sonics and Ultrasonics, vol. SU-31, No. 5, Sep. 1984, pp. 444, 456.

Daum et al., Abstract, Design and Evaluation of a Feedback Based Phased Array System for Ultrasound Surgery, IEEE Transactions on Ultrasonics, Feroelectronics, and Frequency Control, vol. 45, No. 2, Mar. 1998, pp. 431-438.

Davis, Brian J., et al., "An Acoustic Phase Shift Technique for the Non-Invasive Measurement of Temperature Changes in Tissues", 1985 Ultrasonics Symposium, pp. 921-924.

Gliklich et al., Clinical Pilot Study of Intense Ultrasound therapy to Deep Dermal Facial Skin and Subcutaneous Tissues, Arch Facial Plastic Surgery, Mar. 1, 2007, vol. 9, No. 1.

Hassan et al., "Structure and Applications of Poly(vinyl alcohol) Hydrogels Produced by Conventional Crosslinking or by Freezing/Thawing Methods," advanced in Polymer Science, 2000, pp. 37-65, vol. 153.

Hassan et al., "Structure and Morphology of Freeze/Thawed PVA Hydrogels," Macromolecules, Mar. 11, 2000, pp. 2472-2479, vol. 33, No. 7.

Husseini et al. "Investigating the mechanism of accoustically activated uptake of drugs from Pluronic micelles," BMD Cancer 2002, 2:20k, Aug. 30, 2002, pp. 1-6.

Husseini et al, "The Role of Cavitation in Acoustically Activated Drug Delivery," J. Control Release, Oct. 3, 2005, pp. 253-261, vol. 107(2).

Jenne, J., et al., "Temperature Mapping for High Energy US-Therapy", 1994 Ultrasonics Symposium, pp. 1879-1882.

Johnson, S.A., et al., "Non-Instrusive Measurement of Microwave and Ultrasound-Induced Hyperthermia by Acoustic Temperature Tomography", Ultrasonics Symposium Proceedings, pp. 977-982.

Makin et al, "Confirmed Bulk Abiation and Therapy Monitoring Using Intracorporeal Image-Treat Ultrasound Arrays," 4th International Symposium on Theraputic Ultrasound, Sep. 19, 2004.

Makin et al., "Miniaturized Ultrasound Arrays for Interstitial Ablation and Imaging," UltraSound Med. Biol. 2005, Nov. 1, 2005, pp. 1539-1550, vol. 31(11).

Manohar et al, "Photoacoustic mammography laboratory prototype: imaging of breast tissue phantoms," Journal of Biomedical Optics, Nov./Dec. 2004, pp. 1172-1181, vol. 9, No. 6.

Mast et al, "Bulk Ablation of Soft Tissue with Intense Ultrasound; Modeling nad Experiments," J. Acoust. Soc. Am., Oct. 1, 2005, pp. 2715-2724, vol. 118(4).

(56) References Cited

OTHER PUBLICATIONS

Mitragotri, Samir, "Healing sound: the use of ultrasound in drug delivery and other therapeutic applications," Nature Reviews; Drug Delivery, pp. 255-260, vol. 4.
Paradossi et al., "Poly(vinyl alcohol) as versatile biomaterial for potential biomedical applications," Journal of Materials Science: Materials in Medicine, 2003, pp. 687-691, vol. 14.
Reid, Gavin, et al., Abstract, "Tandem Mass spectometry of ribonuclease A and B: N-linked glycosylation site analysis of whole protein ions," Analytical Chemistry. Feb. 1, 2002, vol. 74, No. 3, pp. 577-583.
Righetti et al, "Elastographic Characterization of HIFU-Induced Lesions in Canine Livers," 1999, Ultrasound in Med & Bio, vol. 25, No. 7, pp. 1099-1113.
Sanghvi, N.T., et al., "Transrectal Ablation of Prostrate Tissue Using Focused Ultrasound," 1993 Ultrasonics Symposium, IEEE, pp. 1207-1210.
Sassen, Sander, "ATI's R520 architecture, the new king of the hill?" http://www.hardwareanalysis.com/content/article/1813, Sep. 16, 2005, 2 pages.
Seip, Ralf, et al., "Noninvasive Estimation of Tissue Temperature Response to Heating Fields Using Diagnostic Ultrasound," IEEE Transactions on Biomedical Engineering, vol. 42, No. 8, Aug. 1995, pp. 828-839.
Seip, Ralf, et al., "Noninvasive Detection of Thermal Effects Due to Highly Focused Ultrasonic Fields," IEEE Symposium, pp. 1229-1232, vol. 2, Oct. 3-Nov. 1993.
Smith, Nadine Barrie, et al., "Non-invasive In Vivo Temperature Mapping of Ultrasound Heating Using Magnetic Resonance Techniques", 1994 Ultrasonics Symposium, pp. 1829-1832, vol. 3.
Surry et al., "Poly(vinyl alcohol) cryogel phantoms for use in ultrasound and MR imaging," Phys. Med. Biol., Dec. 6, 2004, pp. 5529-5546, vol. 49.
Syka J. E. P. et al., "Peptide and Protein Sequence Analysis by Electron Transfer Dissociation Mass Spectometry," Proceedings of the National Academy of Sciences of USA, National Academy of Aceince, Washington, DC, vol. 101, No. 26, Jun. 29, 2004, pp. 9528-9533.
Ueno, S., et al., "Ultrasound Termometry in Hyperthermia", 1990 Ultrasonic Symposium, pp. 1645-1652.
Wang, H., et al., "Limits on Focused Ultrasound for Deep Hyperthermia", 1994 Ultrasonic Symposium, Nov. 1-4, 1994, pp. 1869-1872, vol. 3.
Wasson, Scott, "NVIDIA's GeForce 7800 GTX graphics processor Power MADD," http://techreport.com/reviews/2005q2/geforce-7800gtx/index.x?pg=1, Jun. 22, 2005, 4 pages.
White et al "Selective Creating of Thermal Injury Zones in the Superficial Musculoaponeurotic System Using Intense Ultrasound Therapy," Arch Facial Plastic Surgery, Jan./Feb. 2007, vol. 9, No. 1.
U.S. Appl. No. 12/996,616, filed Jan. 12, 2011, Hand Wand for Ultrasonic Cosmetic Treatment and Imaging.
U.S. Appl. No. 12/509,254, Jul. 24, 2009, Method and System for Enhancing Computer Peripheral Safety.
U.S. Appl. No. 11/538,794, Oct. 4, 2006, Ultrasound System and Method for Imaging and/or Measuring Displacement of Moving Tissue and Fluid.
Makin et al, "B-Scan Imaging and Thermal Lesion Monitoring Using Miniaturized Dual-Functionality Ultrasound Arrays," Ultrasonics Symposium, 2004 IEEE, Aug. 23, 2004, pp. 1788-1791, vol. 3.
Talbert, D. G., "An Add-On Modification for Linear Array Real-Time Ultrasound Scanners to Produce 3D Displays," UTS Int'l 1977 Brighton, England (Jun. 28-30, 1977) pp. 57-67.
Arthur et al., "Non-invasive estimation of hyperthermia temperatures with ultrasound," Int. J. Hyperthermia, Sep. 2005, 21(6), pp. 589-600.
Decision of the Korean Intellectual Property Tribunal dated Jun. 28, 2013 regarding Korean Patent No. 10-1142108, which is related to the pending application and/or an application identified in the Table on pp. 1-4 of the Information Disclosure Statement herein (English translation, English translation certification, and Korean decision included).
U.S. Appl. No. 13/789,562, filed Mar. 8, 2013, Method and System for Ultrasound Treatment of Fat.
U.S. Appl. No. 12/646,609, filed Dec. 23, 2009, Methods for Fat Reduction and Cellulite Treatment.
Calderhead et al., "One Mechanism Behind LED Photo-Therapy for Wound Healing and Skin Rejuvenation: Key Role of the Mast Cell" Laser Therapy 17.3: 141-148 (2008).
U.S. Appl. No. 13/245,822, filed Sep. 26, 2011, System and Method for Cosmetic Treatment.
U.S. Appl. No. 13/245,852, filed Sep. 26, 2011, Systems for Cosmetic Treatment.
U.S. Appl. No. 13/245,864, filed Sep. 27, 2011, Methods for Non-Invasive Cosmetic Treatment of the Eye Region.
U.S. Appl. No. 13/246,117, filed Sep. 27, 2011, Methods for Non-Invasive Lifting and Tightening of the Lower Face and Neck.
U.S. Appl. No. 13/246,112, filed Sep. 27, 2011, Tissue Imaging and Treatment Method.
U.S. Appl. No. 14/193,234, filed Feb. 28, 2014, Devices and Methods for Multi-Focus Ultrasound Therapy.
U.S. Appl. No. 08/950,353, filed Oct. 14, 1997, Imaging, Therapy and Temperature Monitoring Ultrasonic System.
U.S. Appl. No. 09/502,174, filed Feb. 10, 2000, Imaging, Therapy and Temperature Monitoring Ultrasonic System.
U.S. Appl. No. 10/193,419, filed Jul. 10, 2002, Imaging, Therapy and Temperature Monitoring Ultrasonic System.
U.S. Appl. No. 10/944,499, filed Sep. 16, 2004, Method and System for Ultrasound Treatment With a Multi-Directional Transducer.
U.S. Appl. No. 11/163,177, filed Oct. 7, 2005, Method and System for Treating Acne and Sebaceous Glands.
U.S. Appl. No. 10/950,112, filed Sep. 24, 2004, Method and System for Combined Ultrasound Treatment.
U.S. Appl. No. 11/163,178, filed Oct. 7, 2005, Method and System for Treating Stretch Marks.
U.S. Appl. No. 11/245,999, filed Oct. 6, 2005, System and Method for Ultra-High Frequency Ultrasound Treatment.
U.S. Appl. No. 10/944,500, filed Sep. 16, 2004, System and Method for Variable Depth Ultrasound Treatment.
U.S. Appl. No. 11/744,655, filed May 4, 2007, Imaging, Therapy and Temperature Monitoring Ultrasonic System.
U.S. Appl. No. 13/937,190, filed Jul. 8, 2013, Imaging, Therapy and Temperature Monitoring Ultrasonic System.
U.S. Appl. No. 12/135,962, filed Jun. 9, 2008, Method and System for Ultrasound Treatment With a Multi-Directional Transducer.
U.S. Appl. No. 12/792,934, filed Jun. 3, 2010, System and Method for Ultra-High Frequency Ultrasound Treatment.
U.S. Appl. No. 13/914,945, filed Jun. 11, 2013, System and Method for Ultra-High Frequency Ultrasound Treatment.
U.S. Appl. No. 12/834,754, filed Jul. 12, 2010, System and Method for Variable Depth Ultrasound Treatment.
U.S. Appl. No. 14/264,732, filed Apr. 29, 2014, System and Method for Variable Depth Ultrasound Treatment.
U.S. Appl. No. 11/126,760, filed May 11, 2005, Method and System for Three-Dimensional Scanning and Imaging.
U.S. Appl. No. 13/564,552, filed Aug. 1, 2012, Method and System for Controlled Scanning, Imaging and/or Therapy.
U.S. Appl. No. 12/437,726, filed May 8, 2009, Method and System for Combined Ultrasound Treatment.
U.S. Appl. No. 11/163,148, filed Oct. 6, 2005, Method and System for Controlled Thermal Injury of Human Superficial Tissue.
U.S. Appl. No. 13/444,688, filed Apr. 11, 2012, Customized Cosmetic Treatment.
U.S. Appl. No. 11/163,152, filed Oct. 6, 2005, Method and System for Treatment of Sweat Glands.
U.S. Appl. No. 13/444,485, filed Apr. 11, 2012, Methods for Treatment of Sweat Glands.
U.S. Appl. No. 13/603,159, filed Sep. 4, 2012, Methods for Treatment of Hyperhidrosis.
U.S. Appl. No. 13/603,279, filed Sep. 4, 2012, Energy Based Hyperhidrosis Treatment.

(56) References Cited

OTHER PUBLICATIONS

U.S. Appl. No. 13/950,728, filed Jul. 25, 2013, Energy Based Hyperhidrosis Treatment.
U.S. Appl. No. 14/571,835, filed Dec. 16, 2014, Energy Based Hyperhidrosis Treatment.
U.S. Appl. No. 11/163,151, filed Oct. 6, 2005, Method and System for Noninvasive Face Lifts and Deep Tissue Tightening.
U.S. Appl. No. 13/444,336, filed Apr. 11, 2012, Treatment of Sub-Dermal Regions for Cosmetic Effects.
U.S. Appl. No. 13/679,430, filed Nov. 16, 2012, Ultrasound Treatment of Sub-Dermal Tissue for Cosmetic Effects.
U.S. Appl. No. 13/924,376, filed Jun. 21, 2013, Noninvasive Tissue Tightening for Cosmetic Effects.
U.S. Appl. No. 13/924,355, filed Jun. 21, 2013, Noninvasive Aesthetic Treatment for Tightening Tissue.
U.S. Appl. No. 13/924,323, filed Jun. 21, 2013, Energy-Based Tissue Tightening.
U.S. Appl. No. 14/200,852, filed Mar. 7, 2014, Noninvasive Tissue Tightening System.
U.S. Appl. No. 14/200,961, filed Mar. 7, 2014, Energy-Based Tissue Tightening System.
U.S. Appl. No. 12/028,636, filed Feb. 8, 2008, Method and System for Noninvasive Face Lifts and Deep Tissue Tightening.
U.S. Appl. No. 13/964,820, filed Aug. 12, 2013, Methods for Noninvasive Skin Tightening.
U.S. Appl. No. 14/201,256, filed Mar. 7, 2014, System for Noninvasive Skin Tightening.
U.S. Appl. No. 15/098,139, filed Apr. 13, 2016, System and Method for Noninvasive Skin Tightening.
U.S. Appl. No. 14/685,390, filed Apr. 13, 2015, Energy-Based Tissue Tightening System.
U.S. Appl. No. 11/163,150, filed Oct. 6, 2005, Method and System for Photoaged Tissue.
U.S. Appl. No. 13/230,498, filed Sep. 12, 2011, Method and System for Photoaged Tissue.
U.S. Appl. No. 14/169,709, filed Jan. 31, 2014, Methods for Treating Skin Laxity.
U.S. Appl. No. 14/692,114, filed Apr. 21, 2015, Systems for Treating Skin Laxity.
U.S. Appl. No. 11/163,176, filed Oct. 7, 2005, Method and System for Treating Blood Vessel Disorders.
U.S. Appl. No. 13/601,742, filed Aug. 31, 2012, Method and System for Treating Blood Vessel Disorders.
U.S. Appl. No. 12/574,512, filed Oct. 6, 2009, Method and System for Treating Stretch Marks.
U.S. Appl. No. 14/554,668, filed Nov. 26, 2014, Method and System for Treating Stretch Marks.
U.S. Appl. No. 11/857,989, filed Sep. 19, 2007, Method and System for Treating Muscle, Tendon, Ligament and Cartilage Tissue.
U.S. Appl. No. 13/494,856, filed Jun. 12, 2012, Method and System for Treating Muscle, Tendon, Ligament and Cartilage Tissue.
U.S. Appl. No. 13/835,635, filed Mar. 15, 2013, Methods for Face and Neck Lifts.
U.S. Appl. No. 13/965,741, filed Aug. 13, 2013, Methods for Preheating Tissue for Cosmetic Treatment of the Face and Body.
U.S. Appl. No. 14/740,092, filed Jun. 15, 2015, Methods for Rejuvenating Skin by Heating Tissue for Cosmetic Treatment of the Face and Body.
U.S. Appl. No. 14/628,198, filed Feb. 20, 2015, System and Method for Treating Cartilage and Injuries to Joints and Connective Tissue.
U.S. Appl. No. 14/554,571, filed Nov. 26, 2014, Methods for Face and Neck Lifts.
U.S. Appl. No. 12/954,484, filed Nov. 24, 2010, Methods and Systems for Generating Thermal Bubbles for Improved Ultrasound Imaging and Therapy.
U.S. Appl. No. 12/350,383, filed Jan. 8, 2009, Method and System for Treating Acne and Sebaceous Glands.
U.S. Appl. No. 12/116,845, filed May 7, 2008, Method and System for Combined Energy Profile.
U.S. Appl. No. 14/643,749, filed Mar. 10, 2015, Method and System for Combined Energy Profile.
U.S. Appl. No. 08/766,083, filed Dec. 16, 1996, Method and Apparatus for Surface Ultrasound Imaging.
U.S. Appl. No. 09/113,227, filed Jul. 10, 1998, Method and Apparatus for Three Dimensional Ultrasound Imaging.
U.S. Appl. No. 08/944,261, filed Oct. 6, 1997, Wideband Acoustic Transducer.
U.S. Appl. No. 09/434,078, filed Nov. 5, 1999, Method and Apparatus for Three Dimensional Ultrasound Imaging.
U.S. Appl. No. 09/523,890, filed Mar. 13, 2000, Method and Apparatus for Three Dimensional Ultrasound Imaging.
U.S. Appl. No. 09/419,543, filed Oct. 18, 1999, Peripheral Ultrasound Imaging System.
U.S. Appl. No. 09/750,816, filed Dec. 28, 2000, Visual Imaging System for Ultrasonic Probe.
U.S. Appl. No. 10/358,110, filed Feb. 4, 2003, Visual Imaging System for Ultrasonic Probe.
U.S. Appl. No. 11/380,161, filed Apr. 25, 2006, Method and System for Enhancing Computer Peripheral Safety.
U.S. Appl. No. 11/554,272, filed Oct. 30, 2006, Visual Imaging System for Ultrasonic Probe.
U.S. Appl. No. 13/071,298, filed Mar. 24, 2011, Visual Imaging System for Ultrasonic Probe.
U.S. Appl. No. 13/854,936, filed Mar. 25, 2013, Visual Imaging System for Ultrasonic Probe.
U.S. Appl. No. 12/509,254, filed Jul. 24, 2009, Method and System for Enhancing Computer Peripheral Safety.
U.S. Appl. No. 13/453,847, filed Apr. 23, 2012, Method and System for Enhancing Computer Peripheral Safety.
U.S. Appl. No. 11/538,794, filed Oct. 4, 2006, Ultrasound System and Method for Imaging and/or Measuring Displacement of Moving Tissue and Fluid.
U.S. Appl. No. 09/502,175, filed Feb. 10, 2000, Method and Apparatus for Safely Delivering Medicants to a Region of Tissue, Using Imaging, Therapy and Temperature Monitoring.
U.S. Appl. No. 08/943,728, filed Oct. 3, 1997, Method and Apparatus for Safely Delivering Medicants to a Region of Tissue Using Ultrasound.
U.S. Appl. No. 12/415,945, filed Mar. 31, 2009, Method and System for Noninvasive Mastopexy.
U.S. Appl. No. 11/163,155, filed Oct. 6, 2005, Method and System for Noninvasive Mastopexy.
U.S. Appl. No. 11/163,154, filed Oct. 6, 2005, Method and System for Treatment of Cellulite.
U.S. Appl. No. 13/356,405, filed Jan. 23, 2012, Method and System for Treatment of Cellulite.
U.S. Appl. No. 13/789,562, filed Mar. 7, 2013, Method and System for Ultrasound Treatment of Fat.
U.S. Appl. No. 14/164,598, filed Jan. 27, 2013, Method for Fat and Cellulite Reduction.
U.S. Appl. No. 14/550,720, filed Nov. 21, 2014, System and Method for Fat and Cellulite Reduction.
U.S. Appl. No. 15/041,829, filed Feb. 11, 2016, System and Method for Fat and Cellulite Reduction.
U.S. Appl. No. 11/738,682, filed Apr. 23, 2007, Method and System for Non-Ablative Acne Treatment and Prevention.
U.S. Appl. No. 12/116,810, filed May 7, 2008, Methods and Systems for Modulating Medicants Using Acoustic Energy.
U.S. Appl. No. 12/116,828, filed May 7, 2008, Methods and Systems for Coupling and Focusing Acoustic Energy Using a Coupler Member.
U.S. Appl. No. 12/646,609, filed Dec. 23, 2009, Methods and System for Fat Reduction and/or Cellulite Treatment.
U.S. Appl. No. 14/192,520, filed Feb. 27, 2014, Energy Based Fat Reduction.
U.S. Appl. No. 14/550,772, filed Nov. 21, 2014, Energy Based Fat Reduction.
U.S. Appl. No. 15/401,804, filed Feb. 11, 2016, Energy Based Fat Reduction.
U.S. Appl. No. 13/291,312, filed Nov. 11, 2011, Devices and Methods for Acoustic Shielding.

(56) References Cited

OTHER PUBLICATIONS

U.S. Appl. No. 14/487,504, filed Sep. 16, 2014, Devices and Methods for Acoustic Shielding.
U.S. Appl. No. 13/136,538, filed Aug. 2, 2011, Systems and Methods for Treating Acute and/or Chronic Injuries in Soft Tissue.
U.S. Appl. No. 13/136,542, filed Aug. 2, 2011, System and Method for Treating Cartilage.
U.S. Appl. No. 13/163,541, filed Aug. 2, 2011, Methods and Systems for Treating Plantar Fascia.
U.S. Appl. No. 13/136,544, filed Aug. 2, 2011, Systems and Methods for Ultrasound Treatment.
U.S. Appl. No. 13/547,023, filed Jul. 11, 2012, Systems and Methods for Coupling an Ultrasound Source to Tissue.
U.S. Appl. No. 13/545,931, filed Jul. 10, 2012, Methods and Systems for Controlling Acoustic Energy Deposition Into a Medium.
U.S. Appl. No. 13/545,953, filed Jul. 10, 2012, Systems and Methods for Accelerating Healing of Implanted Material and/or Native Tissue.
U.S. Appl. No. 13/547,011, filed Jul. 11, 2012, Systems and Methods for Monitoring and Controlling Ultrasound Power Output and Stability.
U.S. Appl. No. 13/545,954, filed Jul. 10, 2012, Systems and Methods for Improving an Outside Appearance of Skin Using Ultrasound as an Energy Source.
U.S. Appl. No. 13/545,945, filed Jul. 10, 2012, Systems and Methods for Treating Injuries to Joints and Connective Tissue.
U.S. Appl. No. 13/545,929, filed Jul. 10, 2012, Methods and Systems for Ultrasound Treatment.
U.S. Appl. No. 13/863,249, filed Apr. 15, 2013, Systems for Cosmetic Treatment.
U.S. Appl. No. 13/863,281, filed Apr. 15, 2013, Methods for Non-invasive Cosmetic Treatment.
U.S. Appl. No. 14/847,626, filed Sep. 8, 2015, Systems for Cosmetic Treatment.
U.S. Appl. No. 13/863,362, filed Apr. 15, 2013, Thick Film Transducer Arrays.
U.S. Appl. No. 14/217,110, filed Mar. 17, 2014, Ultrasound Treatment Device and Method of Use.
U.S. Appl. No. 14/217,382, filed Mar. 17, 2014, Ultrasound Treatment Device and Method of Use.
U.S. Appl. No. 14/225,189, filed Mar. 25, 2014, Reflective Ultrasound Technology for Dermatological Treatments.
U.S. Appl. No. 14/270,859, filed May 6, 2014, Methods and Systems for Generating Thermal Bubbles for Improved Ultrasound Imaging and Therapy.
U.S. Appl. No. 14/679,494, filed Apr. 6, 2015, Methods and Systems for Generating Thermal Bubbles for Improved Ultrasound Imaging and Therapy.
U.S. Appl. No. 14/405,368, filed Dec. 3, 2014, Devices and Methods for Ultrasound Focal Depth Control.
U.S. Appl. No. 14/568,954, filed Dec. 12, 2014, System and Method for Cosmetic Enhancement of Lips.
U.S. Appl. No. 14/569,001, filed Dec. 12, 2014, System and Method for Non-Invasive Treatment With Improved Efficiency.
U.S. Appl. No. 14/600,782, filed Jan. 20, 2015, Methods and Systems for Controlling and Acoustic Energy Deposition in Various Media.
U.S. Appl. No. 14/738,420, filed Jun. 12, 2015, Systems and Methods for Fast Ultrasound Treatment.
U.S. Appl. No. 14/751,349, filed Jun. 26, 2015, Methods and Systems for Tattoo Removal.
Chapelon et al., "Effects of Cavitation in the High Intensity Therapeutic Ultrasound", Ultrasonics Symposium—1357 (1991).
Chapelon, et al., "Thresholds for Tissue Ablation by Focused Ultrasound" (1990).
Fujimoto, et al., "A New Cavitation Suppression Technique for Local Ablation Using High-Intensity Focused Ultrasound" Ultrasonics Symposium—1629 (1995).
Hynynen et al., Temperature Distributions During Local Ultrasound Induced Hyperthermia In Vivo, Ultrasonics Symposium—745 (1982).
Agren, Magnus S. et al., Collagenase in Wound Healing: Effect of Wound Age and Type. The Journal of Investigative Dermatology, vol. 99/No. 6, (Dec. 1992).
Alam, M., "The future of noninvasive procedural dermatology". Semin Cutan Med Surg. Mar. 2013; 32(1):59-61.
Alam, M., et al., "Ultrasound tightening of facial and neck skin: a rater-blinded prospective cohort study". J Am Acad Dermatol, 2010. 62(2): p. 262-9.
Alexiades-Armenakas, M., "Ultrasound Technologies for Dermatologic Techniques". J Drugs Derm. 2014. 12 (11): p. 1305.
Alster, T.S., et. al., "Noninvasive lifting of arm, thigh, and knee skin with transcutaneousintense focused ultrasound". Dermatol Surg, 2012. 38(5): p. 754-9.
Arosarena, O., "Options and Challenges for Facial Rejuvenation in Patients With Higher Fitzpatrick Skin Phototypes". JAMA Facial Plastic Surgery, 2015.
Bozec, Laurent et al., Thermal Denaturation Studies of Collagen by Microthermal Analysis and Atomic Force Microscopy, Biophysical Journal, vol. 101, pp. 228-236. (Jul. 2001).
Brobst, R.W., et. al., "Noninvasive Treatment of the Neck". Facial Plast Surg Clin North Am, 2014. 22(2): p. 191-202.
Brobst, R.W., et., al., "Ulthera: initial and six month results". Facial Plast Surg Clin North Am, 2012. 20(2): p. 163-76.
Casabona, G., et. al., "Microfocused Ultrasound With Visualization and Fillers for Increased Neocollagenesis: Clinical and Histological Evaluation". Dermatol Surg 2014;40:S194-S198.
Chan, N.P., et al., "Safety study of transcutaneous focused ultrasound for non-invasive skin tightening in Asians". Lasers Surg Med, 2011. 43(5): p. 366-75.
Dayan, S.H., et al., "Prospective, Multi-Center, Pivotal Trial Evaluating the Safety and Effectiveness of Micro-Focused Ultrasound with Visualization (MFU-V) for Improvement in Lines and Wrinkles of the Décolletage". Plast Reconstr Surg. Oct. 2014; 134(4 Suppl 1):123-4.
Dierickx, Christine C., "The Role of Deep Heating for Noninvasive Skin Rejuvenation" Lasers in Surgery and Medicine 38:799-807 (2006).
Dobke, M.K., et al., "Tissue restructuring by energy-based surgical tools". Clin Plast Surg, 2012. 39(4): p. 399-408.
Dong, Yuan-Lin et al., "Effect of Ibuprofen on the Inflammatory Response to Surgical Wounds" The Journal of Trauma, vol. 35, No. 3. (1993).
Dvivedi, Sanjay, et al. "Effect of Ibuprofen and diclofenac sodium on experimental wound healing" Indian Journal of Experimental Biology, vol. 35, pp. 1243-1245. (Nov. 1997).
Fabi, S.G., "Microfocused Ultrasound With Visualization for Skin Tightening and Lifting: My Experience and a Review of the Literature". Dermatol Surg. Dec. 2014; 40 Suppl 12:S164-7.
Fabi, S.G., "Noninvasive skin tightening: focus on new ultrasound techniques". Clin Cosmet Investig Dermatol. Feb. 5, 2015; 8:47-52.
Fabi, S.G., et. al., "A prospective multicenter pilot study of the safety and efficacy of microfocused ultrasound with visualization for improving lines and wrinkles of the décolleté". Dermatol Surg. Mar. 2015; 41(3):327-35.
Fabi, S.G., et. al., "Evaluation of microfocused ultrasound with visualization for lifting, tightening, and wrinkle reduction of the decolletage". J Am Acad Dermatol, 2013. 69(6): p. 965-71.
Fabi, S.G., et. al., "Future directions in cutaneous laser surgery". Dermatol Clin, 2014. 32(1): p. 61-9.
Fabi, S.G., et. al., "Retrospective Evaluation of Micro-focused Ultrasound for Lifting and Tightening the Face and Neck". Dermatol Surg, 2014.
Friedmann D.P., "Comments on evaluation of microfocused ultrasound system for improving skin laxity and tightening in the lower face". Aesthet Surg J. Mar. 2015;35(3):NP81-2.
Friedmann, D.P., et. al., "Combination of intense pulsed light, Sculptra, and Ultherapy for treatment of the aging face". J Cosmet Dermatol, 2014. 13(2): p. 109-18.
Gold, M.H., et. al., "Use of Micro-Focused Ultrasound with Visualization to Lift and Tighten Lax Knee Skin". J Cosmet Laser Ther, 2014: p. 1-15.

(56) References Cited

OTHER PUBLICATIONS

Goldberg, D.J., et. al., "Safety and Efficacy of Microfocused Ultrasound to Lift, Tighten, and Smooth the Buttocks". Dermatol Surg 2014; 40:1113-1117.
Greene, R.M., et al., "Skin tightening technologies". Facial Plast Surg. Feb. 2014; 30(1):62-7.
Greenhalgh, David G., "Wound healing and diabetes mellitus" Clinics in Plastic Surgery 30; 37-45. (2003).
Guo, S. et al., "Factors Affecting Wound Healing" Critical Reviews in Oral Biology & Medicine, J Dent Res 89(3), pp. 219-229. (2010).
Hantash, Basil M. et al., "Bipolar Fractional Radiofrequency Treatment Induces Neoelastogenesis and Neocollagenesis" Lasers in Surgery and Medicine 41:1-9 (2009).
Hantash, Basil M. et al., "In Vivo Histological Evaluation of a Novel Ablative Fractional Resurfacing Device" Lasers in Surgery and Medicine 39:96-107 (2007).
Harris, M.O., "Safety of Microfocused Ultrasound With Visualization in Patients With Fitzpatrick Skin Phototypes III to VI". JAMA Facial Plast. Surg, 2015.
Hart, et. al., "Current Concepts in the Use of PLLA:Clinical Synergy Noted with Combined Use of Microfocused Ultrasound and Poly-l-Lactic Acid on the Face, Neck, and Décolletage". Amer. Soc. Plast. Surg. 2015. 136; 180-187S.
Hitchcock, T.M. et. al., "Review of the safety profile for microfocused ultrasound with Visualization". Journal of Cosmetic Dermatology, 13, 329-335. (2014).
Jeong, K.H., et al., "Neurologic complication associated with intense focused ultrasound". J Cosmet Laser Ther, 2013.
Kim, H.J., et al., "Coagulation and ablation patterns of high-intensity focused ultrasound on a tissue mimicking phantom and cadaveric skin". Laser Med Sci. Sep. 4, 2015.
Kornstein, A.N., "Ulthera for silicone lip correction". Plast Reconstr Surg, 2012. 129(6): p. 1014e-1015e.
Kornstein, A.N., "Ultherapy shrinks nasal skin after rhinoplasty following failure of conservative measures". Plast Reconstr Surg, 2013. 131(4): p. 664e-6e.
Krischak, G.D., et al., "The effects of non-steroidal anti-inflammatory drug application on incisional wound healing in rats" Journal of Wound Care, vol. 6, No. 2, (Feb. 2007).
Laubach, H.J., et. al., "Confined Thermal Damage with Intense Ultrasound (IUS)" [abstr.] American Society for Laser Medicine and Surgery Abstracts, p. 15 #43 (Apr. 2006).
Laubach, H.J., et. al., "Intense focused ultrasound: evaluation of a new treatment modality for precise microcoagulation within the skin". Dermatol Surg, 2008. 34(5): p. 727-34.
Lee, H.J., et. al., "The efficacy and safety of intense focused ultrasound in the treatment of enlarged facial pores in Asian skin". J Dermatolog Treat, 2014.
Lee, H.S., et. al., "Multiple Pass Ultrasound Tightening of Skin Laxity of the Lower Face and Neck". Dermatol Surg, 2011.
Lin, Sung-Jan, et al., "Monitoring the thermally induced structural transitions of collagen by use of second-harmonic generation microscopy" Optics Letters, vol. 30, No. 6, (Mar. 15, 2005).
MacGregor J.L., et. al., "Microfocused Ultrasound for Skin Tightening". Semin Cutan Med Surg 32:18-25. (2013).
Meshkinpour, Azin, et al., "Treatment of Hypertrophic Scars and Keloids With a Radiofrequency Device: A Study of Collagen Effects" Lasers in Surgery and Medicine 37:343-349 (2005).
Minkis, K., et. al., "Ultrasound skin tightening". Dermatol Clin, 2014. 32(1): p. 71-7.
Mosser, David M. et al., "Exploring the full spectrum of macrophage activation" Nat Rev Immunol; 8(12): 958-969. (Dec. 2008).
Murota, Sei-Itsu, et al., "Stimulatory Effect of Prostaglandins on the Production of Hexosamine-Containing Substances by Cultured Fibroblasts (3) Induction of Hyaluronic Acid Synthetase by Prostaglandin" Department of Pharmacology, Tokyo Metropolitan Institute of Gerontology, Itabashiku, Tokyo-173, Japan. (Nov. 1977, vol. 14, No. 5).
Murota, Sei-Itsu, et al., "The Stimulatory Effect of Prostaglandins on Production of Hexosamine-Containing Substances by Cultured Fibroblasts" Department of Pharmacology, Tokyo Metropolitan Institute of Gerontology, Itabashiku, Tokyo-173, Japan. (Aug. 1976, vol. 12, No. 2).
Nestor, M.S. et. al., "Safety and Efficacy of Micro-focused Ultrasound Plus Visualization for the Treatment of Axillary Hyperhidrosis". J Clin Aesthet Dermatol, 2014. 7(4): p. 14-21.
Oni, G., et. al. "Response to 'comments on evaluation of microfocused ultrasound system for improving skin laxity and tightening in the lower face'". Aesthet Surg J. Mar. 2015;35(3):NP83-4.
Oni, G., et. al., "Evaluation of a Microfocused Ultrasound System for Improving Skin Laxity and Tightening in the Lower Face". Aesthet Surg J, 2014. 38:861-868.
Pak, C.S., et. al., "Safety and Efficacy of Ulthera in the Rejuvenation of Aging Lower Eyelids: A Pivotal Clinical Trial". Aesthetic Plast Surg, 2014.
Pritzker, R.N., et. al, "Updates in noninvasive and minimally invasive skin tightening". Semin Cutan Med Surg. Dec. 2014;33(4):182-7.
Pritzker, R.N., et. al., "Comparison of different technologies for noninvasive skin tightening". Journal of Cosmetic Dermatology, 13, 315-323. (2014).
Rappolee, Daniel A., et al., "Wound Macrophages Express TGF and Other Growth Factors in Vivo: Analysis by mRNA Phenotyping" Science, vol. 241, No. 4866 (Aug. 1988).
Rokhsar, C., et. al., "Safety and efficacy of microfocused ultrasound in tightening of lax elbow skin". Dermatol Surg. 2015; 41(7):821-6.
Rosenberg, Carol S. "Wound Healing in the Patient with Diabetes Mellitus" Nursing Clinics of North America, vol. 25, No. 1, (Mar. 1990).
Sabet-Peyman, E.J. et. al., "Complications Using Intense Ultrasound Therapy to TreatDeep Dermal Facial Skin and Subcutaneous Tissues". Dermatol Surg 2014; 40:1108-1112.
Sandulache, Vlad C. et al., "Prostaglandin E2 inhibition of keloid fibroblast migration, contraction, and transforming growth factor (TGF)—B1—induced collagen synthesis" Wound Rep Reg 15 122-133, 2007. (2007).
Sasaki, G.H. et. al., "Clinical Efficacy and Safety of Focused-Image Ultrasonography: A 2-Year Experience". Aesthet Surg J, 2012.
Sasaki, G.H. et. al., "Microfocused Ultrasound for Nonablative Skin and Subdermal Tightening to the Periorbitum and Body Sites: Preliminary Report on Eighty-Two Patients". Journal of Cosmetics, Dermatological Sciences and Applications, 2012, 2, 108-116.
Sklar, L.R., et. al., "Use of transcutaneous ultrasound for lipolysis and skin tightening: a review". Aesthetic Plast Surg, 2014. 38(2): p. 429-41.
Suh, D.H., et. al., "A intense-focused ultrasound tightening for the treatment of infraorbital laxity". J Cosmet Laser Ther, 2012. 14(6): p. 290-5.
Suh, D.H., et. al., "Comparative histometric analysis of the effects of high-intensity focused ultrasound and radiofrequency on skin". J Cosmet Laser Ther. Mar. 2015 24:1-7.
Suh, D.H., et. al., "Intense Focused Ultrasound Tightening in Asian Skin: Clinical and Pathologic Results" American Society for Dermatologic Surgery, Inc.; 37:1595-1602. (2011).
Suh, D.H., et. al., "Intense focused ultrasound tightening in asian skin: clinical and pathologic results". Dermatol Surg, 2011. 37(11): p. 1595-602.
Verhofstad, Michiel H.J. et al., "Collagen Synthesis in rat skin and ileum fibroblasts is affected differently by diabetes-related factors" Int. J. Exp. Path. (1998), 79, 321-328.
Weiss, M., "Commentary: noninvasive skin tightening: ultrasound and other technologies: where are we in 2011?" Dermatol Surg, 2012. 38(1): p. 28-30.
White, W. M., et al., "Selective Transcutaneous Delivery of Energy to Facial Subdermal Tissues Using the Ultrasound Therapy System" [abstr]. American Society for Laser Medicine and Surgery Abstracts, p. 37 #113 (Apr. 2006).
White, W. Matthew, et al., "Selective Transcutaneous Delivery of Energy to Porcine Soft Tissues Using Intense Ultrasound (IUS)" Lasers in Surgery and Medicine 40:67-75 (2008).

(56) References Cited

OTHER PUBLICATIONS

Woodward, J.A., et. al. "Safety and Efficacy of Combining Microfocused Ultrasound With Fractional CO2 Laser Resurfacing for Lifting and Tightening the Face and Neck". Dermatol Surg, Dec. 2014 40:S190-S193.
Zelickson, Brian D. et al., "Histological and Ultrastructural Evaluation of the Effects of a Radiofrequency-Based Nonablative Dermal Remodeling Device, A Pilot Study" Arch Dermatol, vol. 140, (Feb. 2004).
Ulthera, Inc., Petition for Inter Partes Review filed Jul. 19, 2016 in Re U.S. Pat. No. 6,113,559; IPR2016-01459; 63 pages.
Ulthera Exhibit 1001, U.S. Pat. No. 6,113,559 to Klopotek, filed Jul. 19, 2016 in re IPR2016-01459.
Ulthera Exhibit 1002, Patent file history of U.S. Pat. No. 6,113,559 Klopotek.
Ulthera Exhibit 1003, Declaration of Expert Witness Mark E. Schafer, Ph.D.
Ulthera Exhibit 1004, Curriculum Vitae of Mark E. Schafer, Ph.D.
Ulthera Exhibit 1005, International PCT Publication WO96/34568 Knowlton.
Ulthera Exhibit 1006, French Patent No. 2,672,486, Technomed patent.
Ulthera Exhibit 1007, English translation of French Patent No. 2,672,486, Technomed.
Ulthera Exhibit 1008, International PCT Publication WO93/12742, Technomed PCT.
Ulthera Exhibit 1009, English translation of International PCT Publication WO93/12742, Technomed PCT.
Ulthera Exhibit 1010, U.S. Pat. No. 5,601,526, which claims priority to Technomed PCT.
Ulthera Exhibit 1011, Patent file history for European Patent Application No. 98964890.2, Klopotek.
Ulthera Exhibit 1012, Translator Declaration.
Ulthera Exhibit 1013, U.S. Pat. No. 5,230,334 to Klopotek.
Ulthera Exhibit 1014, U.S. Pat. No. 5,755,753 to Knowlton.
Ulthera Exhibit 1015, Excerpts from The American Medical Association Encyclopedia of Medicine (1989).
Ulthera Exhibit 1016, The Simultaneous Study of Light Emissions and Shock Waves Produced by Cavitation Bubbles, G. Gimenez, J. Acoust. Soc. Am. 71(4), Apr. 1982, pp. 839-847.
Ulthera Exhibit 1017, Excerpts from Gray's Anatomy (1995).
Ulthera Exhibit 1018, Anatomy of the Superficial Venous System, Comjen G.M., Dermatol. Surg., 1995; 21:35-45.
Ulthera Exhibit 1019, Section 2.6 from Ultrasonics Theory and Application, by G.L. Gooberman (Hart Publishing Co., 1969).
Ulthera Exhibit 1020, Deep Local Hyperthermia for Cancer Therapy: External Electromagnetic and Ultrasound Techniques, A.Y. Cheung and A. Neyzari, Cancer Research (Suppl.), vol. 44, pp. 4736-4744 (1984).
Delon Martin, C., et al, "Venous Thrombosis Generation by Means of High-Intensity Focused Ultrasound" Ultrasound in Med. & Biol., vol. 21, No. 1, pp. 113-119 (1995).
A Validated Photonumeric Cellulite Severity Scale; Hexsel et al; J Eur Acad Dermatol Venereol. May 2009;23(5):523-8, 6 pages.
Microfocused Ultrasound with Visualization and Calcium Hydroxylapatite for Improving Skin Laxity and Cellulite Appearance; Casabona et al.; Plast Reconstr Surg Glob Open. Jul. 25, 2017;5(7):e1388, 8 pages.
Microfocused Ultrasound With Visualization and Fillers for Increased Neocollagenesis: Clinical and Histological Evaluation;I Casabona et al.; Dermatol Surg. Dec. 2014; 40 Suppl 12:S194-8, 5 pages.
Decision on Institution of Inter Partes Review in Re U.S. Pat. No. 6,113,559; IPR2016-01459; 20 pages. [011] (Dated Jan. 23, 2017).
Dermafocus Response to Institution of Inter Partes Review in Re U.S. Pat. No. 6,113,559; IPR2016-01459; 73 pages [018] (Dated Apr. 26, 2017).
Dermafocus Exhibit List in Re U.S. Pat. No. 6,113,559; IPR2016-01459; 5 pages [019] (Dated Apr. 26, 2017).
Dermafocus Exhibit 2002, Declaration of Mark Palmeri, in Re U.S. Pat. No. 6,113,559; IPR2016-01459; 136 pages (Filed Apr. 26, 2017).
Dermafocus Exhibit 2003, Deposition of Dr. Mark Schafer, in Re U.S. Pat. No. 6,113,559; IPR2016-01459; 327 pages (Filed Apr. 26, 2017).
Dermafocus Exhibit 2004, Amendment No. 4 to Ulthera Form S-1, in Re U.S. Pat. No. 6,113,559; IPR2016-01459; 308 pages (Filed Apr. 26, 2017).
Dermafocus Exhibit 2005, Excerpt from Churchill Livingstone, Gray's Anatomy (38th ed. 1995), in Re U.S. Pat. No. 6,113,559; IPR2016-01459; 7 pages (Filed Apr. 26, 2017).
Dermafocus Exhibit 2006, Bo Eklof et al., "Revision of the CEAP Classification for Chronic Venous Disorders: Consensus Statement," ACTA FAC MED NAISS, vol. 25, No. 1 (2008), 3-10 in Re U.S. Pat. No. 6,113,559; IPR2016-01459; 7 pages (Filed Apr. 26, 2017).
Dermafocus Exhibit 2007, WebMD, "Varicose Veins and Spider Veins" downloaded from http://www.webmd.com/skin-problems-andtreatments/guide/varicose-spider-veins#1 in Re U.S. Pat. No. 6,113,559; IPR2016-01459; 3 pages (Filed Apr. 26, 2017).
Dermafocus Exhibit 2008, John M. Porter et al, "Reporting Standards in Venous Disease: An Update," Journal of Vascular Surgery, vol. 21, No. 4 (1995), 635-645 in Re U.S. Pat. No. 6,113,559; IPR2016-01459; 11 pages (Filed Apr. 26, 2017).
Dermafocus Exhibit 2009, Kullervo Hynynen, "Review of Ultrasound Therapy," 1997 Ultrasonics Symposium (1997), 1305-1313, in Re U.S. Pat. No. 6,113,559; IPR2016-01459; 9 pages (Filed Apr. 26, 2017).
Dermafocus Exhibit 2010, A.G. Visioli et al, "Prelimiary Results of a Phase I Dose Escalation Clinical Trial Using Focused Ultrasound in the Treatment of Localised Tumours," European Journal of Ultrasound, vol. 9 (1999), 11-18, in Re U.S. Pat. No. 6,113,559; IPR2016-01459; 8 pages (Filed Apr. 26, 2017).
Dermafocus Exhibit 2011, U.S. Pat. No. 5,143,063, issued on Sep. 1, 1992, Fellner, in Re U.S. Pat. No. 6,113,559; IPR2016-01459; 6 pages (Filed Apr. 26, 2017).
Dermafocus Exhibit 2012, Hugh G. Beebe et al, "Consensus Statement: Classification and Grading of Chronic Venous Disease in the Lower Limbs," European Journal of Vascular and Endovascular Surgery, vol. 12 (1996), 487-492, in Re U.S. Pat. No. 6,113,559; IPR2016-01459; 6 pages (Filed Apr. 26, 2017).
Dermafocus Exhibit 2013, Excerpt from Mosby's Medical Dictionary (3rd ed. 1990), in Re U.S. Pat. No. 6,113,559; IPR2016-01459; 4 pages (Filed Apr. 26, 2017).
Dermafocus Exhibit 2014, Excerpt from Miller-Keane Encyclopedia & Dictionary of Medicine, Nursing, & Allied Health (5th ed. 1992), in Re U.S. Pat. No. 6,113,559; IPR2016-01459; 6 pages (Filed Apr. 26, 2017).
Dermafocus Exhibit 2015, David J. Tibbs et al, Varicose Veins, Venous Disorders, and Lymphatic Problems in the Lower Limbs (1997), Chapter 4: Clinical Patterns of Venous Disorder I, 47-67, in Re U.S. Pat. No. 6,113,559; IPR2016-01459; 24 pages (Filed Apr. 26, 2017).
Dermafocus Exhibit 2016, Mitchel P. Goldman et al, Varicose Veins and Telangiectasias (2nd ed. 1999), Chapter 22: Treatment of Leg Telangiectasias with Laser and High-Intensity Pulsed Light, 470-497, in Re U.S. Pat. No. 6,113,559; IPR2016-01459; 31 pages (Filed Apr. 26, 2017).
Dermafocus Exhibit 2017, Email from Anderson to Klopotek dated May 25, 2004, in Re U.S. Pat. No. 6,113,559; IPR2016-01459; 1 page (Filed Apr. 26, 2017).
Dermafocus Exhibit 2018, List of Klopotek Patents, in Re U.S. Pat. No. 6,113,559; IPR2016-01459; 411 pages (Filed Apr. 26, 2017).
Dermafocus Exhibit 2019, Declaration of Peter Klopotek Civil Action 15-cv-654-SLR, dated Nov. 2, 2016, in Re U.S. Pat. No. 6,113,559; IPR2016-01459; 1 page (Filed Apr. 26, 2017).
Dermafocus Exhibit 2020, "Our Technology," downloaded from http://jobs.ulthera.com/about on Apr. 10, 2017, in Re U.S. Pat. No. 6,113,559; IPR2016-01459; 4 pages (Filed Apr. 26, 2017).
Dermafocus Exhibit 2021, C. Damianou and K. Hynynen, "Focal Spacing and Near-Field Heating During Pulsed High Temperature Ultrasound Therapy," Ultrasound in Medicine & Biology, vol. 19,

(56) References Cited

OTHER PUBLICATIONS

No. 9 (1993), 777-787, in Re U.S. Pat. No. 6,113,559; IPR2016-01459; 11 pages (Filed Apr. 26, 2017).
Dermafocus Exhibit 2022, Excerpt from Mosby's Medical Dictionary (5th ed. 1997), in Re U.S. Pat. No. 6,113,559; IPR2016-01459; 5 pages (Filed Apr. 26, 2017).
Dermafocus Exhibit 2023, Excerpt from Miller-Keane Encyclopedia & Dictionary of Medicine, Nursing, & Allied Health (6th ed. 1997), in Re U.S. Pat. No. 6,113,559; IPR2016-01459; 7 pages (Filed Apr. 26, 2017).
Dermafocus Exhibit 2024, Excerpt from Stedman's Concise Medical Dictionary (3 rd ed. 1997), in Re U.S. Pat. No. 6,113,559; IPR2016-01459; 4 pages (Filed Apr. 26, 2017).
Dermafocus Exhibit 2025, Excerpt from Taber's Cyclopedic Medical Dictionary (18th ed. 1997), in Re U.S. Pat. No. 6,113,559; IPR2016-01459; 9 pages (Filed Apr. 26, 2017).
Dermafocus Exhibit 2026, Bo Eklof et al, "Revision of the CEAP Classification for Chronic Venous Disorders: Consensus Statement," Journal of Vascular Surgery, vol. 40, No. 6 (2004), 1248-1252.el, in Re U.S. Pat. No. 6,113,559; IPR2016-01459; 6 pages (Filed Apr. 26, 2017).
Ulthera, Inc., Reply in Support of Petition for Inter Partes Review in Re U.S. Pat. No. 6,113,559; IPR2016-01459; 33 pages (Filed Aug. 2, 2017).
Ulthera Exhibit 1022, Use of the Argon and Carbon Dioxide Lasers for Treatment of Superficial Venous Varicosities of the Lower Extremity, D. Apfelberg et al., Lasers in Surgery and Medicine, vol. 4.3, pp. 221-231 (1984) (filed Aug. 2, 2017 in re IPR2016-01459).
Ulthera Exhibit 1023, 532-Nanometer Green Laser Beam Treatment of Superficial Varicosities of the Lower Extremities, T. Smith et al., Lasers in Surgery and Medicine, vol. 8.2, pp. 130-134 (1988) (filed Aug. 2, 2017 in re IPR2016-01459).
Ulthera Exhibit 1024, Deposition Transcript of Dr. Mark Palmeri on Jul. 11, 2017 (filed Aug. 2, 2017 in re IPR2016-01459).
Ulthera Exhibit 1025, Ulthera Oral Proceeding Demonstrative Slides (filed Oct. 2, 2017 in re IPR2016-01459).
Dermafocus Exhibit 2027, DermaFocus Oral Proceeding Demonstrative Slides (filed Oct. 2, 2017 in re IPR2016-01459).
PTAB Record of Oral Hearing held Oct. 4, 2017 in Re U.S. Pat. No. 6,113,559; IPR2016-01459; 67 pages (PTAB Document sent to Ulthera on Nov. 1, 2017).
Carruthers et al., "Consensus Recommendations for Combined Aesthetic Interventions in the Face Using Botulinum Toxin, Fillers,and Energy-Based Devices" Dermatol Surg 2016 (pp. 1-12).
Final Written Decision of Inter Partes Review in Re U.S. Pat. No. 6,113,559; IPR2016-01459; 37 pages [030] (Entered Jan. 19, 2018).
Ulthera, Inc., Petitioner Notice of Appeal to Federal Circuit 2018-1542 re: IPR2016-01459; 4 pages from [001] (no appendices) (Filed Feb. 9, 2018).
Federal Circuit Order Granting Ulthera Motion to Remand, re: 2018-1542; 4 pages [022] (Dated May 25, 2018).
Microchip microID 125 kHz EFID System Design Guide, Microchip Technology Inc. (2004).
Adams et al., "High Intensity Focused Ultrasound Ablation of Rabiit Kidney Tumors" Sonablate High-Intensity Focused Ultrasound device; Journal of Endourology vol. 10, No. 1, (Feb. 1996).
Driller et al., "Therapeutic Applications of Ultrasound: A Review" IEEE Engineering in Medicine and Biology; (Dec. 1987) pp. 33-40.
Sonocare, Inc. Therapeutic Ultrasound System Model CST-100 Instruction Manual (1985).
Webster et al. "The role of ultrasound-induced cavitation in the 'in vitro' stimulation of collagen synthesis in human fibroblasts"; Ultrasonics pp. 33-37(Jan. 1980).
Ulthera Brief (Corrected), Fed. Cir. Appeal Case 19-1006 from re: IPR2016-01459; 136 pages [030] (Dated Apr. 3, 2019).
DermaFocus Brief (Corrected), Fed. Cir. Appeal Case 19-1006 from re: IPR2016-01459; 73 pages [032] (Dated Apr. 4, 2019).

\* cited by examiner

HAND WAND FOR ULTRASONIC COSMETIC TREATMENT AND IMAGING

CROSS-REFERENCE TO RELATED APPLICATIONS

This application is a U.S. National Phase under 35 U.S.C. § 371 of International Application No. PCT/US2009/046475, filed on Jun. 5, 2009 and published in English on Dec. 10, 2009, which claims the benefit of priority from U.S. Provisional No. 61/059,477 filed Jun. 6, 2008, which is incorporated in its entirety by reference, herein.

BACKGROUND

Embodiments of the present invention generally relate to ultrasound treatment and imaging devices and more specifically relate to ultrasound devices having a transducer probe operable to emit and receive ultrasound energy for cosmetic treatment and imaging.

In general, a popular cosmetic procedure for reducing wrinkles on the brow region of a patient's face is a brow lift, during which portions of muscle, fat, fascia and other tissues in the brow region are invasively cut, removed, and/or paralyzed to help reduce or eliminate wrinkles from the brow. Traditionally, the brow lift requires an incision beginning at one ear and continuing around the forehead at the hair line to the other ear. A less invasive brow lift procedure is known as an endoscopic lift during which smaller incisions are made along the forehead and an endoscope and surgical cutting tools are inserted within the incisions to cut, remove, manipulate, or paralyze tissue to reduce or eliminate wrinkles from the brow.

Even less invasive cosmetic treatments are designed to inject a neurotoxin in the brow. This procedure paralyzes muscles within the brow which can assist in reducing wrinkles. However, such procedures are temporary, can require chronic usage to sustain the intended effects, and can have deleterious effects.

SUMMARY

There is a need for non-invasive cosmetic procedures for reducing wrinkles in the head and neck, such as in a brow region, and in other regions. In addition, there is a need for non-invasive cosmetic procedures that result in a tightening of skin in the head and neck, including the brow region, and other regions. Further, there is a need to effectively and efficiently image the region of the skin that is targeted for treatment. In several of the embodiments described herein, the procedure is entirely cosmetic and not a medical act.

Accordingly, several embodiments of the present invention provide a system and method for cosmetic treatment and imaging. In various embodiments the treatment system includes a hand wand with at least one finger activated control, or controller, and a removable transducer module having at least one ultrasound transducer. In one embodiment, the system includes a control module that is coupled to the hand wand and has a graphic user interface for controlling the removable transducer module that has an interface coupling the hand wand to the control module. In an aspect of the embodiment, the interface provides power to the hand wand and/or transfers a signal from the hand wand to the control module. In various embodiments of the present invention, the cosmetic treatment and imaging system is used in aesthetic procedures on a portion of a head of patient, including the face, scalp, neck and/or ears of a patient.

In accordance with one embodiment of an aesthetic imaging system, the aesthetic imaging system includes a hand wand, a removable transducer module, a control module, and an interface coupling the hand wand and the control module. The hand wand includes at least one finger activated controller. The removable transducer module includes an ultrasound transducer and at least one interface coupleable to the hand wand. The control module is coupled to the hand wand and includes a graphical user interface for controlling the removable transducer module. In one embodiment, the interface couples the hand wand to the control module, and provides at least power to the hand wand. In one embodiment, the interface transfers one or more signals between the hand wand and the control module. In one embodiment, at least one signal (e.g., 1, 2, 3, 4, 5 or more signals) is communicated from the wand to the control module. In another embodiment, at least one signal (e.g., 1, 2, 3, 4, 5 or more signals) is communicated from the control module to the wand. In several embodiments, at least one signal (e.g., 1, 2, 3, 4, 5 or more signals) is communicated to, from, or between the wand and control module. In one embodiment, the aesthetic imaging system also includes a printer coupled to the control module and the control module provides an output signal and power to the printer. In one embodiment, the aesthetic imaging system also includes a key operable to unlock the control module for controlling the removable transducer module. In one embodiment of an aesthetic imaging system, the hand wand includes a movement mechanism, operable to move the ultrasound transducer within the transducer module. In one embodiment, the aesthetic imaging system also includes at least one sensor coupled to the hand wand and/or the removable transducer module.

In accordance with one embodiment of a hand wand for use in cosmetic treatment, the wand includes a first controlling device operably controlling an imaging function, a second controlling device operably controlling a treatment function, a status indicator, an input for power, an output for at least one signal, a movement mechanism and a removable transducer module operably coupled to at least one of the first controlling device, the second controlling device and the movement mechanism. In one embodiment, the hand wand includes a latch mechanism removably holding the transducer module in the wand. In one embodiment, the hand wand includes a cable for communicating at least one of the input and the output. In one embodiment, the hand wand includes a controller operably interfacing with a cable, where the controller has a graphical user interface for controlling the removable transducer module. In one embodiment, the hand wand includes a first transducer module coupled to the first controlling device and a second transducer module coupled to the second controlling device.

In accordance with one embodiment of a device for cosmetic imaging and treatment, the device includes a removable transducer module and a controller. In one embodiment, the transducer module is not removable. In one embodiment, the transducer module is integrated, or permanently attached. The removable transducer module is interfaced to a hand enclosure having at least one controller button such that the transducer module and button is operable using one hand. The transducer module provides ultrasound energy for at least one of an imaging function and a treatment function. The controller is coupled to the hand enclosure and is interfaced to the transducer module. The controller controls the ultrasound energy and receives at least one signal from the transducer module. The controller has a power supply operably providing power for at least the ultrasound energy. In one embodiment, the device also includes a graphical user interface for controlling the transducer module and for viewing the at least one signal from the transducer module. In one embodiment, the device has a hand enclosure that also includes a movement mechanism operably moving a transducer in the transducer module, where the movement mechanism is controlled by the controller. In one embodiment, the device has at least one controller button as a first controller button controlling the imaging function and a second controlling button controlling the treatment function. In various embodiments, the device has a treatment function that is one of face lift, a brow lift, a chin lift, a wrinkle reduction, a scar reduction, a tattoo removal, a vein removal, sun spot removal, and pimple removal. In another embodiment the device may be used on adipose tissue.

In accordance with one embodiment of a method of performing cosmetic treatment on a facial (or other) area of a subject, the method includes inserting a transducer module into a hand controller, coupling the transducer module to the subject, activating a first switch on the hand controller operably initiating an imaging sequence of a portion of tissue below the dermal layer, collecting data from the imaging sequence, calculating a treatment sequence from the data, and activating a second switch on the hand controller operably initiating the treatment sequence. In one embodiment, the method also includes emitting a first ultrasound energy from a first transducer in the transducer module operably providing a source for the imaging sequence. In one embodiment, the method also includes emitting a second ultrasound energy from a second transducer in the transducer module operably providing a source for the treatment sequence. In one embodiment, the method also includes tightening a portion of the dermal layer on a facial area of a subject. In one embodiment, the method provides for the transducer module to permit the treatment sequence at a fixed depth below the dermal layer.

In accordance with one embodiment of a hand wand for use in cosmetic treatment, the wand includes a first controlling device operably controlling an ultrasonic imaging function, a second controlling device operably controlling an ultrasonic treatment function, a movement mechanism configured for travel through a liquid-tight seal, and a fluid-filled transducer module. In one embodiment, the fluid-filled transducer module is operably coupled to at least one of the first controlling, the second controlling device and the movement mechanism. In one embodiment, the fluid-filled transducer module is mechanically and electrically separable from at least one of the first controlling, the second controlling device and the movement mechanism. In one embodiment, the fluid-filled transducer module includes an acoustic liquid. In one embodiment, the fluid-filled transducer module includes a gel adapted to enhance transmission of an ultrasonic signal. In one embodiment, a gel adapted to enhance transmission of an ultrasonic signal is placed between the transducer and the patient's skin.

In accordance with one embodiment of a hand wand for use in cosmetic treatment, the wand includes a first controlling device operably controlling an ultrasonic imaging function, a second controlling device operably controlling an ultrasonic treatment function, and a movement mechanism configured to create a linear sequence of individual thermal lesions with the second controlling device. In one embodiment, the movement mechanism is configured to be automated and programmable by a user. In one embodiment, the wand includes a transducer module operably coupled to at least one of the first controlling device, the second controlling device and the movement mechanism. In one embodiment, the linear sequence of individual thermal lesions has a treatment spacing in a range from about 0.01 mm to about 25 mm. In one embodiment, the movement mechanism is configured to be programmed to provide variable spacing between the individual thermal lesions. In one embodiment the individual thermal lesions are discrete. In one embodiment the individual thermal lesions are overlapping.

In accordance with one embodiment of a variable ultrasonic parameter ultrasonic system for use in cosmetic treatment, the system includes a first controlling device, a second controlling device, a movement mechanism, and one or more removable transducer modules. In various embodiments, the one or more removable transducer modules includes two, three, four, five, six, or more removable transducer modules. In various embodiments, the different numbers of removable transducer modules can be configured for different or variable ultrasonic parameters. For example, in various non-limiting embodiments, the ultrasonic parameter can relate to transducer geometry, size, timing, spatial configuration, frequency, variations in spatial parameters, variations in temporal parameters, coagulation formation, depth, width, absorption coefficient, refraction coefficient, tissue depths, and/or other tissue characteristics. In various embodiments, a variable ultrasonic parameter may be altered, or varied, in order to effect the formation of a lesion for the desired cosmetic approach. In various embodiments, a variable ultrasonic parameter may be altered, or varied, in order to effect the formation of a lesion for the desired clinical approach. By way of example, one variable ultrasonic parameter relates to aspects of configurations associated with tissue depth. For example, some non-limiting embodiments of removable transducer modules can be configured for a tissue depth of 3 mm, 4.5 mm, 6 mm, less than 3 mm, between 3 mm and 4.5 mm, more than more than 4.5 mm, more than 6 mm, and anywhere in the ranges of 0-3 mm, 0-4.5 mm, 0-25 mm, 0-100 mm, and any depths therein. In one embodiment, an ultrasonic system is provided with two transducer modules, in which the first module applies treatment at a depth of about 4.5 mm and the second module applies treatment at a depth of about 3 mm. An optional third module that applies treatment at a depth of about 1.5-2 mm is also provided. A combination of two or more treatment modules is particularly advantageous because it permits treatment of a patient at varied tissue depths, thus providing synergistic results and maximizing the clinical results of a single treatment session. For example, treatment at multiple depths under a single surface region permits a larger overall volume of tissue treatment, which results in enhanced collagen formation and tightening. Additionally, treatment at different depths affects different types of tissue, thereby producing different clinical effects that together provide an enhanced overall cosmetic result. For example, superficial treatment may reduce the visibility of wrinkles and deeper treatment may induce formation of more collagen growth.

Although treatment of a subject at different depths in one session may be advantageous in some embodiments, sequential treatment over time may be beneficial in other embodiments. For example, a subject may be treated under the same surface region at one depth in week 1, a second depth in week 2, etc. The new collagen produced by the first treatment may be more sensitive to subsequent treatments, which may be desired for some indications. Alternatively, multiple depth treatment under the same surface region in a single session may be advantageous because treatment at one depth may synergistically enhance or supplement treatment at another depth (due to, for example, enhanced blood flow, stimulation of growth factors, hormonal stimulation, etc.).

In several embodiments, different transducer modules provide treatment at different depths. In several embodiments, a system comprising different transducers, each having a different depth, is particularly advantageous because it reduces the risk that a user will inadvertently select an incorrect depth. In one embodiment, a single transducer module can be adjusted or controlled for varied depths. Safety features to minimize the risk that an incorrect depth will be selected can be used in conjunction with the single module system.

In several embodiments, a method of treating the lower face and neck area (e.g., the submental area) is provided. In several embodiments, a method of treating (e.g., softening) mentolabial folds is provided. In other embodiments, a method of treating the eye region is provided. Upper lid laxity improvement and periorbital lines and texture improvement will be achieved by several embodiments by treating at variable depths. In one embodiment, a subject is treated with about 40-50 lines at depths of 4.5 and 3 mm. The subject is optionally treated with about 40-50 lines at a depth of about 1.5-2 mm. The subject is optionally treated with about 40-50 lines at a depth of about 6 mm. By treating at varied depths in a single treatment session, optimal clinical effects (e.g., softening, tightening) can be achieved.

In several embodiments, the treatment methods described herein are non-invasive cosmetic procedures. In some embodiments, the methods can be used in conjunction with invasive procedures, such as surgical facelifts or liposuction, where skin tightening is desired.

In accordance with one embodiment of a variable ultrasonic parameter system for use in cosmetic treatment, the system includes a first controlling device, a second controlling device, a movement mechanism, a first removable transducer module and a second removable transducer module. The first controlling device operably controls an ultrasonic imaging function. The second controlling device operably controls an ultrasonic treatment function. The movement mechanism is configured to create a linear sequence of individual thermal lesions for treatment purposes. The first removable transducer module is configured to treat tissue at a first tissue depth. The second removable transducer module is configured to treat tissue at a second tissue depth. The first and second transducer modules are interchangeably coupled to a hand wand. The first and second transducer modules are operably coupled to at least one of the first controlling device, the second controlling device and the movement mechanism. Rapid interchangeability and exchange of multiple modules on a single unit facilitates treatment in several embodiments. In one embodiment the individual thermal lesions are discrete. In one embodiment the individual thermal lesions are overlapping, merged, etc.

In accordance with one embodiment of an aesthetic imaging and treatment system includes a hand wand, a removable transducer module, a control module and an interface coupling the hand wand to the control module. The hand wand includes at least one finger activated controller. The removable transducer module includes an ultrasound transducer and at least one interface coupleable to the hand wand. The control module is coupled to the hand wand and includes a graphical user interface for controlling the removable transducer module. The interface coupling the hand wand to the control module transfers at least a signal between the hand wand and the control module. In one embodiment, the system also includes a printer coupled to the control module, with the control module providing an output signal and power to the printer. In one embodiment, the system also includes a key operable to unlock the control module for controlling the removable transducer module. In one embodiment, the hand wand also includes a movement mechanism, the movement mechanism operable to move the ultrasound transducer within the transducer module. In one embodiment, the system also includes at least one sensor coupled to one of the hand wand and the removable transducer module.

In accordance with one embodiment of a hand wand for use in cosmetic treatment, the wand includes a first controlling device operably controlling an imaging function, a second controlling device operably controlling a treatment function, a status indicator, an input for power, an output for at least one signal, a movement mechanism, and a removable transducer module operably coupled to at least one of the first controlling device, the second controlling device and the movement mechanism. In one embodiment, the system also includes a latch mechanism removably holding the transducer module in the wand. In one embodiment, the system also includes a cable for communicating at least one of the input and the output. In one embodiment, the system also includes a controller operably interfacing with the cable, the controller having a graphical user interface for controlling the removable transducer module. In one embodiment, the transducer module has a first transducer coupled to the first controlling device and a second transducer coupled to the second controlling device.

In accordance with one embodiment of a device for cosmetic treatment, the device includes a removable transducer module interfaced to a hand enclosure and a controller coupled to the hand enclosure and interfaced to the transducer module. The removable transducer module has at least one controller button such that the transducer module and button are operable using one hand. The transducer module provides ultrasound energy for a treatment function. The controller controls the ultrasound energy and receives at least one signal from the transducer module. The controller has a power supply operably providing power for at least the ultrasound energy. In one embodiment, the controller also includes a graphical user interface for controlling the transducer module and for viewing the at least one signal from the transducer. In one embodiment, the hand enclosure also includes a movement mechanism operably moving a transducer in the transducer module, the movement mechanism being controlled by the controller. In one embodiment, the at least one controller button includes a first controller button controlling the imaging function and a second controlling button controlling the treatment function. In one embodiment, the treatment function is at least one of face lift, a brow lift, a chin lift, a wrinkle reduction, a scar reduction, a tattoo removal, a vein removal, sun spot removal, and acne treatment In accordance with one embodiment of a method of performing cosmetic treatment a facial area of a subject, the method includes inserting a transducer module into a hand controller, coupling the transducer module to the facial area of the subject, activating a first switch on the hand controller operably initiating an imaging sequence of a portion of tissue below the dermal layer, collecting data from the imaging sequence, calculating a treatment sequence from the data, and activating a second switch on the hand controller operably initiating the treatment sequence. In one embodiment, the method also includes emitting a first ultrasound energy from a first transducer in the transducer module operably providing a source for the imaging sequence. In one embodiment, the method also includes emitting a second ultrasound energy from a second transducer in the transducer module operably providing a source for the treatment sequence. In one embodiment, the method also includes tightening a portion of the dermal layer on a facial area of a subject. In one embodiment, the transducer module permits the treatment sequence at a fixed depth below the dermal layer.

In several embodiments, the invention comprises a hand wand for use in cosmetic treatment. In one embodiment, the wand comprises a first controlling device operably controlling an ultrasonic imaging function for providing ultrasonic imaging and a second controlling device operably controlling an ultrasonic treatment function for providing ultrasonic treatment. The controlling devices, in some embodiments, are finger/thumb operated buttons or keys that communicate with a computer processor. The wand also comprises a movement mechanism configured to direct ultrasonic treatment in a linear sequence of individual thermal lesions. In one embodiment, the linear sequence of individual thermal lesions has a treatment spacing in a range from about 0.01 mm to about 25 mm. In one embodiment the individual thermal lesions are discrete. In one embodiment the individual thermal lesions are overlapping. The movement mechanism is configured to be programmed to provide variable spacing between the individual thermal lesions. First and second removable transducer modules are also provided. Each of the first and second transducer modules are configured for both ultrasonic imaging and ultrasonic treatment. The first and second transducer modules are configured for interchangeable coupling to the hand wand. The first transducer module is configured to apply ultrasonic therapy to a first layer of tissue, while the second transducer module is configured to apply ultrasonic therapy to a second layer of tissue. The second layer of tissue is at a different depth than the first layer of tissue. The first and second transducer modules are configured to be operably coupled to at least one of the first controlling device, the second controlling device and the movement mechanism.

In one embodiment, a third transducer module is provided. The third transducer module is configured to apply ultrasonic therapy to a third layer of tissue, wherein the third layer of tissue is at a different depth than the first or second layers of tissue. Fourth and fifth modules are provided in additional embodiments. The transducer modules are configured to provide variable depth treatment and the movement mechanism is configured to provide variable treatment along a single depth level.

In one embodiment, at least one of the first controlling device and the second controlling device is activated by a control. The control module comprises a processor and a graphical user interface for controlling the first and second transducer modules.

A method of performing a cosmetic procedure on a subject using a hand wand as described herein is provided in several embodiments. In one embodiment, the method comprises ultrasonically imaging a first target region on the subject with the first transducer module and ultrasonically treating the first target region on the subject with the first transducer module at the first tissue depth. The treatment comprises multiple treatment lines across the first target region that are automatically selected (e.g., programmed, pre-set, etc.) by the movement mechanism. In one embodiment, the method further comprises exchanging the first transducer module with the second transducer module; ultrasonically imaging a second target region on the subject with the second transducer module; and ultrasonically treating the second target region on the subject with the second transducer module at the second tissue depth. The treatment comprises multiple treatment lines across the second target region that are automatically selected (e.g., programmed, pre-set, etc.) by the movement mechanism. In one embodiment, the first and second target regions are located under a single surface of the subject.

In several embodiments, the invention comprises a hand wand for use in cosmetic treatment. In accordance with one embodiment, the hand wand comprises a first controlling device, a second controlling device, a movement mechanism, and a transducer module. The first controlling device operably controls an ultrasonic imaging function for providing ultrasonic imaging. The second controlling device operably controls an ultrasonic treatment function for providing ultrasonic treatment. The movement mechanism is configured to direct ultrasonic treatment in a sequence of individual thermal lesions. The removable transducer module is configured for both ultrasonic imaging and ultrasonic treatment. The removable transducer module is configured for interchangeable coupling to the hand wand. The removable transducer module is configured to be operably coupled to at least one of said first controlling device, said second controlling device and said movement mechanism. The removable transducer module is configured to apply ultrasonic therapy to at a first variable ultrasonic parameter to tissue.

In one embodiment, the hand wand is configured to apply ultrasonic therapy to at a second variable ultrasonic parameter to tissue. In one embodiment, the removable transducer module is configured to apply ultrasonic therapy to at a second variable ultrasonic parameter to tissue. In one embodiment, the hand wand further comprises a second removable transducer module, wherein the second removable transducer module is configured to apply ultrasonic therapy to at the second variable ultrasonic parameter to tissue. In one embodiment, the variable ultrasonic parameter is tissue depth. In one embodiment, the variable ultrasonic parameter is frequency. In one embodiment, the variable ultrasonic parameter is timing. In one embodiment, the variable ultrasonic parameter is geometry.

In several embodiments, the invention comprises a hand wand for use in cosmetic treatment. In one embodiment, the wand comprises at least one controlling device, movement mechanism and transducer module. In one embodiment, the wand comprises at least one controlling device operably controlling an ultrasonic imaging function for providing ultrasonic imaging and operably controlling an ultrasonic treatment function for providing ultrasonic treatment. One, two or more controlling devices may be used. A movement mechanism configured to direct ultrasonic treatment in a sequence of individual thermal lesions is provided. The transducer module is configured for both ultrasonic imaging and ultrasonic treatment and is operably coupled to at least one controlling device and a movement mechanism. The transducer module is configured to apply ultrasonic therapy at a first ultrasonic parameter and a second ultrasonic parameter. In various embodiments, the first and second ultrasonic parameters are selected from the group consisting of: variable depth, variable frequency, and variable geometry. For example, in one embodiment, a single transducer module delivers ultrasonic therapy at two or more depths. In another embodiment, two or more interchangeable transducer modules each provide a different depth (e.g., one module treats at 3 mm depth while the other treats at a 4.5 mm depth). In yet another embodiment, a single transducer module delivers ultrasonic therapy at two or more frequencies, geometries, amplitudes, velocities, wave types, and/or wavelengths. In other embodiments, two or more interchangeable transducer modules each provide a different parameter value. In one embodiment, a single transducer may provide at least two different depths and at least two different frequencies (or other parameter). Variable parameter options are particularly advantageous in certain embodiments because they offer enhanced control of tissue treatment and optimize lesion formation, tissue coagulation, treatment volume, etc.

Further areas of applicability will become apparent from the description provided herein. It should be understood that the description and specific examples are intended for purposes of illustration only and are not intended to limit the scope of the embodiments disclosed herein.

BRIEF DESCRIPTION OF THE DRAWINGS

The drawings described herein are for illustration purposes only and are not intended to limit the scope of the present disclosure in any way. Embodiments of the present invention will become more fully understood from the detailed description and the accompanying drawings wherein.

DETAILED DESCRIPTION OF THE PREFERRED EMBODIMENT

Figure 1:
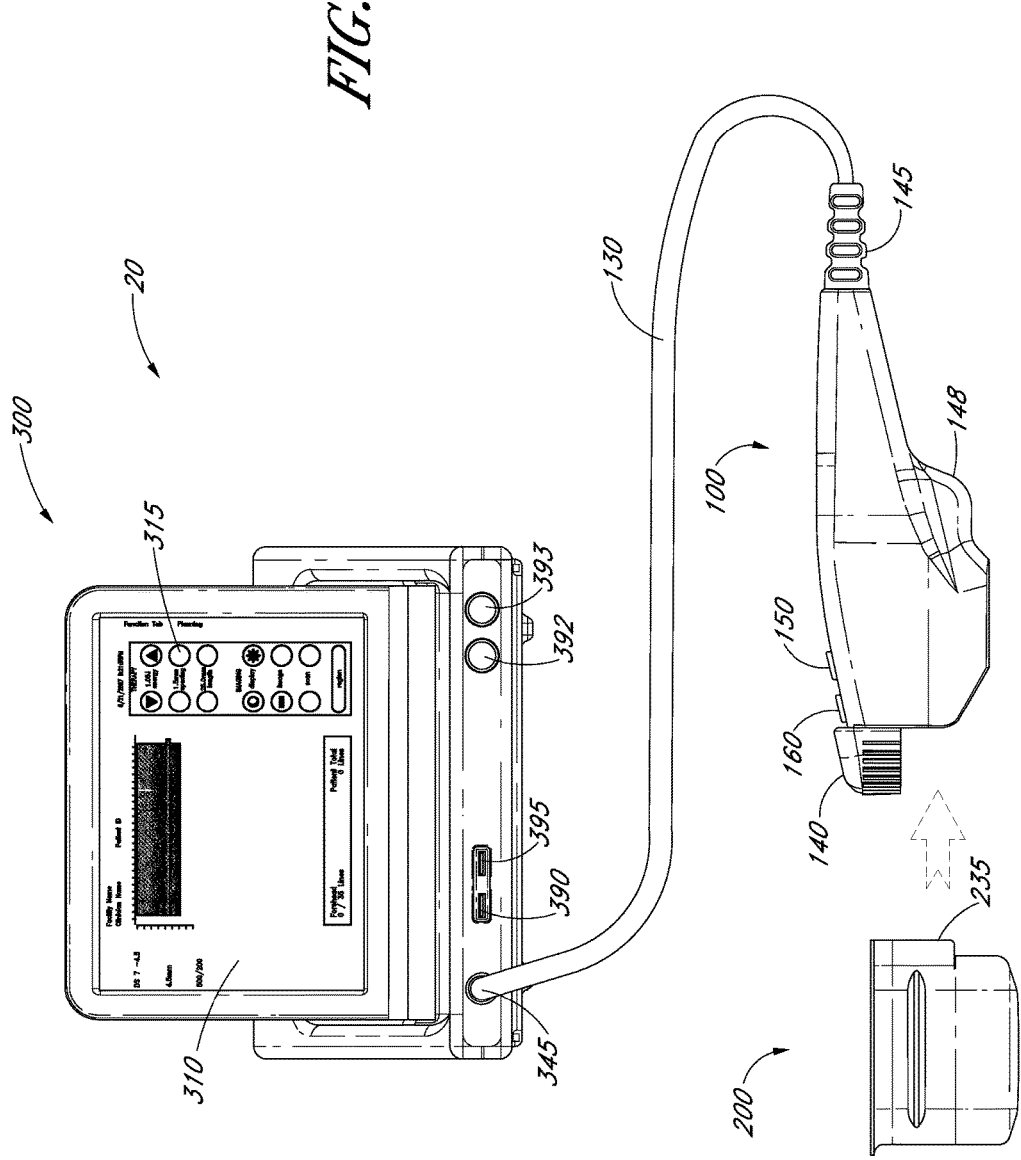
FIG. 1 is an illustration depicting a cosmetic treatment system according to various embodiments of the present invention.

The following description sets forth examples of embodiments, and is not intended to limit the present invention or its teachings, applications, or uses thereof. It should be understood that throughout the drawings, corresponding reference numerals indicate like or corresponding parts and features. The description of specific examples indicated in various embodiments of the present invention are intended for purposes of illustration only and are not intended to limit the scope of the invention disclosed herein. Moreover, recitation of multiple embodiments having stated features is not intended to exclude other embodiments having additional features or other embodiments incorporating different combinations of the stated features. Further, features in one embodiment (such as in one figure) may be combined with descriptions (and figures) of other embodiments.

In accordance with on embodiment of the present invention, methods and systems for ultrasound treatment of tissue are configured to provide cosmetic treatment. In various embodiments of the present invention, tissue below or even at a skin surface such as epidermis, dermis, fascia, and superficial muscular aponeurotic system ("SMAS"), are treated non-invasively with ultrasound energy. The ultrasound energy can be focused, unfocused or defocused and applied to a region of interest containing at least one of epidermis, dermis, hypodermis, fascia, and SMAS to achieve a therapeutic effect. In one embodiment, the present invention provides non-invasive dermatological treatment to produce eyebrow lift through tissue coagulation and tightening. In one embodiment, the present invention provides imaging of skin and sub-dermal tissue. Ultrasound energy can be focused, unfocused or defocused, and applied to any desired region of interest, including adipose tissue. In one embodiment, adipose tissue is specifically targeted.

In various embodiments of the present invention, certain cosmetic procedures that are traditionally performed through invasive techniques are accomplished by targeting energy, such as ultrasound energy, at specific subcutaneous tissues. In several embodiments, methods and systems for non-invasively treating subcutaneous tissues to perform a brow lift are provided; however, various other cosmetic treatment applications, such as face lifts, acne treatment and/or any other cosmetic treatment application, can also be performed with the cosmetic treatment system. In one embodiment, a system integrates the capabilities of high resolution ultrasound imaging with that of ultrasound therapy, providing an imaging feature that allows the user to visualize the skin and sub-dermal regions of interest before treatment. In one embodiment, the system allows the user to place a transducer module at optimal locations on the skin and provides feedback information to assure proper skin contact. In one embodiment, the therapeutic system provides an ultrasonic transducer module that directs acoustic waves to the treatment area. This acoustic energy heats tissue as a result of frictional losses during energy absorption, producing a discrete zone of coagulation.

In various embodiments, the device includes a removable transducer module interfaced to a hand enclosure having at least one controller button such that the transducer module and the controller button is operable using only one hand. In an aspect of the embodiments, the transducer module provides ultrasound energy for an imaging function and/or a treatment function. In another aspect of the embodiments, the device includes a controller coupled to the hand-held enclosure and interfaced to the transducer module. In a further aspect of the embodiments, the controller controls the ultrasound energy and receives a signal from the transducer module. The controller can have a power supply and driver circuits providing power for the ultrasound energy. In still another aspect of the embodiments, the device is used in cosmetic imaging and treatment of a patient, or simply treatment of the patient, such as on a brow of a patient.

In accordance with one embodiment for a method of performing a brow lift on a patient, the method includes coupling a probe to a brow region of the patient and imaging at least a portion of subcutaneous tissue of the brow region to determine a target area in the subcutaneous tissue. In one embodiment, the method includes administering ultrasound energy into the target area in the subcutaneous tissue to ablate or coagulate the subcutaneous tissue in the target area, which causes tightening of a dermal layer above or below the subcutaneous tissue of the brow region.

Moreover, several embodiments of the present invention provide a method of tightening a portion of a dermal layer on a facial area of a patient. In various embodiments, the method includes inserting a transducer module into a hand controller and then coupling the transducer module to a facial area of the patient. In one embodiment, the method includes activating a first switch on the hand to initiate an imaging sequence of a portion of tissue below a dermal layer, then collecting data from the imaging sequence. In these embodiments, the method includes calculating a treatment sequence from the collected data, and then activating a second switch on the hand to initiate the treatment sequence. In an aspect of the embodiments, the method can be useful on a portion of a face, head, neck and/or other part of the body of a patient.

In some embodiments, the system includes a hand wand with at least one finger activated controller, and a removable transducer module having an ultrasound transducer. In one embodiment, the system includes a control module that is coupled to the hand wand and has a graphic user interface for controlling the removable transducer module with an interface coupling the hand wand to the control module. In one embodiment, the interface provides power to the hand wand. In one embodiment, the interface transfers at least one signal between the hand wand and the control module. In one embodiment, the aesthetic imaging system is used in cosmetic procedures on a portion of a face, head, neck and/or other part of the body of a patient.

In addition, several embodiments of the present invention provide a hand wand for use in aesthetic treatment. In some embodiments, the hand wand includes a first controlling device operably controlling an imaging function, a second controlling device operably controlling a treatment function, a status indicator, an input for power, an output for at least one signal, and a movement mechanism. A removable transducer module can be coupled to the hand wand. The removable transducer module can be interfaced with the first controlling device, the second controlling device and/or the movement mechanism. In one embodiment, the hand wand is used in cosmetic procedures on a face, head, neck and/or other part of the body of a patient.

Several embodiments of the present invention may be described herein in terms of various components and processing steps. It should be appreciated that such components and steps may be realized by any number of hardware components configured to perform the specified functions. For example, some embodiments of the present invention may employ various medical treatment devices, visual imaging and display devices, input terminals and the like, which may carry out a variety of functions under the control of one or more control systems or other control devices. Several embodiments of the present invention may be practiced in any number of medical contexts. For example, the principles, features and methods discussed may be applied to any medical application.

To further explain in more detail various aspects of embodiments of the present invention, several examples of a cosmetic treatment system as used with a control system and an ultrasonic probe system will be provided. However, it should be noted that the following embodiments are for illustrative purposes, and that embodiments of the present invention can comprise various other configurations for a cosmetic treatment. In addition, although not illustrated in the drawing figures, the cosmetic treatment system can further include components associated with imaging, diagnostic, and/or treatment systems, such as any required power sources, system control electronics, electronic connections, and/or additional memory locations.

With reference to the illustration in FIG. 1, an embodiment of the present invention is depicted as a cosmetic treatment system 20. In various embodiments of the present invention, the cosmetic treatment system 20 (hereinafter "CTS 20") includes a hand wand 100, an emitter-receiver module 200, and a controller 300. The hand wand 100 can be coupled to the controller 300 by an interface 130. In one embodiment the interface is a cord. In one embodiment, the cord is a two way interface between the hand wand 100 and the controller 300. In various embodiments the interface 130 can be, for example, any multi-conductor cable or wireless interface. In one embodiment, the interface 130 is coupled to the hand wand 100 by a flexible connection 145. In one embodiment, the flexible connection 145 is a strain relief. The distal end of the interface 130 is connected to a controller connector on a flex circuit 345. In various embodiments the flexible connector 145 can be rigid or may be flexible, for example, including a device such as an elastomeric sleeve, a spring, a quick connect, a reinforced cord, a combination thereof, and the like. In one embodiment, the flexible connection 145 and the controller connection on the flex circuit 345 can include an antenna and receiver for communications wirelessly between the hand wand 100 and the controller 300. In one embodiment, the interface 130 can transmit controllable power from the controller 300 to the hand wand 100.

In various embodiments, the controller 300 can be configured for operation with the hand wand 100 and the emitter-receiver module 200, as well as the overall CTS 20 functionality. In various embodiments, multiple controllers 300, 300', 300", etc. can be configured for operation with multiple hand wands 100, 100', 100", etc. and or multiple emitter-receiver modules 200, 200', 200", etc. In various embodiments, a second embodiment of a reference can be indicated with a reference number with one or more primes (`'`). For example, in one embodiment a first module 200 may be used with or as an alternative to a second module 200', third module 200", fourth module 200''', etc. Likewise, in various embodiments, any part with multiples can have a reference number with one or more primes attached to the reference number in order to indicate that embodiment. For example, in one embodiment a first transducer 280 can be indicated with the 280 reference number, and a second transducer 280' uses the prime. In one embodiment, controller 300 houses an interactive graphical display 310, which can include a touch screen monitor and Graphic User Interface (GUI) that allows the user to interact with the CTS 20. In various embodiments, this display 310 sets and displays the operating conditions, including equipment activation status, treatment parameters, system messages and prompts and ultrasound images. In various embodiments, the controller 300 can be configured to include, for example, a microprocessor with software and input/output devices, systems and devices for controlling electronic and/or mechanical scanning and/or multiplexing of transducers and/or multiplexing of transducer modules, a system for power delivery, systems for monitoring, systems for sensing the spatial position of the probe and/or transducers and/or multiplexing of transducer modules, and/or systems for handling user input and recording treatment results, among others. In various embodiments, the controller 300 can comprise a system processor and various digital control logic, such as one or more of microcontrollers, microprocessors, field-programmable gate arrays, computer boards, and associated components, including firmware and control software, which may be capable of interfacing with user controls and interfacing circuits as well as input/output circuits and systems for communications, displays, interfacing, storage, documentation, and other useful functions. System software may be capable of controlling all initialization, timing, level setting, monitoring, safety monitoring, and all other system functions required to accomplish user-defined treatment objectives. Further, the controller 300 can include various control switches that may also be suitably configured to control operation of the CTS 20. In one embodiment, the controller 300 includes an interactive graphical display 310 for conveying information to user. In one embodiment, the controller 300 includes one or more data ports 390. In one embodiment, the data port 390 is a USB port, and can be located on the front, side, and/or back of the controller 300 for access to storage, a printer 391, devices, or be used for other purposes. In various embodiments the CTS 20 includes a lock 395, and in one embodiment the lock 395 can be connectable to the controller 300 via a USB port. In one embodiment, in order to operate CTS 20, lock 395 must be unlocked so that power switch 393 may be activated. In another embodiment lock 395 must be unlocked insertion of USB access key or hardware dongle and associated software so that the interactive graphical display 310 can execute. In one embodiment, an emergency stop button 392 is readily accessible for emergency deactivation.

In various embodiments, an aesthetic imaging system or CTS 20 includes a hand wand 100 with at least one finger activated controller (150 and/or 160), and a removable emitter-receiver module 200 having an ultrasound transducer. Other embodiments may include non-removable emitter-receiver modules, imaging-only emitter-receiver modules, treatment-only emitter-receiver modules, and imaging-and-treatment emitter-receiver modules. In one embodiment, the CTS 20 includes a control module 300 that is coupled to the hand wand 100 and has a graphic user interface 310 for controlling the removable transducer module 200 with an interface 130, such as in one embodiment, a cord coupling the hand wand 100 to the control module 300. In one embodiment, the interface 130 provides power to the hand wand 100. In one embodiment, the interface 130 transfers at least one signal between the hand wand 100 and the control module 300. In an aspect of this embodiment, the aesthetic imaging system of CTS 20 is used in aesthetic procedures on a portion of a head of a patient. In one embodiment, the CTS 20 is used in aesthetic procedures on a portion of a face, head, neck and/or other part of the body of a patient.

In addition, certain embodiments of the present invention provide a hand wand 100 for use in aesthetic treatment. In some embodiments, the hand wand 100 includes a first controlling device 150 operably controlling an imaging function, a second controlling device 160 operably controlling a treatment function, a status indicator 155, an input for power, an output for at least one signal (for example to a controller 300), a movement mechanism 400, and a removable transducer module 200 in communication with the first controlling device 150, the second controlling device 160 and/or the movement mechanism 400. In an aspect of the embodiments, the hand wand 100 is used in cosmetic procedures on a face, head, neck and/or other part of the body of a patient.

In accordance to various embodiments of the present invention, an emitter-receiver module 200 can be coupled to the hand wand 100. In some embodiments an emitter-receiver module 200 can emit and receive energy, such as ultrasonic energy. In one embodiment, an emitter-receiver module 200 can be configured to only emit energy, such as ultrasonic energy. In one embodiment, the emitter-receiver module 200 is permanently attachable to the hand wand 100. In one embodiment, the emitter-receiver module 200 is attachable to and detachable from the hand wand 100. The emitter-receiver module 200 can be mechanically coupled to the hand wand 100 using a latch or coupler 140. An interface guide 235 can be useful in assisting the coupling of the emitter-receiver module 200 to the hand wand 100. In addition, the emitter-receiver module 200 can be electronically coupled to the hand wand 100 and such coupling may include an interface which is in communication with the controller 300. In one embodiment, an electric coupler at the interface guide 235, located at a proximal end of an emitter-receiver module 200 provides for electronic communication between the emitter-receiver module 200 and the hand wand 100, which can both be in electric communication with a controller 300. The emitter-receiver module 200 can comprise various probe and/or transducer configurations. For example, the emitter-receiver module 200 can be configured for a combined dual-mode imaging/therapy transducer, coupled or co-housed imaging/therapy transducers, or simply a separate therapy probe and an imaging probe. In one embodiment, the hand wand 100 includes a handle with an integrated receptacle for insertion of an emitter-receiver module 200 containing at least a transducer on one end and an electrical cable for attachment to the controller 200 on the other end.

Figure 2:
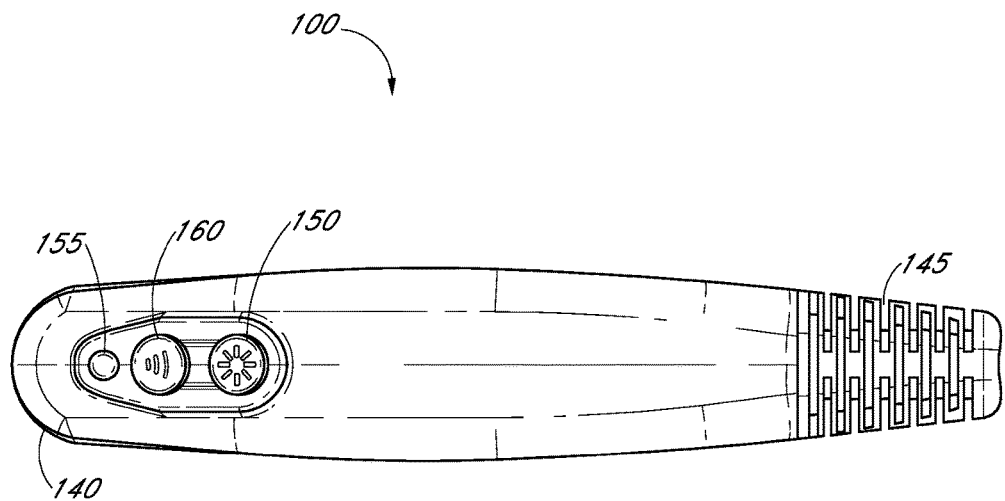
FIG. 2 is a top view illustrating a hand wand according to various embodiments of the present invention.
Figure 3:
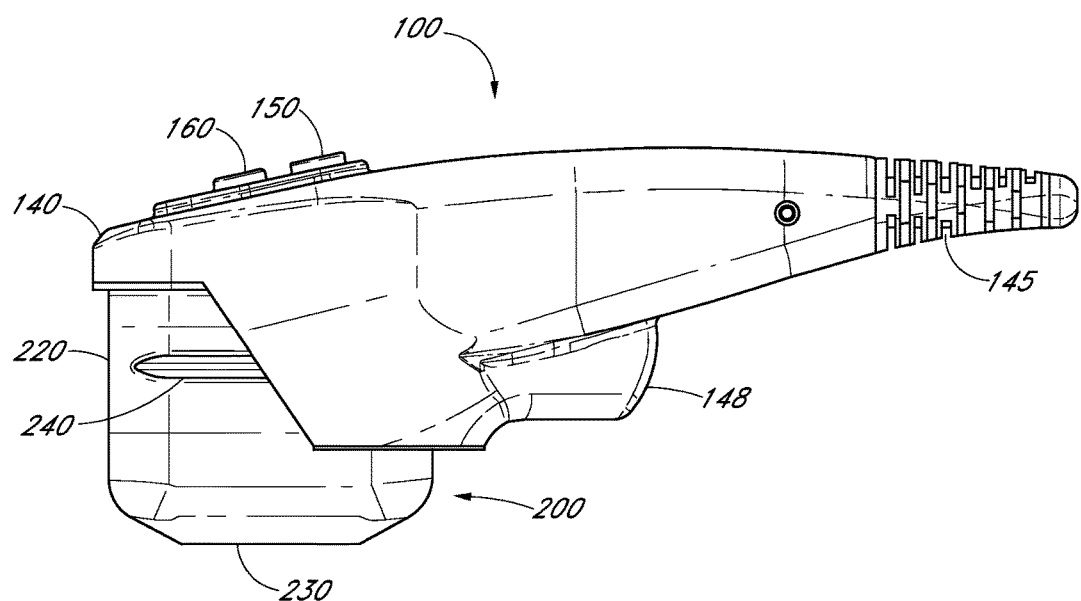
FIG. 3 is a side view illustrating a hand wand according to various embodiments of the present invention.

With additional reference to the illustrations in FIGS. 2 and 3, the hand wand 100 can be designed for ergonomic considerations to improve comfort, functionality and/or ease of use of the hand wand 100 by a user, such as, for example, a practitioner or medical professional. The hand wand 100 can be designed to be used ambidextrously. In one embodiment, the use of the hand wand 100 is not diminished by whether it is in a right hand or a left hand. In one embodiment, of the hand wand 100 includes an imaging button 150, a treatment button 160, and an indicator 155 on a top portion of the hand wand 100. Other arrangements of buttons and/or indicators are possible in various embodiments. In one embodiment the hand wand 100 includes a hand rest 148 on a bottom portion and a coupler 140 distal to the flexible connector 145. In one embodiment, the hand rest 148 includes a clearance pocket molded into the hand wand 100 housing which allows a magnet-tipped clutch rod (433 and 432 of FIG. 7) to move back and forth to drive the transducer module's rectilinear motion without hitting the hand wand's housing. According to these aspects, the hand wand 100 can be operated by the user either in a right hand or a left hand. Further to these aspects, the user can control the imaging button 150 and the treatment button 160 with a thumb or finger, such as an index finger. An interior portion of the hand wand 100 can include electronics as well as software, connections, and/or couplings for interfacing to and from the electronics. In one embodiment, the hand wand 100 contains an electronic interface 175 (not illustrated here, but see other figures) in communication with at least one of the imaging button 150 and the treatment button 160. In accordance with one embodiment, the electronic interface 175 can interface with an outside source such as, for example, the controller 300. In various embodiments, the indictor 145 can be an LED, a light, an audio signal, and combinations thereof. In one aspect of the embodiments, the indicator 155 is a LED which can change colors based on different states of the CTS 20. For example the indicator 155 can be one color (or off) in a standby mode, a second color in an imaging mode and a third color in a treatment mode.

In one embodiment, the emitter-receiver module 200 is configured to removably attach both electronically and mechanically with a hand wand 100. In one embodiment, a motion mechanism 400 (see FIG. 7) is configured to move an ultrasonic transducer 280 in an emitter-receiver module 200 such as is illustrated in various embodiments in FIGS. 4-6. A user can remove the indicated transducer module from its protective, resealable pouch, setting aside the pouch for storing the transducer module between procedures, if necessary. In one embodiment, a hand wand 100 and an emitter-receiver module 200 can be connected by pushing the coupler 140 upwards and sliding the emitter-receiver module 200 into the hand wand 100 as shown in FIG. 1. In one embodiment, when the emitter-receiver module 200 is inserted, the controller 300 automatically detects it and updates the interactive graphical display 310. In one embodiment, the emitter-receiver module 200 locked into the hand wand 100 once the emitter-receiver module 200 is fully inserted and the coupler 140 at the tip of the hand wand 100 is pushed down. To disconnect the emitter-receiver module 200, the user can lift the coupler 140 at the tip of the hand wand 100 and slide the emitter-receiver module 200 out of the hand wand 100.

Figure 4:
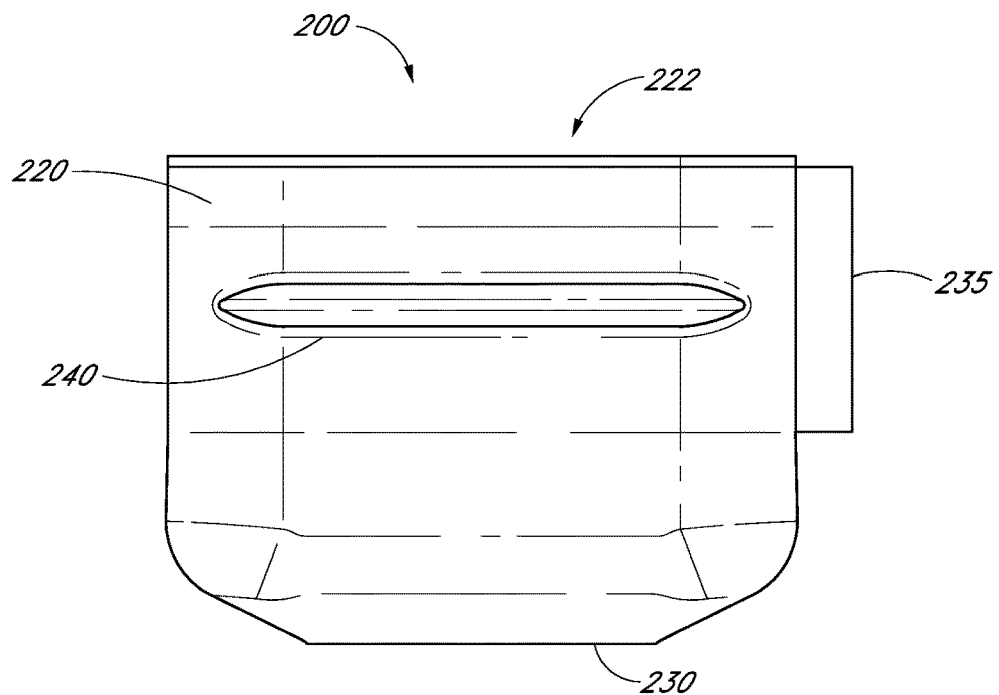
FIG. 4 is a side view illustrating an emitter-receiver module according to various embodiments of the present invention.
Figure 5:
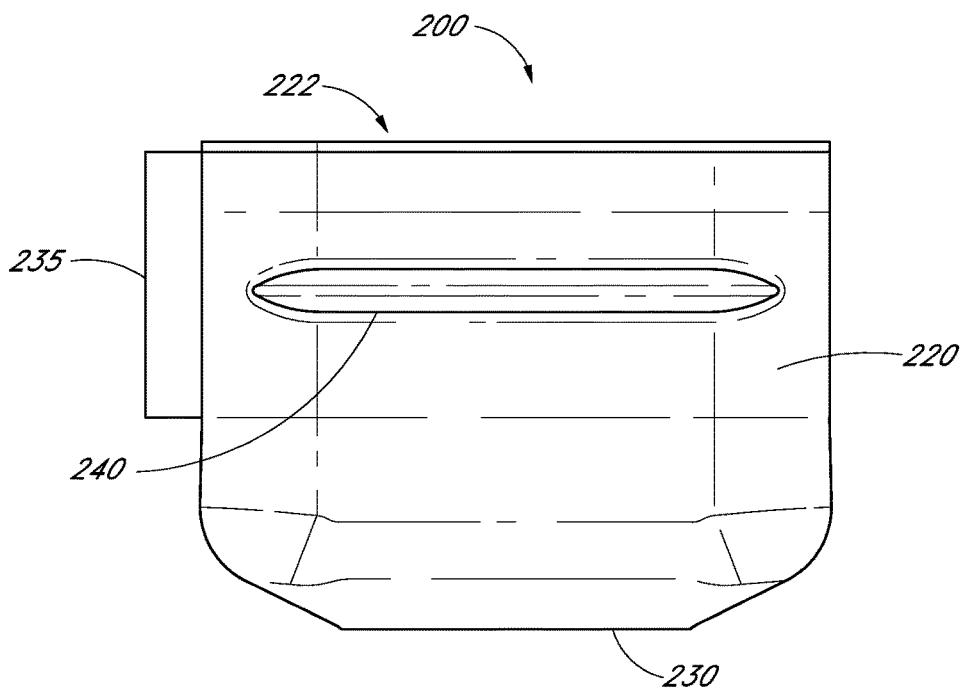
FIG. 5 is another side view illustrating an emitter-receiver module according to various embodiments of the present invention.

FIGS. 4 and 5 illustrate two opposing side views of an embodiment of an emitter-receiver module 200 comprising a housing 220 and an acoustically transparent member 230. In one embodiment, the housing 220 may include a cap 222 that is removable or permanently attachable to the housing 220. In one embodiment, the emitter-receiver module 200 includes an interface guide 235 and/or one or more side guides 240 that can be useful in assisting the coupling of the emitter-receiver module 200 to the hand wand 100. The emitter-receiver module 200 can include a transducer 280 which can emit energy through an acoustically transparent member 230. The acoustically transparent member 230 can be a window, a filter and/or a lens. The acoustically transparent member 230 can be made of any material that is transparent to the energy that is that is emitted by the transducer 280. In one embodiment, the acoustically transparent member 230 is transparent to ultrasound energy.

Figure 6:
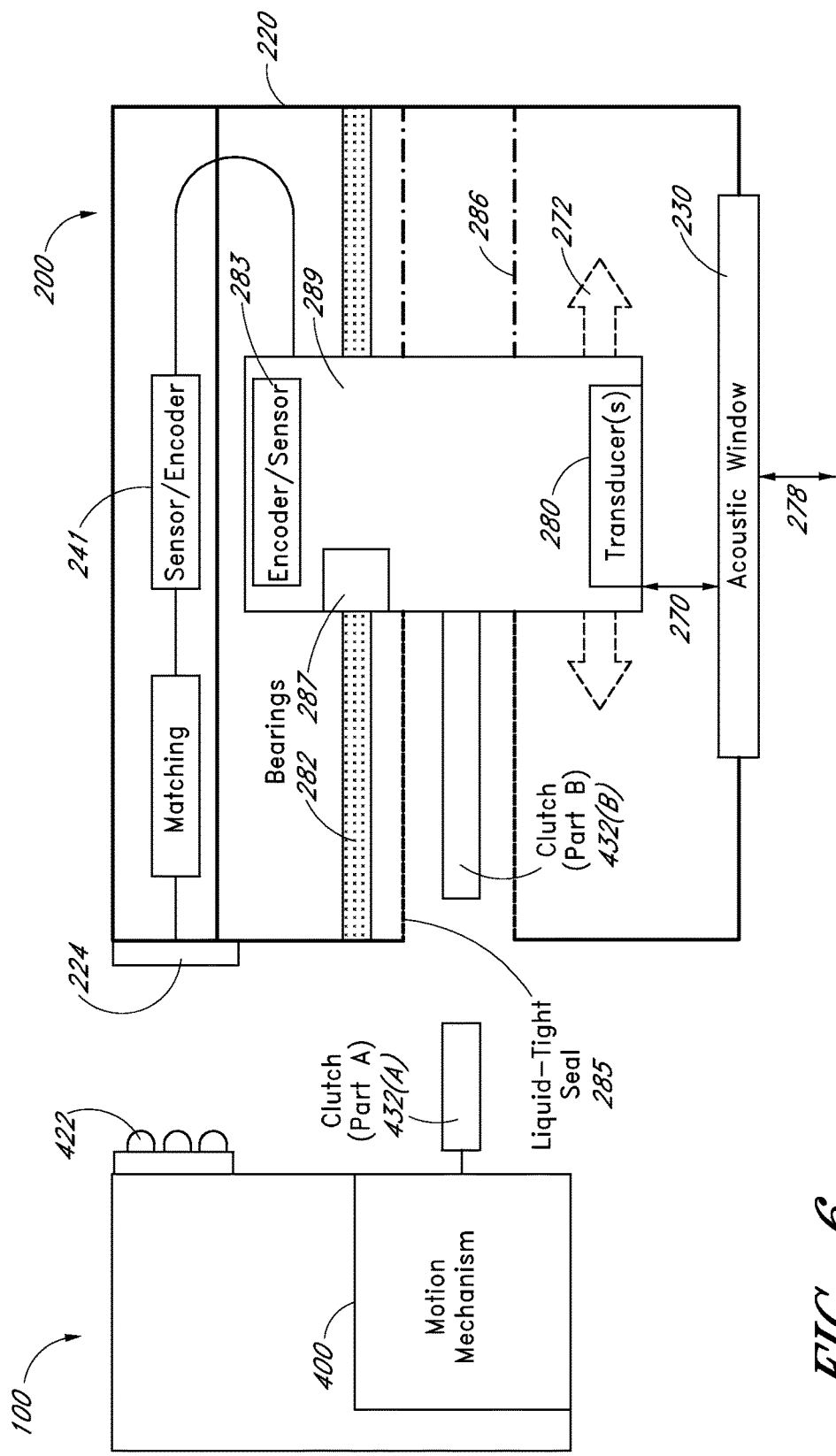
FIG. 6 is a block diagram illustrating an emitter-receiver module according to various embodiments of the present invention.

In various embodiments, the transducer 280 is in communication with the controller 300. In one embodiment, the transducer 280 is electronically coupled to the hand wand 100 and/or the controller 300. In one embodiment, the housing 220 is sealed by the cap 222 and the structure of the combination of the housing 220 and the cap 222 can hold a liquid (not shown). As illustrated in FIG. 6, an embodiment of the emitter-receiver module 200 housing 220 can have a port 275 which allows interfacing from the hand wand 100 into the transducer module 200 without affecting the integrity of the sealed structure of the housing 220 and the cap 222. Further, the cap 222 can include one or more ports. For example, a first port 292, a second port 293 and a third port 294. The ports in the cap 222 can be useful for electronically coupling the transducer 280 to the hand wand 100 and/or the controller 300. In one embodiment, at least one of the ports in the cap 222 may be used to interface a sensor 201 that may be useful in the emitter-receiver module 200. The sensor 201 can be in communication with the controller 300. More than one sensor 201 is used in some embodiments.

In various embodiments, as illustrated in the block diagram of FIG. 6, the transducer 280 is movable within the emitter-receiver module 200. The transducer 280 is held by a transducer holder 289. In one embodiment, the transducer holder 289 includes a sleeve 287 which is moved along motion constraining bearings, such as linear bearings, namely, a bar (or shaft) 282 to ensure a repeatable linear movement of the transducer 280. In one embodiment, sleeve 287 is a spline bushing which prevents rotation about a spline shaft 282, but any guide to maintain the path of motion is appropriate. In one embodiment, the transducer holder 289 is driven by a motion mechanism 400, which may be located in the hand wand 100 or in the emitter-receiver module 200. The motion mechanism 400, as is discussed below in relation to FIG. 7, includes a scotch yoke 403 with a movement member 432 and a magnetic coupling 433 on a distal end of the movement member 432. The magnet coupling 433 helps move the transducer 280. One benefit of a motion mechanism such as motion mechanism 400 is that it provides for a more efficient, accurate and precise use of an ultrasound transducer 280, for both imaging and for therapy purposes. One advantage this type of motion mechanism has over conventional fixed arrays of multiple transducers fixed in space in a housing is that the fixed arrays are a fixed distance apart. By placing transducer 280 on a linear track under controller 300 control, embodiments of the system and device provide for adaptability and flexibility in addition to the previously mentioned efficiency, accuracy and precision. Real time and near real time adjustments can be made to imaging and treatment positioning along the controlled motion by the motion mechanism 400. In addition to the ability to select nearly any resolution based on the incremental adjustments made possible by the motion mechanism 400, adjustments can be made if imaging detects abnormalities or conditions meriting a change in treatment spacing and targeting.

In one embodiment, one or more sensors 201 may be included in the emitter-receiver module 200. In one embodiment, one or more sensors 201 may be included in the emitter-receiver module 200 to ensure that a mechanical coupling between the movement member 432 and the transducer holder 289 is indeed coupled. In one embodiment, an encoder 283 may be positioned on top of the transducer holder 289 and a sensor 201 may be located in a dry portion of the emitter-receiver module 200, or vice versa (swapped). In various embodiments the sensor 201 is a magnetic sensor, such as a giant magnetoresistive effect (GMR) or Hall Effect sensor, and the encoder a magnet, collection of magnets, or multi-pole magnetic strip. The sensor may be positioned as a transducer module home position. In one embodiment, the sensor 201 is a contact pressure sensor. In one embodiment, the sensor 201 is a contact pressure sensor on a surface of the device to sense the position of the device or the transducer on the patient. In various embodiments, the sensor 201 can be used to map the position of the device or a component in the device in one, two, or threes dimensions. In one embodiment the sensor 201 is configured to sense the position, angle, tilt, orientation, placement, elevation, or other relationship between the device (or a component therein) and the patient. In one embodiment, the sensor 201 comprises an optical sensor. In one embodiment, the sensor 201 comprises a roller ball sensor. In one embodiment, the sensor 201 is configured to map a position in one, two and/or three dimensions to compute a distance between areas or lines of treatment on the skin or tissue on a patient. Motion mechanism 400 can be any motion mechanism that may be found to be useful for movement of the transducer 280. Other embodiments of motion mechanisms useful herein can include worm gears and the like. In various embodiments of the present invention, the motion mechanism is located in the emitter-receiver module 200. In various embodiments, the motion mechanism can provide for linear, rotational, multi-dimensional motion or actuation, and the motion can include any collection of points and/or orientations in space. Various embodiments for motion can be used in accordance with several embodiments, including but not limited to rectilinear, circular, elliptical, arc-like, spiral, a collection of one or more points in space, or any other 1-D, 2-D, or 3-D positional and attitudinal motional embodiments. The speed of the motion mechanism 400 may be fixed or may be adjustably controlled by a user. One embodiment, a speed of the motion mechanism 400 for an image sequence may be different than that for a treatment sequence. In one embodiment, the speed of the motion mechanism 400 is controllable by the controller 300.

Transducer 280 can have a travel distance 272 such that an emitted energy 50 is able to be emitted through the acoustically transparent member 230. In one embodiment, the travel 272 is described as end-to-end range of travel of the transducer 280. In one embodiment, the travel 272 of the transducer 280 can be between about 100 mm and about 1 mm. In one embodiment, the length of the travel 272 can be about 25 mm. In one embodiment, the length of the travel 272 can be about 15 mm. In one embodiment, the length of the travel 272 can be about 10 mm. In various embodiments the length of the travel 272 can be about between 0-25 mm, 0-15 mm, 0-10 mm.

The transducer 280 can have an offset distance 270, which is the distance between the transducer 280 and the acoustically transparent member 230. In various embodiments of the present invention, the transducer 280 can image and treat a region of interest of about 25 mm and can image a depth less than about 10 mm. In one embodiment, the emitter-receiver module 200 has an offset distance 270 for a treatment at a depth 278 of about 4.5 mm below the skin surface 501 (see FIG. 15).

In various embodiments, transducer modules 200 can be configured for different or variable ultrasonic parameters. For example, in various non-limiting embodiments, the ultrasonic parameter can relate to aspects of the transducer 280, such as geometry, size, timing, spatial configuration, frequency, variations in spatial parameters, variations in temporal parameters, coagulation formation, depth, width, absorption coefficient, refraction coefficient, tissue depths, and/or other tissue characteristics. In various embodiments, a variable ultrasonic parameter may be altered, or varied, in order to effect the formation of a lesion for the desired cosmetic approach. In various embodiments, a variable ultrasonic parameter may be altered, or varied, in order to effect the formation of a lesion for the desired clinical approach. By way of example, one variable ultrasonic parameter relates to configurations associated with tissue depth 278. In several embodiments, the transducer module 200 is configured for both ultrasonic imaging and ultrasonic treatment and is operably coupled to at least one controlling device 150, 160 and a movement mechanism 400. The transducer module 200 is configured to apply ultrasonic therapy at a first ultrasonic parameter and a second ultrasonic parameter. In various embodiments, the first and second ultrasonic parameters are selected from the group consisting of: variable depth, variable frequency, and variable geometry. For example, in one embodiment, a single transducer module 200 delivers ultrasonic therapy at two or more depths 278, 278'. In another embodiment, two or more interchangeable transducer modules 200 each provide a different depth 278 (e.g., one module treats at 3 mm depth while the other treats at a 4.5 mm depth). In yet another embodiment, a single transducer module 200 delivers ultrasonic therapy at two or more frequencies, geometries, amplitudes, velocities, wave types, and/or wavelengths. In other embodiments, two or more interchangeable transducer modules 200 each provide a different parameter value. In one embodiment, a single transducer module 200 may provide at least two different depths 278, 278' and at least two different frequencies (or other parameter). Variable parameter options are particularly advantageous in certain embodiments because they offer enhanced control of tissue treatment and optimize lesion formation, tissue coagulation, treatment volume, etc.

Figure 15:
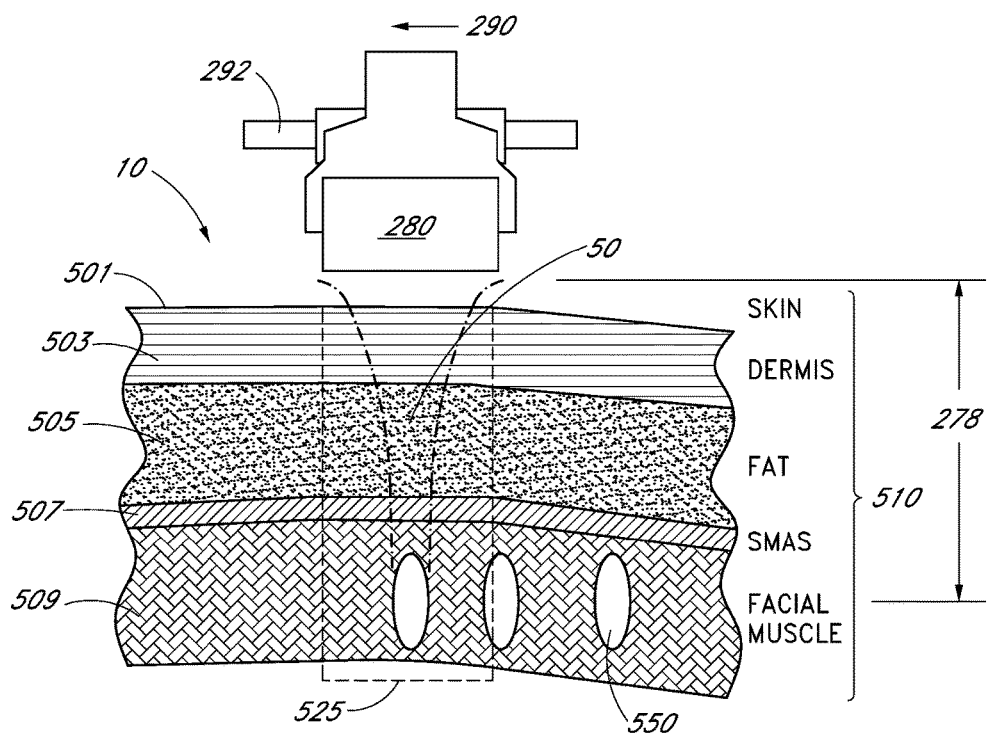
FIG. 15 is a cross-sectional illustration depicting an apparatus and a method according to one embodiment of the present invention.

FIG. 15 illustrates one embodiment of a depth 278 that corresponds to a muscle depth. In various embodiments, the depth 278 can correspond to any tissue, tissue layer, skin, dermis, fat, SMAS, muscle, or other tissue. In some embodiments, different types of tissue are treated to provide synergistic effects, thus optimizing clinical results. In another embodiment, the emitter-receiver module has an offset distance 270 for a treatment at a depth 278 of about 3.0 mm below the surface 501. In various embodiments, this offset distance may be varied such that the transducer 280 can emit energy to a desired depth 278 below a surface 501. In various embodiments, in a treatment mode, bursts of acoustic energy from the transducer 280 can create a linear sequence of individual thermal lesions 550. In one embodiment the individual thermal lesions 550 are discrete. In one embodiment the individual thermal lesions 550 are overlapping. In various embodiments, the transducer 280 can image to a depth roughly between 1 and 100 mm. In one embodiment, the transducer imaging depth can be approximately 20 mm. In one embodiment, the transducer 280 can treat to a depth of between about zero (0) to 25 mm. In one embodiment, the transducer treatment depth can be approximately 4.5 mm.

In any of the embodiments described herein, the transducer treatment depth can be approximately 0.5 mm, 1 mm, 1.5 mm, 2 mm, 3 mm, 4 mm, 4.5 mm, 5 mm, 6 mm, 10 mm 15 mm, 20 mm, 25 mm, or any other depth in the range of 0-100 mm. Varied depth treatment, including treatment of the same tissue at different depths or treatment of different tissues, can increase clinical results by providing synergistic effects.

In various embodiments of the present invention, a transducer 280 is capable of emitting ultrasound energy for imaging, diagnostics, or treating and combinations thereof. In one embodiment, the transducer 280 is configured to emit ultrasound energy at a specific depth in a region of interest to target a region of interest of a specific tissue such as a corrugator supercilii muscle as described below. In this embodiment, the transducer 280 may be capable of emitting unfocused or defocused ultrasound energy over a wide area of the region of interest 65 for treatment purposes (see FIGS. 12 and 22). In one embodiment, the emitter-receiver module 200 contains a transducer 280 that can image and treat a region of tissue up to 25 mm long and can image a depth of up to 8 millimeters. Treatment occurs along a line less than or equal to the transducer's active length, which is indicated in one embodiment by guide marks (not illustrated here) on the sides of the emitter-receiver module 200 near a acoustically transparent member 230 along the surface adjacent to the patient's skin. In one embodiment, a marked guide at the front tip of the transducer 280 represents the center of the treatment line. In one embodiment of a treatment mode, bursts of sound energy create a linear sequence of individual thermal coagulation zones. In one embodiment the individual thermal coagulation zones are discrete. In one embodiment the individual thermal coagulation zones are overlapping. A label (not illustrated here) may be applied or etched on a side or top surface of the emitter-receiver module 200 to provide the transducer 280 type, expiration date, and other information. In one embodiment, an emitter-receiver module 200 can be configured with a label for tracking the type transducer 280 used, treatment frequency and treatment depth, a unique serial number, a part number, and date of manufacture. In one embodiment, the emitter-receiver modules 200 are disposable. In one embodiment, the system tracks use of the emitter-receiver modules 200 in order to determine the remaining life of the emitter-receiver module 200 as transducer life diminishes over time and/or usage. Once a transducer 280 has diminished capacity, the emitter-receiver module 200 may work less effectively in performing its functions. In one embodiment, the emitter-receiver module 200 or controller 300 will track usage and prevent additional usage of an emitter-receiver module 200 beyond a recommended usage life in order to preserve the safety and effectiveness of the device. This safety feature can be configured based on test data.

In one embodiment, an emitter-receiver module 200 is configured with a treatment frequency of approximately 4 MHz, a treatment depth of approximately 4.5 mm and an imaging depth range of roughly 0-8 mm. In one embodiment, an emitter-receiver module 200 is configured with a treatment frequency of approximately 7 MHz, a treatment depth of approximately 3.0 mm and an imaging depth range of roughly 0-8 mm. In one embodiment, an emitter-receiver module 200 is configured with a treatment frequency of approximately 7 MHz, a treatment depth of approximately 4.5 mm and an imaging depth range of roughly 0-8 mm.

Transducer 280 may comprise one or more transducers for facilitating imaging and/or treatment. The transducer 280 may comprise a piezoelectrically active material, such as, for example, lead zirconante titanate, or other piezoelectrically active materials such as, but not limited to, a piezoelectric ceramic, crystal, plastic, and/or composite materials, as well as lithium niobate, lead titanate, barium titanate, and/or lead metaniobate, including piezoelectric, electrically conductive, and plastic film layers deposited on spherically focused backing material. In addition to, or instead of, a piezoelectrically active material, the transducer 280 may comprise any other materials configured for generating radiation and/or acoustical energy. The transducer 280 may also comprise one or more matching and/or backing layers coupled to the piezoelectrically active material. The transducer 280 may also be configured with single or multiple damping elements.

In one embodiment, the thickness of a transduction element of the transducer 280 may be configured to be uniform. That is, the transduction element may be configured to have a thickness that is generally substantially the same throughout. In another embodiment, the transduction element may also be configured with a variable thickness, and/or as a multiple damped device. For example, the transduction element of the transducer 280 may be configured to have a first thickness selected to provide a center operating frequency of a lower range, for example from about 1 MHz to about 10 MHz. The transduction element may also be configured with a second thickness selected to provide a center operating frequency of a higher range, for example from about 10 MHz to greater than 100 MHz.

In yet another embodiment, the transducer 280 is configured as a single broadband transducer excited with two or more frequencies to provide an adequate output for raising a temperature within a treatment area of the region of interest to the desired level as discussed herein. The transducer 280 may be configured as two or more individual transducers, such that each transducer 280 may comprise a transduction element. The thickness of the transduction elements may be configured to provide center-operating frequencies in a desired treatment range. For example, in one embodiment, the transducer 280 may comprise a first transducer configured with a first transduction element having a thickness corresponding to a center frequency range of about 1 MHz to about 10 MHz, and a second transducer configured with a second transduction element having a thickness corresponding to a center frequency range of about 10 MHz to greater than 100 MHz. Various other combinations and ranges of thickness for a first and/or second transduction element can be designed to focus at specific depths below a surface 501, for specific frequency ranges, and/or specific energy emissions.

The transduction elements of the transducer 280 can be configured to be concave, convex, and/or planar. In one embodiment, the transduction elements are configured to be concave in order to provide focused energy for treatment of the region of interest. Additional embodiments of transducers are disclosed in U.S. patent application Ser. No. 10/944,500, entitled "System and Method for Variable Depth Ultrasound Treatment," incorporated in its entirety herein by reference.

Moreover, the transducer 280 can be any distance from the surface 501. In that regard, it can be far away from the surface 501 disposed within a long transducer or it can be just a few millimeters from the surface 501. This distance can be determined by design using the offset distance 270 as described herein. In certain embodiments, positioning the transducer 280 closer to the surface 501 is better for emitting ultrasound at higher frequencies. Moreover, both two and three dimensional arrays of elements can be used in the present invention. Furthermore, the transducer 280 may comprise a reflective surface, tip, or area at the end of the transducer 280 that emits ultrasound energy. This reflective surface may enhance, magnify, or otherwise change ultrasound energy emitted from the CTS 20.

In various embodiments any set of one or more transducers 280 can be used for various functions, such as separate treat/image or dual-mode (both treat/image) transducers or a treat-only version. In various embodiments the imaging element(s) can be on the side (adjacent to) or at any relative position, attitude, and/or height, or even within the therapy element(s). One or more therapy depths and frequencies can be used and one or more imaging elements or one or more dual-mode elements. In various embodiments any controllable means of moving the active transduction element(s) within the emitter-receiver module 200 housing constitute viable embodiments.

In various embodiments, the emitter-receiver module 200 can also be configured in various manners and comprise a number of reusable and/or disposable components and parts in various embodiments to facilitate its operation. For example, the emitter-receiver module 200 can be configured within any type of transducer probe housing or arrangement for facilitating the coupling of the transducer 280 to a tissue interface, with such housing comprising various shapes, contours and configurations. The emitter-receiver module 200 can comprise any type of matching, such as for example, electric matching, which may be electrically switchable, multiplexer circuits and/or aperture/element selection circuits, and/or probe identification devices, to certify probe handle, electric matching, transducer usage history and calibration, such as one or more serial EEPROM (memories).

In various embodiments, the emitter-receiver module 200 may also comprise cables and connectors, motion mechanisms, motion sensors and encoders, thermal monitoring sensors, and/or user control and status related switches, and indicators such as LEDs. In one embodiment, a motion mechanism similar to the motion mechanism 400 described in the hand wand 100 may be used to drive the emitter-receiver module 200 from within the emitter-receiver module 200. In one embodiment, a hand wand 100 is electrically connectable to the emitter-receiver module 200 to drive the emitter-receiver module 200 from within itself. In various embodiments, a motion mechanism (in any of the embodiments described herein) may be used to controllably create multiple lesions, or sensing of probe motion itself may be used to controllably create multiple lesions and/or stop creation of lesions 550, as discussed herein. For example in one embodiment, for safety reasons if the emitter-receiver module 200 is suddenly jerked or is dropped, a sensor can relay this action to the controller 300 to initiate a corrective action or shut down the emitter-receiver module 200. In addition, an external motion encoder arm may be used to hold the probe during use, whereby the spatial position and attitude of the emitter-receiver module 200 is sent to the controller 300 to help controllably create lesions 550. Furthermore, other sensing functionality such as profilometers or other imaging modalities may be integrated into the emitter-receiver module 200 in accordance with various embodiments. In one embodiment, pulse-echo signals to and from the emitter/receiver module 200 are utilized for tissue parameter monitoring of the treatment region 550.

Coupling components can comprise various devices to facilitate coupling of the emitter-receiver module 200 to a region of interest. For example, coupling components can comprise cooling and acoustic coupling system configured for acoustic coupling of ultrasound energy and signals. Acoustic cooling/coupling system with possible connections such as manifolds may be utilized to couple sound into the region-of-interest, control temperature at the interface and deeper into tissue, provide liquid-filled lens focusing, and/or to remove transducer waste heat. The coupling system may facilitate such coupling through use of one or more coupling mediums, including air, gases, water, liquids, fluids, gels, solids, and/or any combination thereof, or any other medium that allows for signals to be transmitted between the transducer 280 and a region of interest. In one embodiment one or more coupling media is provided inside a transducer. In one embodiment a fluid-filled emitter-receiver module 200 contains one or more coupling media inside a housing. In one embodiment a fluid-filled emitter-receiver module 200 contains one or more coupling media inside a sealed housing, which is separable from a dry portion of an ultrasonic device.

In addition to providing a coupling function, in accordance with one embodiment, the coupling system can also be configured for providing temperature control during the treatment application. For example, the coupling system can be configured for controlled cooling of an interface surface or region between the emitter-receiver module 200 and a region of interest and beyond by suitably controlling the temperature of the coupling medium. The suitable temperature for such coupling medium can be achieved in various manners, and utilize various feedback systems, such as thermocouples, thermistors or any other device or system configured for temperature measurement of a coupling medium. Such controlled cooling can be configured to further facilitate spatial and/or thermal energy control of the emitter-receiver module 200.

Figure 7:
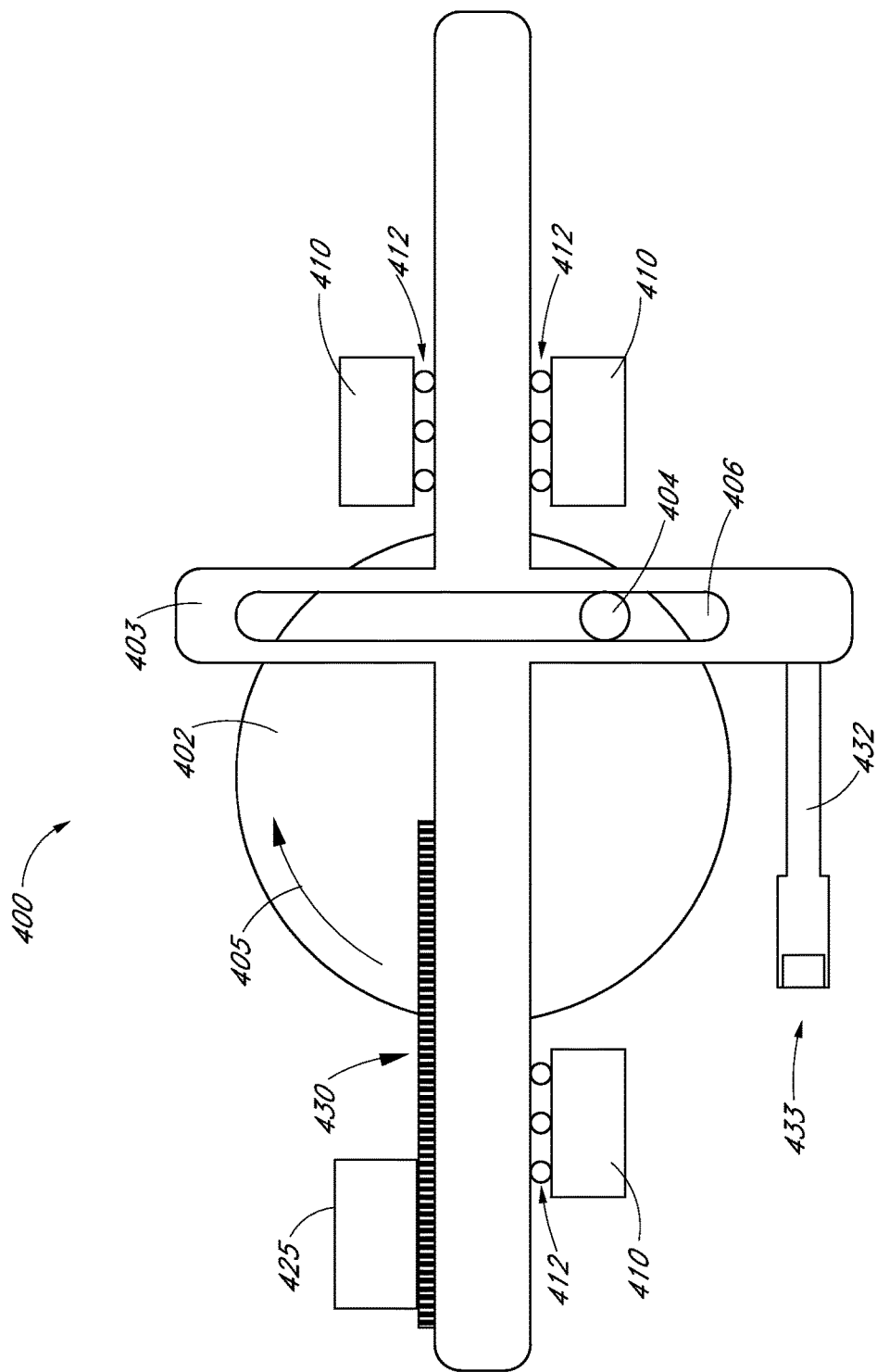
FIG. 7 is an illustration depicting a movement mechanism according to various embodiments of the present invention.

In one embodiment, the emitter-receiver module 200 is connected to a motion mechanism 400 in the hand wand 100. In one embodiment, the motion mechanism 400 may be in the emitter-receiver module 200. One embodiment of a motion mechanism 400 is illustrated in FIG. 7, which depicts a two phase stepper motor 402 and a scotch yoke 403 to produce a linear motion. The stepper motor 402 rotates as indicated by arrow 405 which moves a pin 404 in a circular path. The pin 404 slides in a slot 406 of the scotch yoke 403. This causes the scotch yoke 403 to move in a linear fashion. The scotch yoke 403 is held by guides 410 and glide members 412 may be between the scotch yoke 403 and guide 410. In one embodiment, a guide 410 is a shoulder screw. Embodiments of the glide member 412 may include any material or mechanical device that lowers a coefficient of friction between the guide 410 and the scotch yoke 403, or any linear bearings. For example, in various embodiments the glide member 412 can be at least one of an elastomeric material, a lubricant, ball bearings, a polished surface, a magnetic device, pressurized gas, or any other material or device useful for gliding.

A sensor 425 operates as one embodiment of a position sensor by reading an encoder 430 which is mounted on the scotch yoke 403. In one embodiment, the encoder strip 430 is an optical encoder which has a pitch in a range from about 1.0 mm to about 0.01 mm. In one embodiment, the pitch may be about 0.1 mm. The encoder strip 430 can include index marks at each end of its travel. The direction of travel of the encoder strip 430 can be determined by comparing phases of two separate channels in the optical sensor 425. In one embodiment, the encoder strip 430 has one, two or more home positions which may be useful in calibrating for a position and travel of the scotch yoke 403.

In one embodiment, the movement of the scotch yoke 403 is transferred through the movement mechanism 432 such that the transducer 280 moves in a linear fashion inside of the emitter-receiver module 200. In one embodiment, the scotch yoke 403 includes a movement member 432 and a magnetic coupling 433 on a distal end of the movement member 432. The movement member 432 can be sized to travel through or within a liquid-tight seal.

Figure 8:
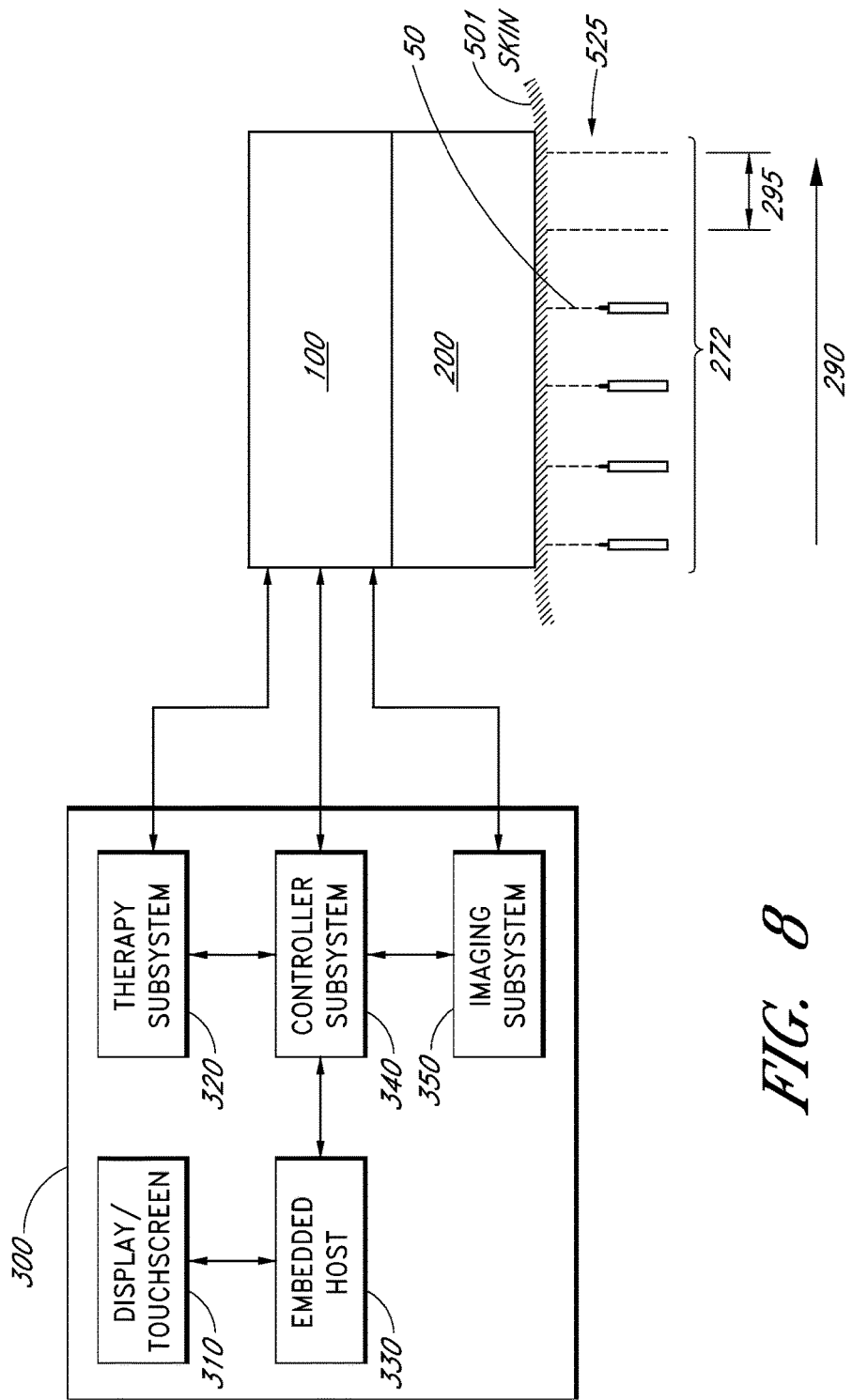
FIG. 8 is a block diagram illustrating a cosmetic treatment system according to various embodiments of the present invention.

Transducer 280 can have a travel distance 272 The coupling system may facilitate such coupling With reference to FIG. 8, a block diagram illustrates various embodiments of the CTS 20. In one embodiment, the controller 300 includes a controller subsystem 340, a therapy subsystem 320, an imaging subsystem 350, an embedded host 330 (with software) and an interactive graphical display 310. In one embodiment, the therapy subsystem 320, the controller subsystem 340, and/or the imaging subsystem 350 is interfaced with the hand wand 100 and/or the emitter-receiver module 200. In various embodiments, the CTS 20 has built into the controller 300 limits as to an amount of energy 50 that can be emitted from the emitter-receiver module 200. These limits can be determined by time of emission, frequency of the energy emitted, power of energy, a temperature, and/or combinations thereof. The temperature may be from monitoring the surface 501 and/or monitoring the emitter-receiver module 200. According to one embodiment the limits may be preset and cannot be changed by the user.

According to various embodiments, when the emitter-receiver module 200 is coupled to the surface 501, which may be a skin surface of the subject, the CTS 20 can image and/or treat a treatment area 272. In some aspects of these embodiments, the imaging by the CTS 20 can be over essentially the entire treatment area 272 at specified depths 278 below the surface 501. In some aspects of these embodiments, the treatment can include discrete energy emissions 50 to create lesion 550 at intervals along the treatment area 272 and at specified depths 278. In one embodiment the intervals are discrete. In one embodiment the intervals are overlapping.

In various embodiments the imaging subsystem 350 may be operated in a B-mode. The imaging subsystem 350 can provide support to the emitter-receiver module 200 such that the emitter-receiver module 200 can have emission energy 50 from a frequency of about 10 MHz to greater than 100 MHz. In one embodiment, the frequency is about 18 MHz. In one embodiment, the frequency is about 25 MHz. The imaging subsystem 350 can support any frame rate that may be useful for the applications. In some embodiments, the frame rate may be in a range from about 1 frames per second (hereinafter "FPS") to about 100 FPS, or from about 5 FPS to about 50 FPS or from about 5 FPS to about 20 FPS nominal. An image field of view may be controlled by the image area of the transducer 280 in a focus of the transducer 280 at a specific depth 278 below the surface 501 as discussed herein. In various embodiments, the field of view can be less than 20 mm in depth and 100 mm in width or less than 10 mm in depth and less than 50 mm in width. In one embodiment, a particularly useful image field of view is about 8 mm in depth by about 25 mm in width.

A resolution of the field of view can be controlled by the graduation of the movement mechanism 400. As such, any pitch may be useful based on the graduation of the motion mechanism 400. In one embodiment, the resolution of the field of view may be controlled by the resolution of an encoder 430 and sensor 425. In one embodiment the image field of view can have a pitch in the range of 0.01 mm to 0.5 mm or from about 0.05 mm to about 0.2 mm. In one embodiment, a particularly useful line pitch for the image field of view is about 0.1 mm.

According to various embodiments, the imaging subsystem 350 can include one or more functions. In one embodiment, the one or more functions can include any of the following B-mode, scan image, freeze image, image brightness, distance calipers, text annotation for image, save image, print image, and/or combinations thereof. In various embodiments of the present invention, the imaging subsystem 350 contains pulse echo imaging electronics.

Various embodiments of the therapy subsystem 320 comprise a radio frequency (hereinafter "RF") driver circuit which can deliver and/or monitor power going to the transducer 280. In one embodiment, the therapy subsystem 320 can control an acoustic power of the transducer 280. In one embodiment, the acoustic power can be from a range of 1 watt (hereinafter "W") to about 100 W in a frequency range from about 1 MHz to about 10 MHz, or from about 10 W to about 50 W at a frequency range from about 3 MHz to about 8 MHz. In one embodiment, the acoustic power and frequencies are about 40 W at about 4.3 MHz and about 30 W at about 7.5 MHz. An acoustic energy produced by this acoustic power can be between about 0.01 joule (hereinafter "J") to about 10 J or about 2 J to about 5 J. In one embodiment, the acoustic energy is in a range less than about 3 J.

In various embodiments the therapy subsystem 320 can control a time on for the transducer 280. In one embodiment, the time on can be from about 1 millisecond (hereinafter "ms") to about 100 ms or about 10 ms to about 50 ms. In one embodiment, time on periods can be about 30 ms for a 4.3 MHz emission and about 30 ms for a 7.5 MHz emission.

In various embodiments, the therapy subsystem 320 can control the drive frequency of the transducer 280 moving across the travel 272. In various embodiments, the frequency of the transducer 280 is based on the emitter/receiver 200 connected to the hand wand 100. According to some embodiments, the frequency of this movement may be in a range from about 1 MHz to about 10 MHz, or about 4 MHz to about 8 MHz. In one embodiment, the frequencies of this movement are about 4.3 MHz or about 7.5 MHz. As discussed herein, the length of the travel 272 can be varied, and in one embodiment, the travel 272 has a length of about 25 mm.

According to various embodiments, the therapy subsystem 320 can control the line scan along the travel 272 and this line scan can range from 0 to the length of the distal of the travel 272. In one embodiment, the line scan can be in a range from about 0 to about 25 mm. According to one embodiment, the line scan can have incremental energy emissions 50 having a treatment spacing 295 and this treatment spacing can range from about 0.01 mm to about 25 mm or from 0.2 mm to about 2.0 mm. In one embodiment, treatment spacing 295 is about 1.5 mm. In various embodiments, the treatment spacing 295 can be predetermined, constant, variable, programmable, and/or changed at any point before, during or after a treatment line. The resolution of the line scan is proportional to the resolution of the motion mechanism 400. In various embodiments, the resolution that is controllable by the therapy subsystem 320 is equivalent to the resolution controllable by the imaging subsystem 350 and, as such, can be in the same range as discussed for the imaging subsystem 350.

In various embodiments, the therapy subsystem 320 can have one or more functions. In one embodiment, the one or more functions can include any of the following: emission energy control, treatment spacing, travel length, treatment ready, treatment, treatment stop, save record, print record, display treatment, and/or combinations thereof.

In various embodiments, the control subsystem 340 includes electronic hardware which mechanically scans the transducer 280 for one or more functions. In one embodiment, one or more functions that can be scanned by the controller subsystem 340 can include scanning the transducer 280 for imaging, a position of the transducer 280 for imaging, scan slip positions of the transducer 280 at locations for therapy, controls therapy hardware settings, provides other control functions, interfacing with the embedded host 330, and/or combinations thereof. In one embodiment the locations are discrete. In one embodiment the locations are overlapping.

In various embodiments, an embedded host 330 is in two-way communication with the controller 340 and the graphical interface 310. In one embodiment, data from the controller 340 can be converted to a graphical format by the embedded host 330 and then transferred to the graphical interface 310 for displaying imaging and/or treatment data.

In one embodiment, commands can be entered by a user employing the graphical interface 310. The commands entered by use of the graphical interface 310 can be communicated to embedded host 330 and then communicated to controller 340 for control and operation of the therapy subsystem 320, the imaging subsystem 350, the hand wand 100, and/or the emitter-receiver module 200. In various embodiments, the embedded host 330 can include a processing unit, memory, and/or software.

In various embodiments, when the imaging button 150 is pressed the CTS 20 enters an imaging sequence in which the imaging subsystem 350 acquires scan lines which are transferred to the embedded host 330 for data conversion and/or graphical conversion which is then communicated to the graphical interface 310. While the system is operating in the imaging sequence, the imaging button 150 may be pressed again which puts the CTS 20 into a ready state. In an aspect of this embodiment, an audio warning or visual display such as the indicator 155 may be initiated to alert the user that the CTS 20 is in the ready state. In the ready state, the controller subsystem 340 communicates with the embedded host 330 to acquire users entered treatment settings. These treatment settings can be checked and can be verified and converted to hardware parameter in the controller subsystem 340. In one embodiment, such set hardware parameters can include treatment timing, cadence, time on, time off, RF driver power, voltage levels, acoustic power output, oscillator frequency, therapy transducer frequency, treatment spacing, travel, motion mechanism speed, and/or combinations thereof. The CTS 20 may remain in the ready state indefinitely or may be timed out after a set time period.

In various embodiments of the present invention, when the CTS 20 is in the ready state, the treatment button 160 may be activated. This activation of the treatment button 160 commences a treatment sequence. The treatment sequence is controllable by the therapy subsystem 320 which executes the treatment sequence along with the controller subsystem 340 and independently of the embedded host 330. The treatment sequence is delivered in real time and last one of the length of the activating of the treatment button 160 or a programmed time downloaded from the embedded host 330 into the controller subsystem 340 and/or the therapy subsystem 320.

In various embodiments, safety features can be designed in the CTS 20 to ensure safe use, imaging, and treatment. In various embodiments, the embedded host 330 is in communication with data port 390 which can comprise either one-way or two-way communication between the data port 390 and the embedded host 330. The data port 390 can interface any electronic storage device, for example, the data port 390 can be interfaced for one or more of a USB drive, a compact flash drive, a secured digital card, a compact disc, and the like. In one embodiment, a storage device through data port 390 to the embedded host 330 can download treatment records or software updates. In another aspect of these embodiments, the storage device can be a two-way communication through data port 390 to the embedded host 330 such that a treatment protocol can be downloaded to the embedded host 330 and CTS 20. A treatment protocol can include parameters, imaging data, treatment data, date/time, treatment duration, subject information, treatment location, and combinations thereof, and the like which can be uploaded by and/or downloaded from the embedded host 330 to the storage device via the data port 390. In one embodiment, a second data port (not shown) may be located on the back of the controller. The second data port may provide power and/or data to a printer.

In various embodiments, the CTS 20 includes a lock 395. In one embodiment, in order to operate CTS 20, lock 395 must be unlocked so that power switch 393 may be activated. In one embodiment, the power may remain on as the lock 395 is unlocked and locked successively and different parameters are entered. A key 396 (not illustrated) may be needed to unlock the lock 395. Examples of keys 396 useful herein include a standard metal tooth and groove key, or an electronic key. In some embodiments, an electronic key 396 may be digitally encoded to include user information and collect data and/or time usage of CTS 20. In one embodiment, an electronic key is particularly useful with CTS 20 may be a USB drive with encryption such that inserting the USB drive key into lock 395 the CTS 20 may be activated. In various embodiments, a software key can be configured to indicate a condition or status to the user, lock the system, interrupt the system, or other feature.

Figure 9:
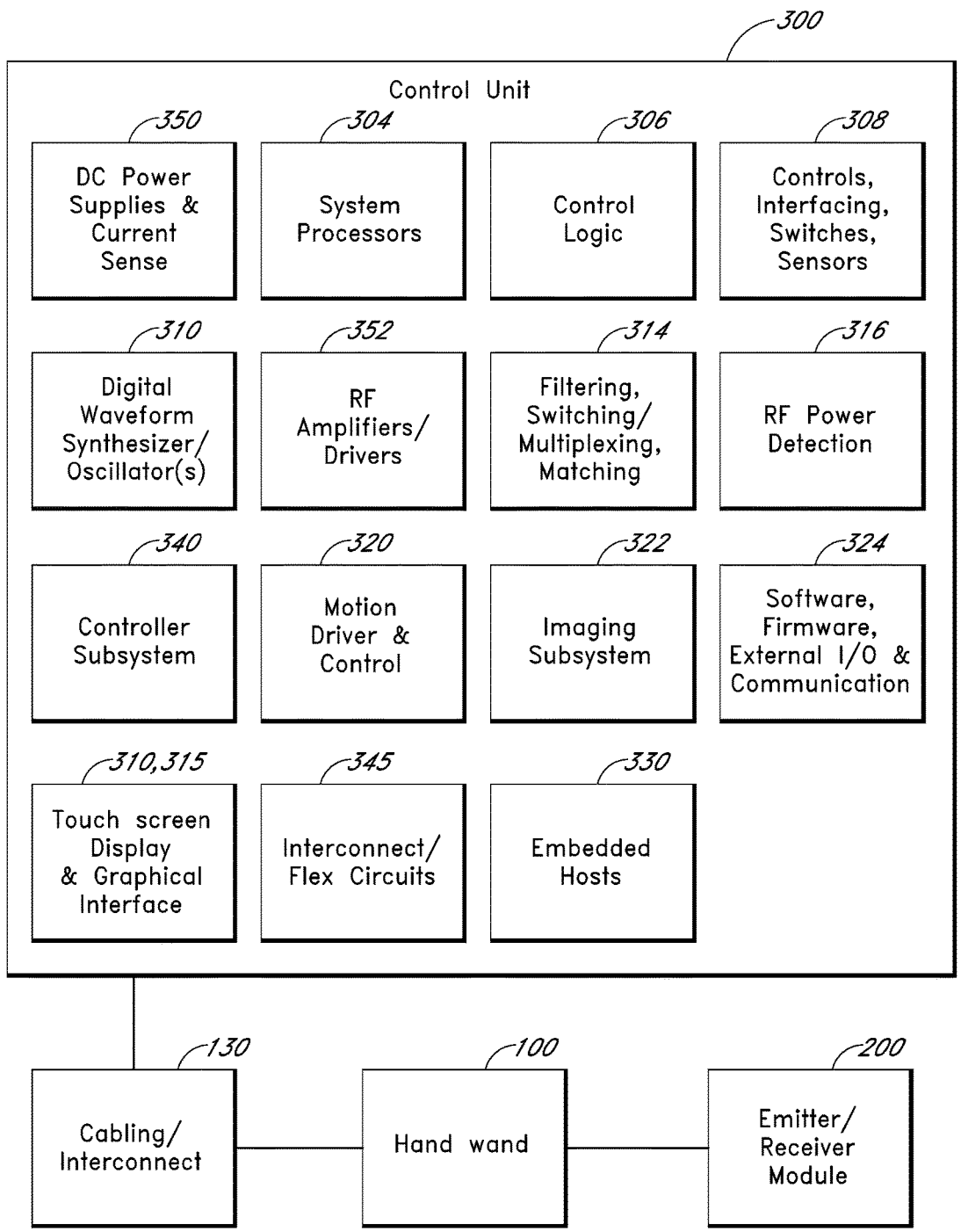
FIG. 9 is an electronic block diagram illustrating a cosmetic treatment system according to various embodiments of the present invention.

With reference to FIG. 9, a CTS 20 layout block diagram is illustrated according to various embodiments of the present invention. In accordance with the aspects of these embodiments, the controller 300 can include several electronic sections. Included in these electronic sections can be a power supply 350 which provides power to CTS 20 including the controller 300, the hand wand 100, and/or the emitter-receiver module 200. In one embodiment, the power supply 350 can supply power to a printer or other data output device. The controller 300 can include the controller subsystem 340 as described herein, the host 330, a graphical interface 310, an RF driver 352 and a front panel flex circuit 345. The RF driver 352 can provide power to the transducer 280. The embedded host 330 can be a host computer which may be used collecting user input, transferring it to the controller subsystem 340 and for displaying images and system statuses on the graphical interface 310. The power supply 350 can be convertible for use internationally based on different voltage inputs and typically is a medical grade power supply. The power supply may be plugged into a standard wall socket to draw power or may draw power from a battery or any other alternative source that may be available.

The graphical interface 310 displays images and systems status as well as facilitates the user interface for entering commands to control the CTS 20. The controller subsystem 340 can control the imaging subsystem 350, the therapy subsystem 320, as well as interfacing and communicating treatment protocol to the hand wand 100 and the emitter-receiver module 200, as described herein. In one embodiment, the controller subsystem 340 not only sets treatment parameters but also monitors the status of such treatment and transfers such status to the host 330 for display on display/touch screen 310. The front panel flex circuit 345 can be a printed circuit cable that connects the controller 300 to the interface cable 130. In one embodiment, the cable 130 can include a quick connect or release, multi-pin connector plug which interfaces to the front panel flex circuit 345 as described herein. The cable 130 allows for interfacing of the controller 300 with the hand wand 100 and the emitter-receiver module 200 as described herein.

Figure 10:
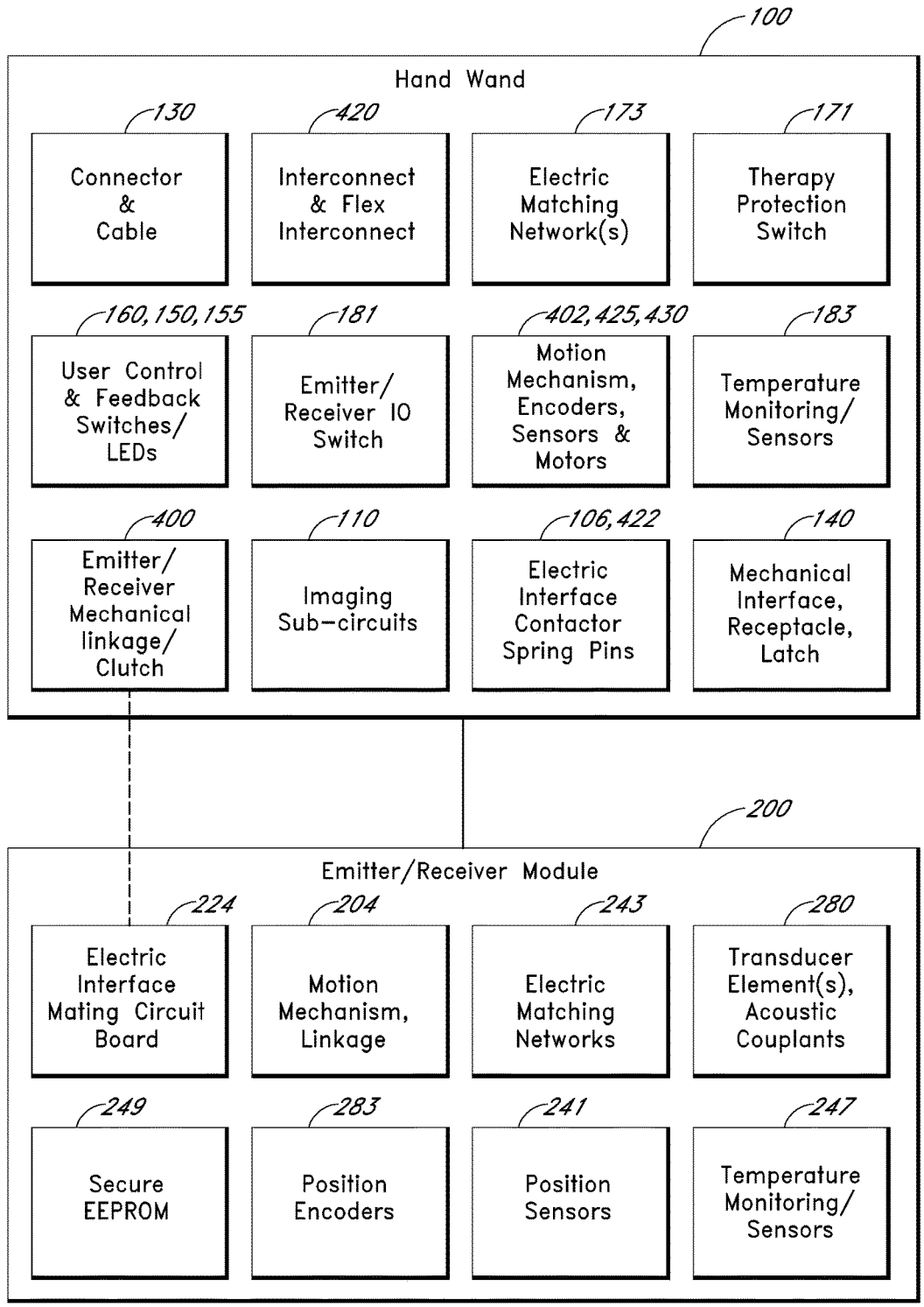
FIG. 10 is a schematic illustration of a hand wand and an emitter-receiver module according to various embodiments of the present invention.

Now with reference to FIG. 10, the hand wand 100 includes the hand piece imaging sub-circuits 110, encoder 420, sensor 425, image 150 and treat 160 switches, motor 402, status light 155, and interconnect and flex interconnect 420. The hand wand 100 interfaces with spring pin flex 106 and spring pin connector 422 which can be used for hardware, software and/or power interface from the hand wand 100 to the emitter-receiver module 200.

In various embodiments of the present invention, the emitter-receiver module 200 can include a probe ID and connector PCB 224. The probe ID and connector PCB can include a secure EEPROM. The probe ID and connector PCB 224 can be interfaced with a PCB located in a dry portion of the emitter-receiver module 200 and interfaced with the transducer 280 The transducer 280 is typically located in the liquid portion of the emitter-receiver module 200. In one embodiment, the emitter-receiver module 200 can be connected to the hand wand 100 via the spring pin flex 106 and spring pin connector 422 which can be a twelve contact spring pin connector that is recessed in the hand wand 100. The spring pin flex 106 with its twelve contact spring pin connector can be connected to the probe ID and connector PCB 224 which can include gold plated contacts. In one embodiment, the probe ID and connector PCB 224 can include a usage counter that disables the emitter-receiver module 200 after a pre-set usage. In various embodiments, the pre-set usage can range from a single treatment sequence to multiple treatment sequences. In one embodiment, the pre-set usage is determined by a pre-set time on of the transducer 280. In one embodiment, the pre-set usage is a single cycle of treatment sequences. In this aspect, essentially the emitter-receiver module 200 is disposable after each use. In one embodiment, the system automatically shuts off or otherwise indicates to a user that the emitter-receiver module 200 should be replaced. The system may be programmed to shut off or otherwise indicate replacement based on at least one of usage time, energy delivered, shelf time, or a combination thereof.

With further reference to FIG. 10, a block diagram illustrates an interconnection of the hand wand 100 and the emitter-receiver module 200. The hand wand 100 can include a therapy protection switch which can provide a electric isolation between treat and image functions. A transducer pulse generated by the controller subsystem 340 can be received by matching network 173. In one embodiment, a single transducer 280 can be used for therapy without imaging. In another embodiment one dual-mode transducer can be used for therapy and imaging. In another embodiment, two transducers 280 can be used for therapy and imaging. In yet another embodiment, therapy is done at relatively low frequencies (such as, in one embodiment, nominally 4 and 7 MHz) with a first transducer 280, and a second higher frequency transducer for imaging (such as, in one embodiment, 18-40 MHz or more).

The imaging sub-circuits 110 can include a time gain control amplifier and tunable bypass filter which can receive echoes produced by the imaging portion of the transducer 280. The imaging can be controlled by imaging switch 150. Power can be transferred from the controller 300 via cable 130. Such power can be directed to the imaging sub-circuits 110, the image switch 150 and the treatment switch 160. Such power can also be provided to the stepper motor 402, the encoder 425, the probe IO switch 181, the hand wand temperature sensor 183, and a hand wand ID EEPROM 169. All of the electronics described in FIG. 10 for the hand wand 100 can be mounted on the circuit board with an interface to cable 130 and/or an interface to the emitter-receiver module 200.

The emitter-receiver module 200 includes an interface connectable to the hand wand 100 as described in FIG. 9. The emitter-receiver module 200 can include any type of storage device 249. In one embodiment, the storage device 249 is part of the electric interface mating circuit board 224 and electric matching 243 circuit board. In one embodiment, the storage device 249 is a permanent storage device. In one embodiment, the storage device 249 is a non-volatile member. In one embodiment, the storage device 249 is an EEPROM. In one embodiment, the storage device 249 is a secure EEPROM. In one embodiment, a transducer PCB can contain calibration data and information storage in the secure EEPROM. Further in this aspect, the emitter-receiver module 200 includes a sensor which measures a fluid temperature of the fluid portion of the emitter-receiver module 200, a matching network 243 interfaced to the treatment portion of the transducer 280. In various embodiments, the storage device 249 can contain digital security information, build date, transducer focus depth, transducer power requirements, and the like. In one embodiment, the storage device 249 can include a timer which inactivates the emitter-receiver module 200 for use with CTS 20 after a predetermined shelf life has expired. The emitter-receiver module 200 can include a position encoder 283, such as a magnet, connected to the transducer 280 and a sensor 241, such as a Hall sensor, connected to the stationary emitter/receiver housing 220 via circuit board. The position encoder 283 and the position sensor 241 can act as a sensor for determining a transducer 280 home position and/or movement as described herein. The imaging portion of the transducer 280 can receive a transducer RF signal from the controller 300.

Since it is possible for a user to potentially touch the spring pin flex contacts 422 when an emitter-receiver module 200 is not attached, the current must be able to be turned off in this situation to provide safety to the user. To provide such safety, contact pins 422 on opposite ends of the spring pin flex 106 can be used to detect an attachment of the emitter-receiver module 200 to the hand wand 100. As discussed above, motion mechanism 400 can be connected to the transducer 280 to provide linear movement of the transducer along the travel 272.

In various embodiments, the CTS 20 can include various safety features to provide a safe environment for the user and/or the subject that receives treatment. One embodiment, the CTS 20 can include at least one of calibration data, safe operating area, high mismatch detect, high current detect, RF driver supply voltage monitoring, forward and reverse electric power monitoring, acoustic coupling detection, acoustic coupling complete, treatment position sensing, and combinations thereof.

For example, calibration data can include certain characteristics for a given emitter-receiver module 200 that reside on the storage device 249. Such characteristics can include but are not limited to unique and traceable serial numbers, probe identification, frequency setting, acoustic power versus voltage lookup table, electric power versus voltage lookup table, maximum power levels, date codes, usage, other information, and/or combinations thereof. For example, a safe operating area safety feature limits energy output for a given emitter-receiver module 200 is limited to a safe operating area. Such a limitation may include for a given emitter-receiver module 200, the acoustic power level supplied by the power supply voltage and the time On may be limited in the hardware and/or software of the controller 300 and/or the emitter-receiver module 200.

An example of a high mismatch detect safety feature can include if a fault occurs in reflective power from the load of the emitter-receiver module 200 is large as compared a forward power such as the emitter-receiver module 200 failure, open circuit, or high reflective energy, then a system Stop state would automatically and indefinitely be invoked by comparator circuit latched in the hardware of the controller 300 and a notification of such fault would appear on the display/touch screen 310 to alert the user. An example of a high current detect safety feature can include if a driver fault or load fault occurs such that a large current draw is detected such as for example a short circuit or electrical component failure, then a Stop state would be automatically and immediately invoked as located in the hardware of the controller 300 and a notice would be displayed on the display/touch screen 310 to alert the user.

An example of RF driver supply voltage monitoring safety feature can include the CTS 20 measuring the RF driver power supply voltage setting before, during and after treatment to assure that the voltage is at the correct level. If it is determined that the voltage is outside the correct level, then a Stop state would be automatically and immediately invoked and a notice would be displayed on the display/touch screen 310 to alert the user. An example of a safety feature includes monitoring the stepper motor 402 during treatment and determining if it is in an acceptable range such that the transducer 280 is properly moving along the travel 272 at a predetermined rate or frequency. If it is determined that the stepper motor 402 is not at an expected position, a notification is issued to alert the user.

An example of an acoustic coupling safety feature includes an imaging sequence that indicates to the user that the emitter-receiver module 200 is acoustically coupled to the surface 501 before and after treatment. An image sequence confirms that the transducer 280 is scanning a treatment area.

Still further, other safety features may be included such as thermal monitoring, use of a stop switch, a probe sensor, or a combination thereof. An example of thermal monitoring can include monitoring the temperature of the liquid portion of the emitter-receiver module 200, monitoring the temperature of the hand wand 100, monitoring the temperature of the controller 300, monitoring the temperature of the controller subsystem 340 and/or monitoring the temperature of the RF driver 352. Such temperature monitoring assures that the devices described operate within temperatures that are acceptable and will provide notification if a temperature is outside an acceptable range thus alerting the user.

A stop switch can be included in CTS 20 such that when a user hits the stop switch the system moves to a safe and inactive state upon activation of the stop switch. An example of a probe sense fail safe can include immediately stopping imaging and/or treatment if the emitter-receiver module 200 is disconnected from the hand wand 100 while in use. In one embodiment, the CTS 20 can include a system diagnostic which can include software checks for errors, unexpected events and usage. The system diagnostics may also include maintenance indicator that tracks the usage of the CTS 20 and notifies the user that maintenance is needed for the system. Other safety features may be included in the CTS 20 that are well known in the art such as fuses, system power supply over voltage and over current limiting, as well as standardized protections such as fire safety ratings, electrical safety ratings, ISO\EN 60601 compliance and the like.

In various embodiments, the CTS 20 includes a removable transducer module 200 interfaced to a hand enclosure 100 having at least one controller button (150 and/or 160) such that the transducer module 200 and the controller button (150 and/or 160) is operable using only one hand. In an aspect of the embodiments, the transducer module 200 provides ultrasound energy for an imaging function and/or a treatment function. In another aspect of the embodiments, the device includes a controller 300 coupled to the hand-held enclosure 100 and interfaced to the transducer module 200. In a further aspect of these embodiments, the controller 300 controls the ultrasound energy of and receives a signal from the transducer module 200. The controller 300 can have a power supply providing power for the ultrasound energy. In still another aspect of the embodiments, the device is used in aesthetic imaging and treatment on a brow of a patient.

Figure 11:
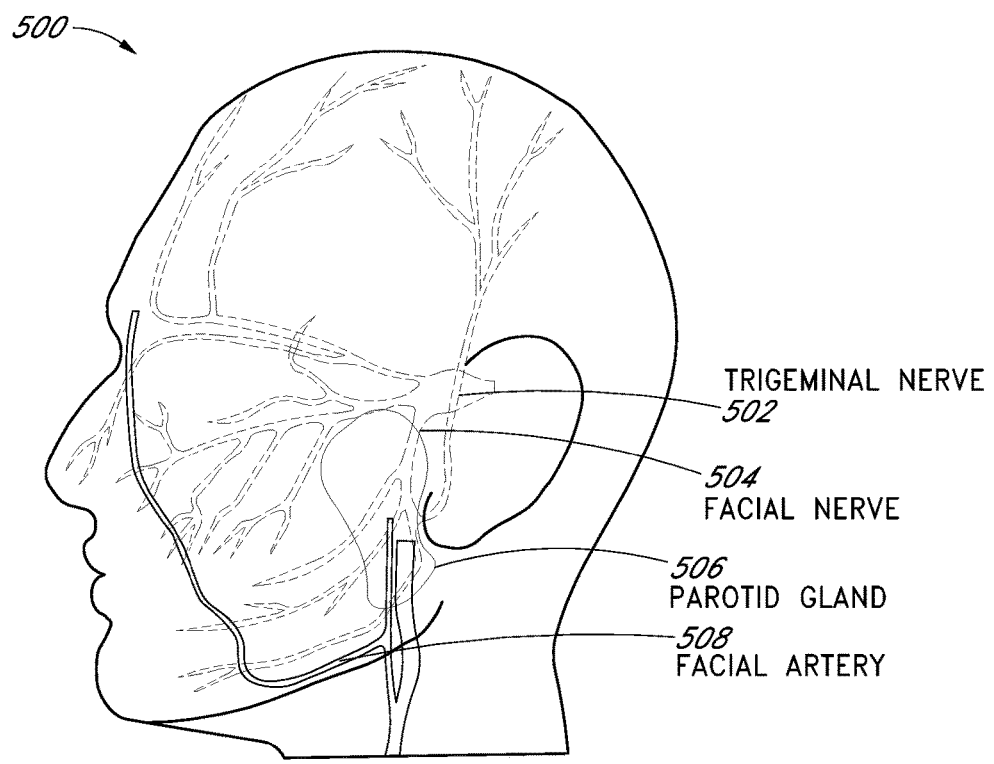
FIG. 11 is an illustration depicting one possible area of interest of a subject according to various embodiments of the present invention.
Figure 12:
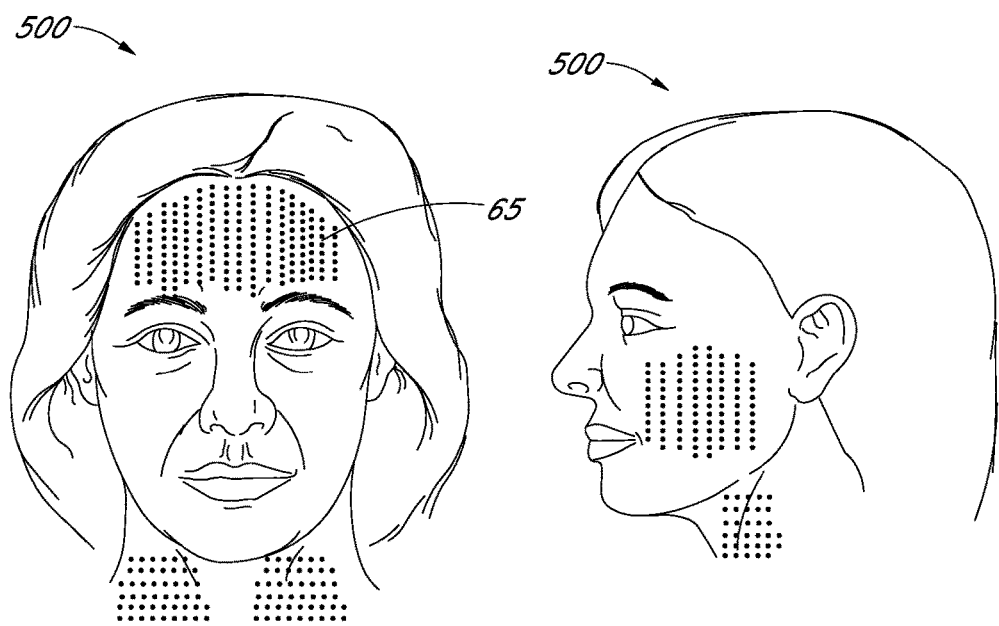
FIG. 12 is an illustration depicting one possible area of interest of a subject according to various embodiments of the present invention.
Figure 13:
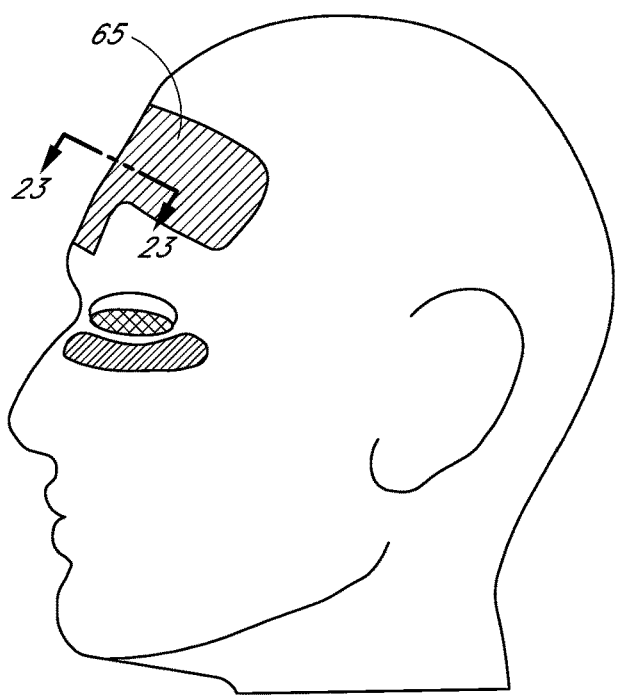
FIG. 13 is an illustration depicting an area of interest of a subject according to various embodiments of the present invention.
Figure 14:
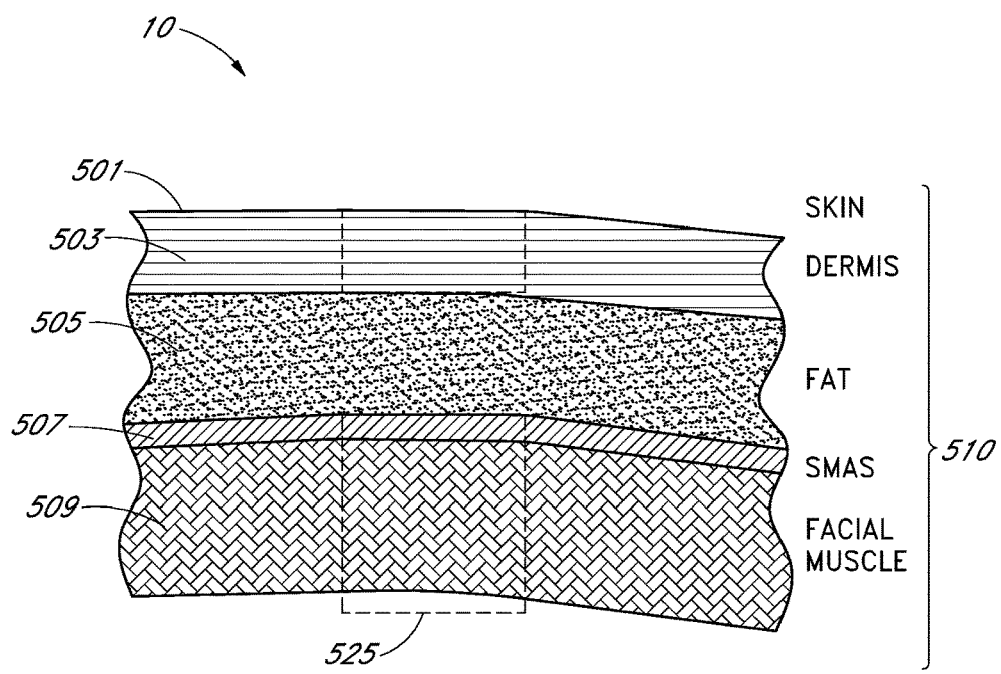
FIG. 14 is a cross-sectional illustration of a portion of an area of interest according to various embodiments of the present invention.

FIG. 11 illustrates a schematic drawing of anatomical features of interest in the head and face region of a patient 500, including a trigeminal nerve 502, a facial nerve 504, a parotid gland 506 and a facial artery 508. In one embodiment, the anatomical features of interest are areas to be treated with care or to be noted, treated with care, or even avoided during treatment. FIGS. 12-14 illustrate one region of interest 65 (hereinafter "ROI 65") and a cross-sectional tissue portion 10 along the line 23-23 of the ROI 65 on a subject 500, such as may be used for example when performing a brow lift. This cross-sectional tissue portion 10 can be located anywhere in the ROI 65 and can in any direction or of any length with in the ROT 65. Of course, the subject 500 can be a patient that may be treated with a brow lift. The cross-sectional portion tissue 10 includes a surface 501 in a dermal layer 503, a fat layer 505, a superficial muscular aponeurotic system 507 (hereinafter "SMAS 507"), and a facial muscle layer 509. The combination of these layers in total may be known as subcutaneous tissue 510. Also illustrated in FIG. 14 is a treatment zone 525 which is below the surface 501. In one embodiment, the surface 501 can be a surface of the skin of a subject 500. Although the term facial muscle may be used herein as an example, the inventors have contemplated application of the device to any tissue in the body. In various embodiments, the device and/or methods may be used on muscles (or other tissue) of the face, neck, head, arms, legs, or any other location in the body.

Facial muscle tissue is capable of contraction and expansion. Skeletal muscle is a fibrous tissue used to generate stress and strain. For example, skeletal muscles in the forehead region can produce frowning and wrinkles. There are several facial muscles within the brow or forehead including the epicranius muscle, the corrugator supercilii muscle, and the procerus muscle. These facial muscles are responsible for movement of the forehead and various facial expressions. Besides facial muscles, other tissues exist in the brow region that also can lead to wrinkles on the brow.

In accordance with one embodiment of the present invention, methods for ultrasound cosmetic treatment of tissue using one cosmetic treatment system are provided. The ultrasound energy can be focused, unfocused or defocused and is applied to a ROI 65 containing one of facial muscle tissue or dermal layers or fascia to achieve a therapeutic effect, such as a tighten of a brow of a subject 500.

In various embodiments, certain cosmetic procedures that are traditionally performed through invasive techniques are accomplished by targeting energy such as ultrasound energy at specific subcutaneous tissues 510. In one embodiment, methods for non-invasively treating subcutaneous tissues 510 to perform a brow life are provided. In one embodiment, a non-invasive brow lift is performed by applying ultrasound energy at specific depths 278 along the brow to ablatively cut, cause tissue to be reabsorbed into the body, coagulate, remove, manipulate, or paralyze subcutaneous tissue 510 such as the facial muscle 509, for example, the corrugator supercilii muscle, the epicranius muscle, and the procerus muscle within the brow to reduce wrinkles.

In some embodiments, ultrasound energy is applied at a ROI 65 along a patient's forehead. The ultrasound energy can be applied at specific depths and is capable of targeting certain subcutaneous tissues within the brow such as with reference to FIGS. 12-14, SMAS 507 and/or facial muscle 509. The ultrasound energy targets these tissues and cuts, ablates, coagulates, micro-ablates, manipulates and/or causes the subcutaneous tissue 510 to be reabsorbed into the subject's body which effectuates a brow lift non-invasively.

For example, the corrugator supercilii muscle in a target zone 525, can be targeted and treated by the application of ultrasound energy at specific depths 278. This facial muscle 509 or other subcutaneous facial muscles can be ablated, coagulated, micro-ablated, shaped or otherwise manipulated by the application of ultrasound energy in a non-invasive manner. Specifically, instead of cutting a corrugator supercilii muscle during a classic or endoscopic brow lift, the targeted muscle 509 such as the corrugator supercilii can be ablated, micro-ablated, or coagulated by applying ultrasound energy at the forehead without the need for traditional invasive techniques.

One method is configured for targeted treatment of subcutaneous tissue 510 in the forehead region 65 in various manners such as through the use of therapy only, therapy and monitoring, imaging and therapy, or therapy, imaging and monitoring. Targeted therapy of tissue can be provided through ultrasound energy delivered at desired depths 278 and locations via various spatial and temporal energy settings. In one embodiment, the tissues of interest are viewed in motion in real time by utilizing ultrasound imaging to clearly view the moving tissue to aid in targeting and treatment of a ROI 65 on the patient's forehead. Therefore, the practitioner or user performing the non-invasive brow lift can visually observe the movement and changes occurring to the subcutaneous tissue 510 during treatment.

Figure 16:
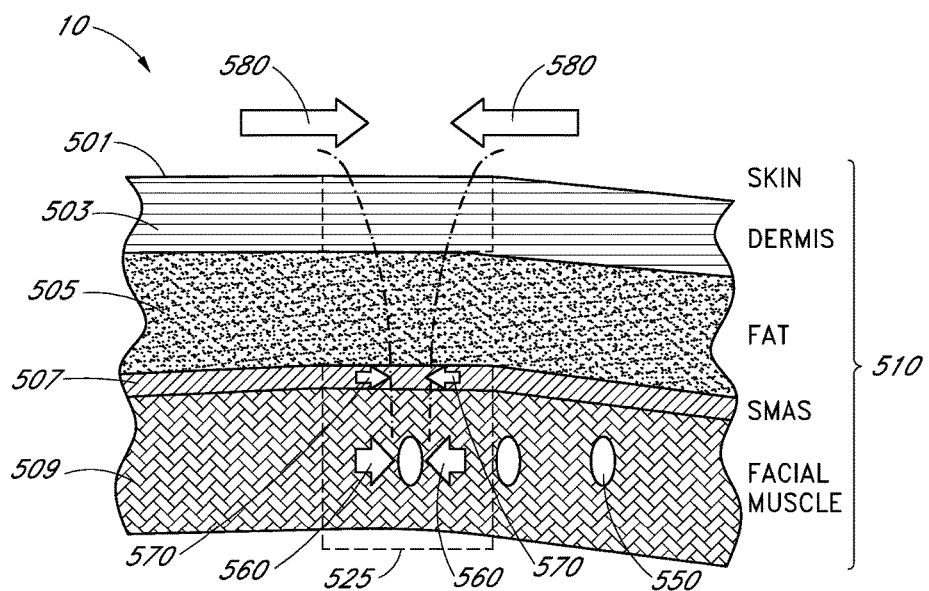
FIG. 16 is a cross-sectional illustration depicting a treatment region according to various embodiments of the present invention.
Figure 17:
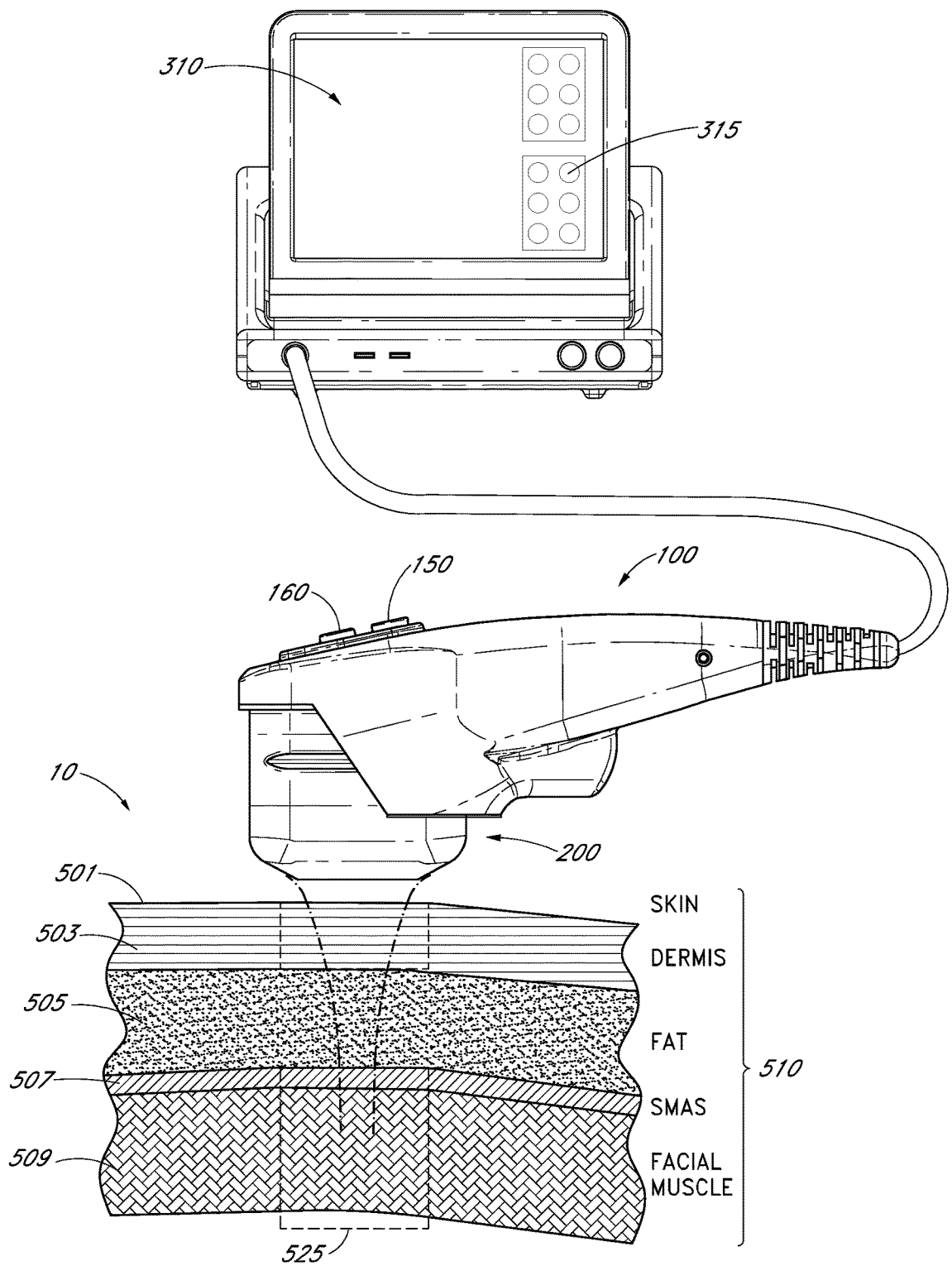
FIG. 17 is an illustration depicting the cosmetic treatment system coupled to the region of interest according to various embodiments of the present invention.

FIGS. 15-17 illustrate an embodiment of a method of administering a brow lift. Other embodiments include multiple treatment depths, three dimensional (3-D) treatment, and use of multiple treatment sessions over time. The CTS 20 can be coupled to a tissue portion 10 of the ROI 65 that is to be treated. In one embodiment, a treatment zone 525 is first imaged and then treated. In one embodiment, a user activates the imaging button 150 to initiate the imaging sequence. Imaging can be displayed on the graphical interface 310. In one embodiment, the imaging sequence can be controlled on a touchscreen 315 that is part of the graphical interface 310. After the imaging sequence is started, the treatment sequence can be initiated at any time. The user can activate treatment button 160 at any time to initiate the treatment sequence. Treatment and imaging can occur simultaneously or occur sequentially. For example, a user can image, treat, image, treat, etc. As schematically illustrated in FIG. 15, the treatment sequence activates the treatment portion of the transducer 280 to create voids or lesions 550 below the surface 105. Note that FIG. 15 illustrates one embodiment of a depth 278 that corresponds to a muscle depth. In various embodiments, the depth 278 can correspond to any tissue, tissue layer, skin, dermis, fat, SMAS, muscle, or other tissue. Note that as illustrated, the energy 50 represented is for illustration purposes only. Certain figures including FIGS. 15-17 show energy 50 emanating from the entire length of the transducer housing (its entire opening such as corresponding to travel distance 272); however the actual energy is emitted from a sub-length of that, e.g., the actual transduction element of the transducer 280. In one embodiment, the transduction element of the transducer 280 is scanned in a linear motion to cover the region of interest, such that at any time the energy is not coming out of the entire transducer housing's length at once.

In one embodiment, CTS 20 generates ultrasound energy which is directed to and focused below the surface 501. This controlled and focused ultrasound energy creates the lesion 550 which may be a thermally coagulated zone or void in subcutaneous tissue 510. In one embodiment, the emitted energy 50 raises a temperature of the tissue at a specified depth 278 below the surface 501. The temperature of the tissue can be raised from about 1° C. to about 100° C. above an ambient temperature of the tissue, or about 5° C. to about 60° C. above an ambient temperature of the tissue or above 10° C. to about 50° C. above the ambient temperature of the tissue. In some embodiments, the emitted energy 50 targets the tissue below the surface 501 which cuts, ablates, coagulates, micro-ablates, manipulates, and/or causes a lesion 550 in the tissue portion 10 below the surface 501 at a specified depth 278. In one embodiment, during the treatment sequence, the transducer 280 moves in a direction denoted by the arrow marked 290 at specified intervals 295 to create a series of treatment zones 254 each of which receives an emitted energy 50 to create a lesion 550. For example, the emitted energy 50 creates a series of lesions 550 in the facial muscle layer 509 of tissue portion 10.

In various embodiments, delivery of emitted energy 50 at a suitable depth 278, distribution, timing, and energy level is provided by the emitter-receiver module 200 through controlled operation by the control system 300 to achieve the desired therapeutic effect of controlled thermal injury to treat at least one of the dermis layer 503, fat layer 505, the SMAS layer 507 and the facial muscle layer 509. During operation, the emitter-receiver module 200 and/or the transducer 280 can also be mechanically and/or electronically scanned along the surface 501 to treat an extended area. In addition, spatial control of a treatment depth 278 can be suitably adjusted in various ranges, such as between a wide range of about 0 mm to about 25 mm, suitably fixed to a few discrete depths, with an adjustment limited to a fine range, for example, approximately between about 3 mm to about 9 mm, and/or dynamically adjusted during treatment, to treat at least one of the dermis layer 503, fat layer 505, the SMAS layer 507 and the facial muscle layer 509. Before, during, and after the delivery of ultrasound energy 50 to at least one of the dermis layer 503, fat layer 505, the SMAS layer 507 and the facial muscle layer 509, monitoring of the treatment area and surrounding structures can be provided to plan and assess the results and/or provide feedback to the controller 300 and the user via the graphical interface 310.

As to the treatment of the SMAS layer 507 and similar fascia, connective tissue can be permanently tightened by thermal treatment to temperatures about 60° C. or higher. Upon ablating, collagen fibers shrink immediately by approximately 30% of their length. The shrunken fibers can produce tightening of the tissue, wherein the shrinkage should occur along the dominant direction of the collagen fibers. Throughout the body, collagen fibers are laid down in connective tissues along the lines of chronic stress (tension). On the aged face, the collagen fibers of the SMAS 507 region are predominantly oriented along the lines of gravitational tension. Shrinkage of these fibers results in tightening of the SMAS 507 in the direction desired for correction of laxity and sagging due to aging. The treatment includes the ablation of specific regions of the SMAS 507 region and similar suspensory connective tissues.

In addition, the SMAS layer 507 varies in depth and thickness at different locations, for example from about 0.5 mm to about 5 mm or more. On the face, important structures such as nerves, parotid gland, arteries and veins are present over, under or near the SMAS 507 region. Treating through localized heating of regions of the SMAS 507 layer or other suspensory subcutaneous tissue 510 to temperatures of about 60° C. to about 90° C., without significant damage to overlying or distal/underlying tissue, or proximal tissue, as well as the precise delivery of therapeutic energy to the SMAS layer 507, and obtaining feedback from the region of interest before, during, and after treatment can be suitably accomplished through the CTS 20.

In various embodiments, a method is provided for performing a brow lift on a patient. In some embodiments, the method includes coupling a probe 200 to a brow region 65 of the patient 60 and imaging at least a portion of subcutaneous tissue 510 of the brow region to determine a target area in the subcutaneous tissue 510. In an aspect of the embodiment, the method includes administering ultrasound energy 50 into the target area 525 in the subcutaneous tissue 510 to ablate the subcutaneous tissue 510 in the target area 525, which causes tightening of a dermal layer 503 above the subcutaneous tissue 510 of the brow region 65.

In various embodiments, a method is provided for tightening a portion of a dermal layer 503 on a facial area of a patient 60. In some embodiments, the method includes inserting a transducer module 200 into a band controller 100 and then coupling the transducer module 200 to a facial area of the patient 60. In one embodiment, the method includes activating a first switch 150 on the hand controller 100 to initiate an imaging sequence of a portion of tissue 10 below the dermal layer 503, then collecting data from the imaging sequence. In this embodiment, the method includes calculating a treatment sequence from the collected data, and activating a second switch 160 on the hand controller 100 to initiate the treatment sequence. In an aspect of the embodiments, the method can be useful on a portion of a face, head, neck and/or other part of the body of a patient 60.

With reference to FIG. 16, after the emitted energy has created lesions 550, healing and/or tightening of the portion of tissue 10 begins. In one embodiment, the void or lesion 550 can dissipate in the facial muscle layer 509 of the portion of tissue 10. For example, the facial muscle layer 509 has movement 560 around the lesion 550 to shrink the lesion 550. Eventually, the body essentially eliminates the lesion 550 through resorption, and can enhance the growth of tissue. This movement 560 causes upper layers such as the SMAS 507 to have movement 570 above where the lesion 550 was located. This in turn causes movement 580 at the surface 501 which tightens surface 501. This surface movement 580 at the surface 501 is the goal of any brow lift. The surface movement 580 creates a tightening effect across the skin surface 501 which can provide a more youthful look for the subject 500. In various embodiments, a medicant can be applied during the coupling of the CTS 20 to the portion of tissue 10. This medicant can be activated in the target zone 525 by the emitted energy 50 and can assist, accelerate, and/or treat the void or lesion 550 during the dissipation and/or healing of the void or lesion 550. Medicants include, but are not limited to, hyaluronic acid, retinol, vitamins (e.g., vitamin c), minerals (e.g., copper) and other compounds or pharmaceuticals that can be activated by energy and/or would benefit from deeper penetration into the skin.

Figure 18:
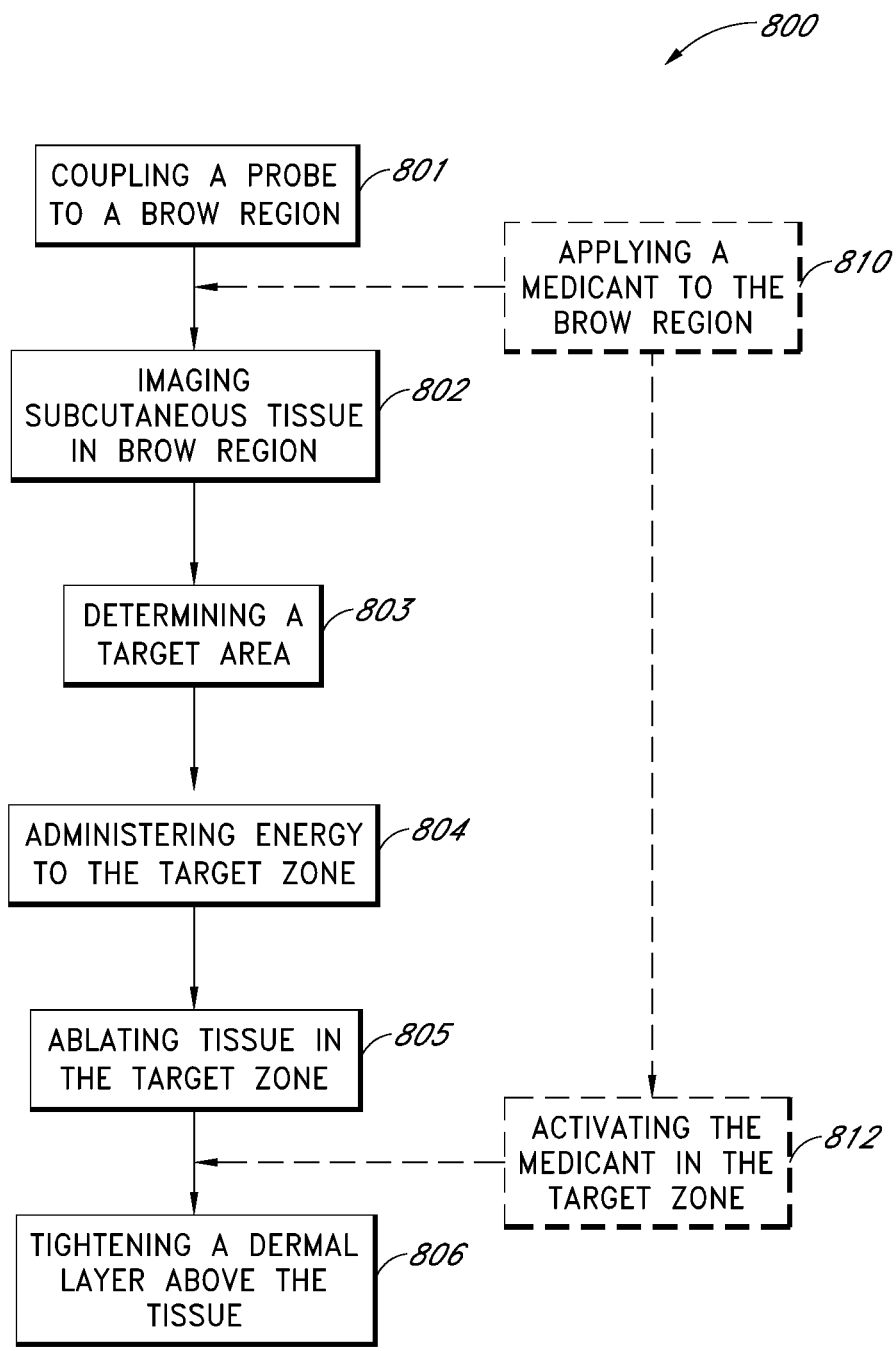
FIG. 18 is a flow chart depicting a method according to various embodiments of the present invention.

Turning to FIG. 18, a flow chart illustrates a method according to various embodiments of the present invention. A method 800 can include a first step 801 which is a coupling of a probe to a brow region. For example, step 801 can include the coupling of the emitter-receiver module 200 to a portion of tissue 10 in a ROI 65 of the subject 500. This step 801 can include a gel located between the emitter-receiver module 200 and the portion of tissue 10 that assists in the coupling of a probe to the brow region. Step 801 can move to step 802 which is imaging subcutaneous tissue 510 in the brow region. Step 802 can include imaging the portion of tissue 10 using the CTS 20 as discussed herein. Optionally, a step 810 can be included between steps 801 and 802. Step 810 is the applying a medicant to the brow region. The medicant can be any substance or material that has an active ingredient that may be helpful in the tightening of the surface 501 and/or in the healing and/or dissipation of the void or lesion 550 in a portion of tissue 10 below the surface 501. In one embodiment, the medicant can also act as a coupling gel useful in step 801. Step 802 moves to step 803 which is determining a target zone 525. Step 803 can include reviewing an image that was created in step 802 to help determine the target zone 525.

Step 803 moves to step 804 which is the administering of energy to the target zone 525. For example, step 804 can be illustrated in, for example, FIG. 15. Note that FIG. 15 illustrates one embodiment of a depth 278 that corresponds to a muscle depth. In various embodiments, the depth 278 can correspond to any tissue, tissue layer, skin, dermis, fat, SMAS, muscle, or other tissue. Step 804 moves to step 805 which is ablating the tissue in the target zone 525. In various embodiments, this "ablating" may be coagulation instead of ablation. Ablation is more or less instantaneous physical removal, analogous to sublimation or vaporization, while thermal coagulation is milder in that it is killing tissue but leaving it in place. Step 805 is illustrated in FIG. 15. Note that FIG. 15 illustrates one embodiment of a depth 278 that corresponds to a muscle depth. In various embodiments, the depth 278 can correspond to any tissue, tissue layer, skin, dermis, fat, SMAS, muscle, or other tissue. In step 805, the void or lesion 550 is created in a portion of tissue 10 below the surface 501. Step 805 moves to step 806 which is tightening a dermal layer 503 above or below the treated tissue. In the illustrated embodiment, step 806 is merely tightening a dermal layer above the tissue, but the broader step described is possible in various embodiments. Step 806 is illustrated in FIG. 17. For example, one of the surface 501 in the dermal layer 503 is tightened due to the void or lesion 505 being dissipated or healed. Between step 505 and 506, an optional step 812 may be used. Typically, for step 812 to be used, optional step 810 must also be used. In step 812, the medicant is activated in the target zone 525. This activation of the medicant can allow active ingredient to assist in tightening the dermal layer 503 above the ablate tissue. For example, the active ingredient may assist in the healing or dissipating of the void or lesion 550. In another example, the medicant may be activated at the surface 501 or in the dermal layer 503 to assist tightening.

Figure 19:
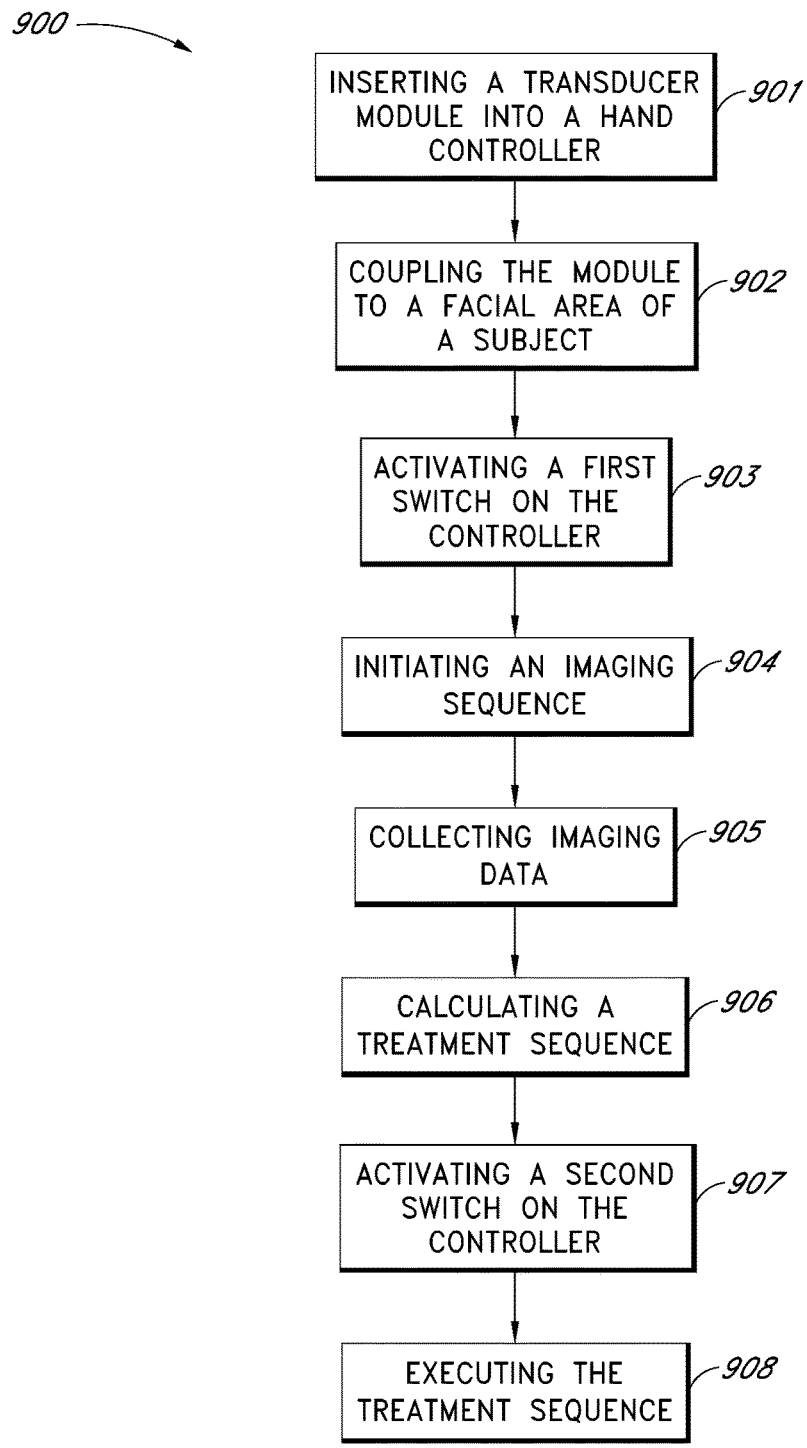
FIG. 19 is a flow chart depicting another method according to various embodiments of the present invention.

With reference to FIG. 19 a method 900 is illustrated according to various embodiments of the present invention. Method 900 begins with inserting a transducer module to the hand controller. For example, method 900 can include the inserting of the emitter-receiver module 200 into the hand wand 100. Step 901 moves to step 902 which is the coupling of the module to a facial area of the subject. For example, step 902 can include coupling the emitter-receiver module 200 to a region of interest 65 of a subject 63. Step 902 moves to step 903 which is activating a first switch on the hand controller. For example, step 903 can include activating an imaging button 150 on the hand wand 100. Step 903 moves to step 904 which is initiating the imaging sequence. For example, step 904 can include imaging sequence that can be collected by the CTS 20 as discussed herein. Step 904 moves to step 905 which is collecting imaging data. Step 905 moves to step 906 which is calculating a treatment sequence. In various embodiments, "calculating" as used with respect to step 906 can be determining, selecting, selecting a predetermined treatment sequence, and/or selecting a desired treatment sequence. For example, step 906 can include the controller 300 downloading a treatment sequence to the hand wand 100 and the emitter-receiver module 200. Step 906 moves to step 907 which is the activating of a second switch on the hand controller. For example, step 907 can be the activating of the treatment button 160 on the hand wand 100. Step 907 moves to step 908 which is executing the treatment sequence. For example, step 908 can be any treatment sequence as discussed herein. In other embodiments, the illustrated method may be broader to include generalized activating of switches anywhere and anyhow, such as with foot switches or switches on the controller 300, in various non-limiting embodiments.

Figure 20:
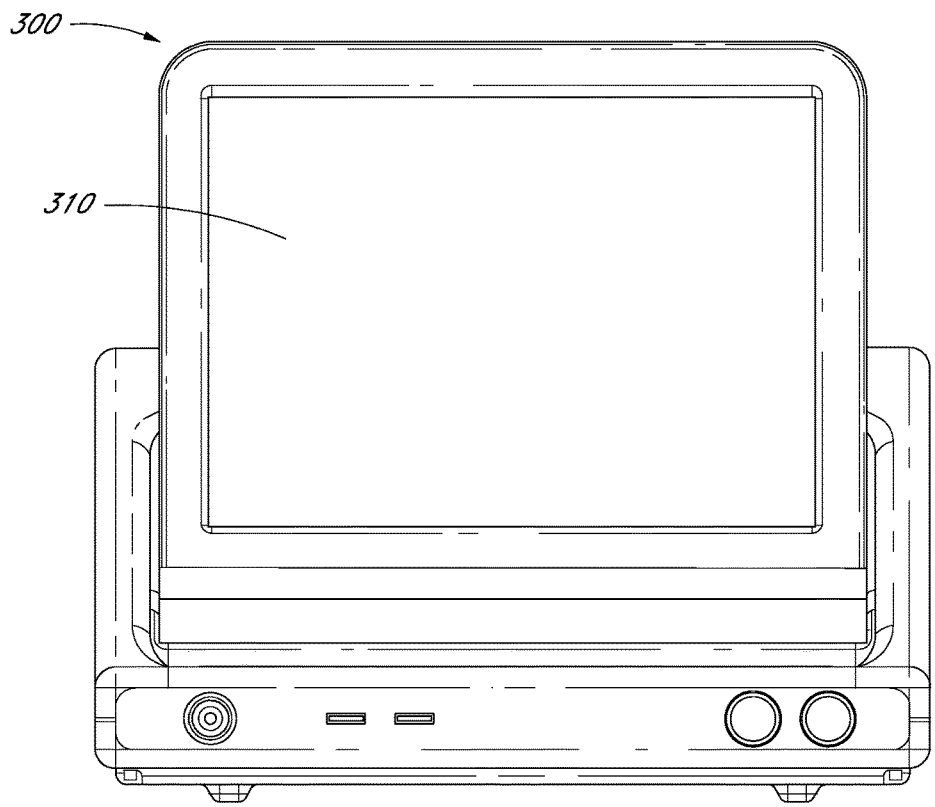
FIG. 20 is a front view illustrating a controller according to various embodiments of the present invention.
Figure 21:
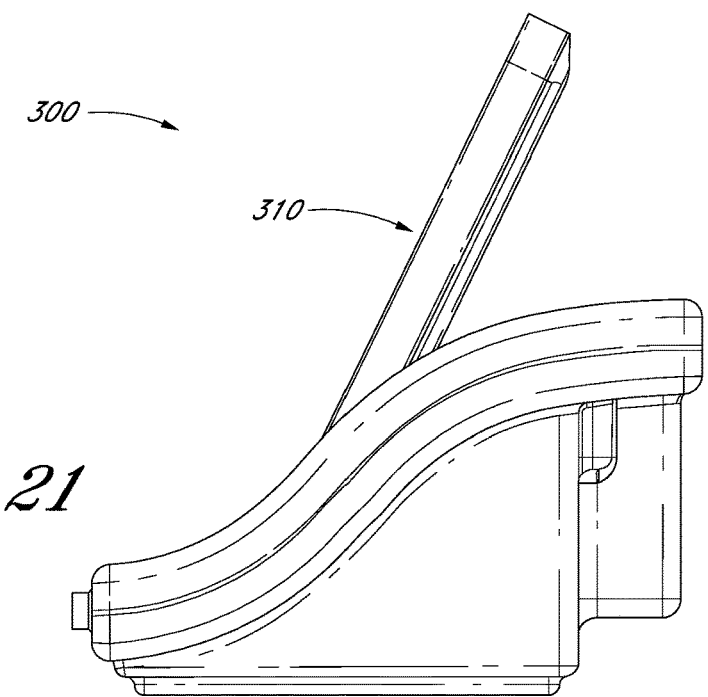
FIG. 21 is a side view illustrating a controller according to various embodiments of the present invention.
Figure 22:
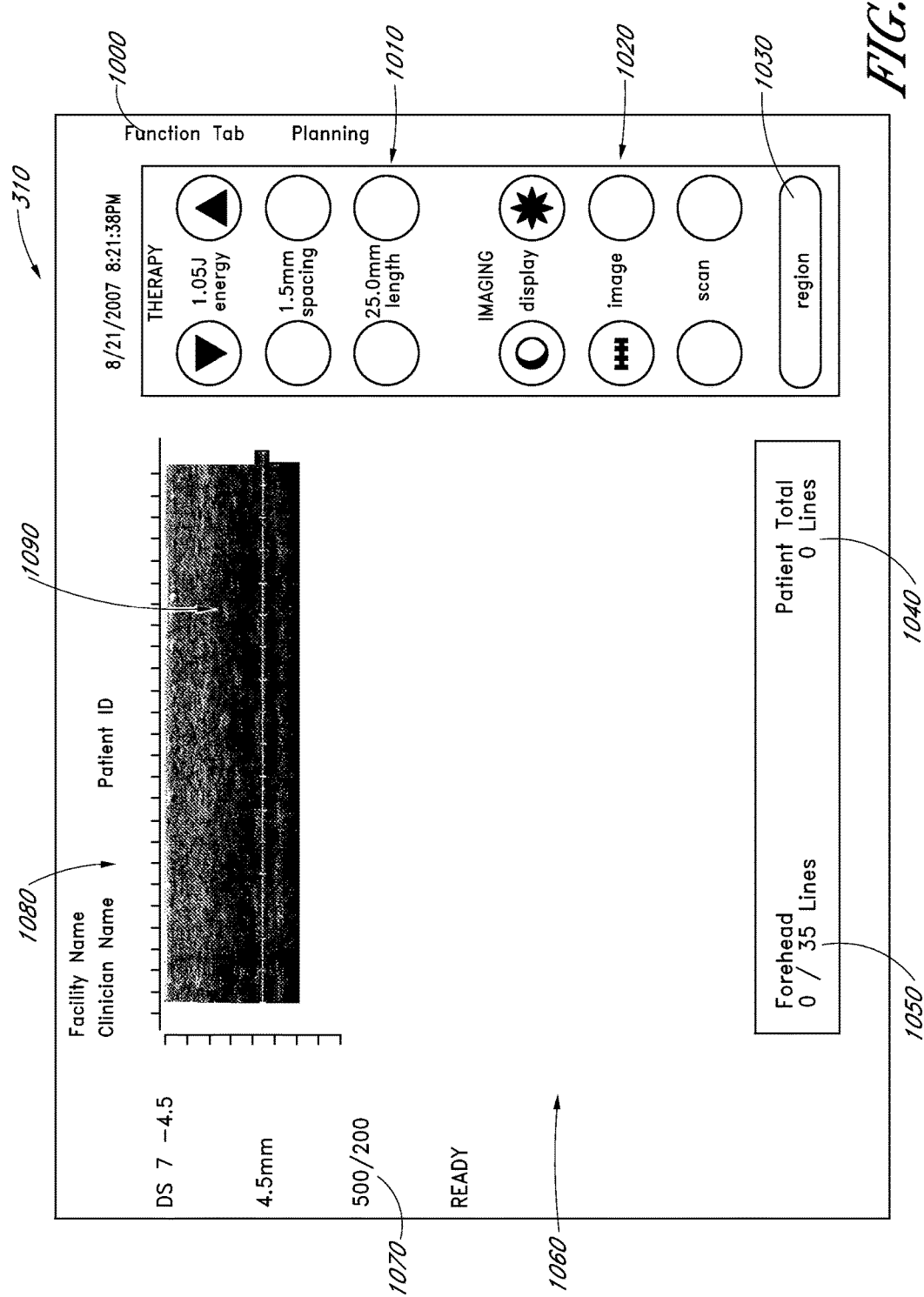
FIG. 22 is a representation of an interactive graphical display on a controller according one embodiment of the present invention.

FIGS. 20-21 illustrate a front and side view of one embodiment of a controller 300 as previously described herein. FIG. 22 illustrates one embodiment of an interactive graphical display 310, which can include a touch screen monitor and Graphic User Interface (GUI) that allows the user to interact with the CTS 20. FIG. 22 illustrates a general example of an embodiment of an interactive graphical display 310, which may include system function tabs 1000, therapy controls 1010, imaging controls 1020, region control 1030, patient total line count 1040, treat zone line count 1050, system status 1060, probe information area 1070, header information 1080 and/or image-treat region 1090.

The system function tabs 1000 reflect aspects of the system function. In one embodiment, the interactive graphical display 310 has one or more general functions. In various embodiments the interactive graphical display 310 has two, three, four or more general functions. In one embodiment, an interactive graphical display 310 has three general functions: a planning function, a imaging/treatment function, and a settings function. In one embodiment, the planning function contains the controls and information instrumental in planning a treatment, which can automatically set therapy controls. In one embodiment, the planning function can display an overview of the various treatment regions with recommended treatment parameters for each. For example, parameters for treating such regions as the forehead, left or right temple, left or right preauricular, left or right neck, submental, and left or right cheek can show a recommended emitter-receiver module 200 listing energy levels and recommended numbers of lines of treatment. Certain areas can include a protocol listing for selection of treatment protocols, a protocol allowed treat regions listing, and disallowed regions that can not be selected due to an incorrect transducer, which can be grayed out. In one embodiment, the imaging/treatment function contains the controls and protocol information needed for imaging soft tissue and for treating pertinent soft tissue. In various embodiments, a start up screen can include patient and/or facility data. In one embodiment the imaging/treatment function can include a main startup screen. In one embodiment a imaging/treatment function can be configured for a forehead. The settings function allows the user to input, track, store and/or print patient treatment information outside the scanning function, and can include such information as patient and facility information, end treatment, treatment records, images, help, volume, and system shutdown controls and dialogs.

The therapy controls 1010 can set acoustic energy level, spacing for setting the distance between micro-coagulative zones, and length which can set the maximum distance of the treatment line and similar information.

The imaging controls 1020 can include marker (not scanning), display (scanning), image and scan information. The marker can include a distance icon to show calipers and text for annotation. The display can increase or decrease brightness or other display related characteristics. The image icon can toggle a treat ruler, or save an image. The scan buttons can start or stop scanning for imaging purposes and similar information.

The region control 1030 launches a dialog below the image to select tissue region. The patient total line count 1040 keeps track of the cumulative number of treatment lines delivered and similar information. The treat zone line count 1050 indicates a zone of treatment, such as forehead or submental, etc. and can display the lines delivered to a zone or a protocol for recommended lines and similar information. The system status 1060 can display that the system is ready, treating, or other mode-dependent system messages and similar information. The probe information area 1070 can display the name of the attached transducer, the treatment depth of the transducer, and the number of lines spent/(vs.) total line capacity of transducer and similar information. The header information 1080 can include the facility, clinician, patient name and patient identification, date and time and similar information. The image-treat region 1090 can include an ultrasound image, horizontal and vertical (depth) rulers with 1 mm tick marks or other measuring dimensions, a treatment ruler indicating spacing, length and depth of treatment, and other similar information.

One benefit or advantage of using a treatment system that also allows imaging is that a user can verify that there sufficient coupling between the transducer and the skin (such as by applying coupling gel between the emitter-receiver module 200 and skin) by ensuring there are not dark, vertical bars, as indicative of air pockets between the face of the transducer and patient. A lack of coupling may result in a region that is improperly treated. Corrective action might include placing more coupling ultrasound gel to ensure proper contact and communication between the device and the patient.

Therapeutic treatment can be initiated by pressing the treatment button 160 on the hand wand 100. In one embodiment, an indicator 155 will display a yellow light to indicate the system is in the "treating" state. As the energy 50 is delivered a continuous tone is sounded and a yellow 'treating' line will advance over the green 'ready' treatment line on the screen. To deliver the next line of energy in the same treatment area, the user can advance the transducer roughly 1-6 mm, or roughly 2-3 mm (depending on the treatment, region, etc.) to adjacent tissue and press the treatment button 160 again. In various embodiments, a time period can elapse between delivering a previous line of energy 50. In various embodiments, the time period can be 1 second, 5 seconds, 10 seconds, or any other duration. In one embodiment, if five or ten seconds (or some other duration) have elapsed between delivering the previous line of energy 50, the user can press the imaging button 150 on the hand wand 100 to restore the "ready" state, and then press the treatment button 160 next to it. Treatment can continue in this fashion until the recommended number of lines (as shown on the bottom/center of the screen) has been delivered. In one embodiment, when the correct number of lines is delivered, the line count color turns from orange to white.

In one embodiment, the settings function allows a user to export images. Stored images are listed in the bottom dialog box and the most recently user-selected image is displayed above it. If an external storage device and/or printer is attached then image file export and/or printing is enabled, respectively. In one embodiment, the settings function allows a user to export records.

In certain embodiments, the interactive graphical display 310 can display error messages to direct appropriate user responses, such as in one embodiment of an error message.

The citation of references herein does not constitute admission that those references are prior art or have relevance to the patentability of the teachings disclosed herein. All references cited in the Description section of the specification are hereby incorporated by reference in their entirety for all purposes. In the event that one or more of the incorporated references, literature, and similar materials differs from or contradicts this application, including, but not limited to, defined terms, term usage, described techniques, or the like, this application controls.

Some embodiments and the examples described herein are examples and not intended to be limiting in describing the full scope of compositions and methods of these invention. Equivalent changes, modifications and variations of some embodiments, materials, compositions and methods can be made within the scope of the present invention, with substantially similar results.

What is claimed is:

1. A hand wand for use in cosmetic treatment, the wand comprising:
   a handle comprising an integrated receptacle configured for insertion of at least one of a first removable transducer module and a second removable transducer module, and an electrical cable,
   wherein said first removable transducer module and second removable transducer module are configured for interchangeable coupling to the handle with a spring pin connector,
   wherein the first removable transducer module comprises:
      a first ultrasonic treatment piezoelectric element configured to focus ultrasound at a first depth in a range between 3 mm and 4.5 mm below a skin surface with a first treatment frequency in a range of 1 MHz to 10 MHz at a first acoustic power in a range of 1 watt to 100 watts;
      a first printed circuit board configured for electrical connection to the spring pin connector, and
      a first storage device containing data for calibration or storage in a first sealed housing,
      the first sealed housing comprising a first acoustic fluid and a first acoustically transparent window,
      wherein the first ultrasonic treatment piezoelectric element is acoustically coupled to the first acoustically transparent window via the first acoustic fluid in the first sealed housing,
   wherein the second removable transducer module comprises:
      a second ultrasonic treatment piezoelectric element configured to focus ultrasound at a second depth in a range between 3 mm and 4.5 mm below the skin surface with a second treatment frequency in a range of 1 MHz to 10 MHz at a second acoustic power in a range of 1 watt to 100 watts,
      a second printed circuit board configured for electrical connection to the spring pin connector, and
      a second storage device containing data for calibration or storage in a second sealed housing,
      the second sealing housing comprising a second acoustic fluid and a second acoustically transparent window, wherein the second ultrasonic treatment piezoelectric element is acoustically coupled to the second acoustically transparent window via the second acoustic fluid in the second sealed housing,
   a movement mechanism comprising a shaft, a stepper motor, a scotch yoke, and a magnetic coupling, the movement mechanism configured to move at least one of the first ultrasonic treatment piezoelectric element and the second ultrasonic treatment piezoelectric element along the shaft to direct a ultrasonic treatment in a linear sequence of individual thermal lesions,
   wherein the movement mechanism further comprises an encoder disposed on the shaft, the encoder configured for measuring a position of the first ultrasonic treatment piezoelectric element along the shaft in the first sealed housing,
   an image button on the handle operably controlling an ultrasonic imaging piezoelectric element for providing ultrasonic imaging on a display,
   wherein the display comprises a graphical user interface,
   wherein the graphical user interface displays any one of the group of an operating condition, equipment status, and a system message;
   a treatment button on the handle operably controlling said first ultrasonic treatment piezoelectric element when the first removable transducer module is coupled to the handle to provide a first ultrasonic treatment function for providing a first ultrasonic treatment with the first removable transducer module at a first depth configured for treatment in at least one of the group consisting of: skin, superficial muscular aponeurotic system ("SMAS"), or fat,
   wherein the treatment button on the handle is configured for operably controlling said second ultrasonic treatment piezoelectric element when the second removable transducer module is coupled to the handle to provide a second ultrasonic treatment function for providing a second ultrasonic treatment with the second removable transducer module at a second depth configured for treatment in at least one of the group consisting of: skin, SMAS, or fat;
   wherein said first depth is different than said second depth, and wherein said first removable transducer module and second removable transducer module are configured to be operably coupled to said image button and said treatment button, wherein the movement mechanism is configured for travel through a liquid-tight seal, wherein the movement mechanism moves the first ultrasonic treatment piezoelectric element when the first removable transducer module is coupled to the handle, and wherein the movement mechanism moves the second ultrasonic treatment piezoelectric element when the second removable transducer module is coupled to the handle.

2. The hand wand of claim 1, further comprising a third removable transducer module comprising:
  a third ultrasonic treatment piezoelectric element configured to focus ultrasound at a third depth in a range of 1.5 mm to 2 mm below the skin surface with a third treatment frequency in a range of 1 MHz to 10 MHz at a third acoustic power in a range of 1 watt to 100 watts,
  a third printed circuit board configured for electrical connection to the spring pin connector, and
  a third storage device containing data for calibration or storage in a third sealed housing,
  the third sealing housing comprising a third acoustic fluid and a third acoustically transparent window, wherein the third ultrasonic treatment piezoelectric element is acoustically coupled to the third acoustically transparent window via the third acoustic fluid in the third sealed housing.

3. The hand wand according to claim 1, wherein said first removable transducer module and second removable transducer module are configured to provide treatment at different depths below the skin surface.

4. The hand wand of claim 1, wherein at least one of the image button and the treatment button is connected to a microprocessor for activating said first removable transducer module and second removable transducer module.

5. The hand wand of claim 1, wherein the scotch yoke comprises a slot to interface with a pin attached to the stepper motor as the pin moves in a circular path to linearly move the first ultrasonic treatment piezoelectric element.

6. A wand for use in cosmetic treatment, the wand comprising:
  a first button on said wand operably controlling an imaging function;
  a second button on said wand operably controlling a treatment function;
  a movement mechanism,
  an integrated receptacle comprising a spring pin connector, and
  a removable transducer module comprising:
    a printed circuit board configured for electrical connection to the spring pin connector operably coupled to said wand at the integrated receptacle,
    a sealed housing comprising an acoustically transparent window
    an acoustic fluid, and
    an ultrasonic treatment piezoelectric element
  wherein said ultrasonic treatment piezoelectric element is contained with the sealed housing and is configured for acoustic coupling to the acoustically transparent window via the acoustic fluid,
  wherein the ultrasonic treatment piezoelectric element is configured to focus ultrasound at a depth in a range between 3 mm and 4.5 mm below a skin surface with a treatment frequency in a range of 1 MHz to 10 MHz at an acoustic power in a range of 1 watt to 100 watts,
  wherein the movement mechanism moves the ultrasonic treatment piezoelectric element inside the removable transducer module along a shaft when the removable transducer module is coupled to the handle,
  wherein the movement mechanism comprises a stepper motor, a scotch yoke, and a magnetic coupling, the movement mechanism configured to direct a ultrasonic treatment in a linear sequence of individual thermal lesions,
  wherein the movement mechanism further comprises an encoder provided along the shaft, the encoder being configured to measure a position of the ultrasonic treatment piezoelectric element along the shaft in the sealed housing.

7. The wand according to claim 6, wherein said ultrasonic treatment piezoelectric element in the removable transducer module is coupled to said second button.

8. The wand according to claim 6, further comprising a latch mechanism removably holding said removable transducer module in said wand.

9. The wand according to claim 6, wherein the movement mechanism comprises a clutch rod and the magnetic coupling comprises a magnetic tip in the clutch rod are configured to move the ultrasonic treatment piezoelectric element to create a series of separated ablative lesions under the skin surface.

10. The wand according to claim 9, further comprising a graphical user interface for controlling said removable transducer module, and wherein the scotch yoke further comprises a slot comprises a slot to interface with a pin attached to the stepper motor as the pin moves in a circular path to move the ultrasonic treatment piezoelectric element to form the linear sequence of the individual thermal coagulation points in the tissue for the cosmetic effect.

* * * * *